(12) United States Patent
Gorek et al.

(10) Patent No.: US 11,083,447 B2
(45) Date of Patent: Aug. 10, 2021

(54) MINIMALLY OPEN INTERBODY ACCESS RETRACTION DEVICE AND SURGICAL METHOD

(71) Applicant: K2M, Inc., Leesburg, VA (US)

(72) Inventors: Josef E. Gorek, Ross, CA (US); Linda Krisciunas, Windham, NH (US); Catherine Ross, Arlington, VA (US); Jennifer Haggenmaker, Summit Point, WV (US); Kevin Strauss, Atlanta, GA (US)

(73) Assignee: K2M, Inc., Leesburg, VA (US)

( * ) Notice: Subject to any disclaimer, the term of this patent is extended or adjusted under 35 U.S.C. 154(b) by 51 days.

(21) Appl. No.: 16/564,769

(22) Filed: Sep. 9, 2019

(65) Prior Publication Data
US 2020/0077996 A1    Mar. 12, 2020

Related U.S. Application Data

(60) Continuation of application No. 15/619,862, filed on Jun. 12, 2017, now Pat. No. 10,405,841, which is a
(Continued)

(51) Int. Cl.
*A61B 17/02* (2006.01)
*A61B 17/56* (2006.01)
(Continued)

(52) U.S. Cl.
CPC ........ *A61B 17/025* (2013.01); *A61B 17/0206* (2013.01); *A61B 17/56* (2013.01);
(Continued)

(58) Field of Classification Search
CPC .......... A61B 2017/0256; A61B 17/025; A61B 17/66; A61B 2017/0262–0275
See application file for complete search history.

(56) References Cited

U.S. PATENT DOCUMENTS

| 1,613,141 A | 1/1927 | Stein |
| 2,693,795 A | 11/1954 | Grieshaber |

(Continued)

FOREIGN PATENT DOCUMENTS

| WO | 2006017886 A1 | 2/2006 |
| WO | 2006119447 A1 | 11/2006 |
| WO | 2007038418 A2 | 4/2007 |

OTHER PUBLICATIONS

About Endius/Corporate Overview. The Pioneer of Endoscopic Spine Fusion—Atavi System. (Internet Reference, 2002).
(Continued)

*Primary Examiner* — Nicholas J Plionis
(74) *Attorney, Agent, or Firm* — Lerner, David, Littenberg, Krumholz & Mentlik, LLP

(57) ABSTRACT

Devices, systems and methods for minimally open orthopedic spine surgery are disclosed. A first flexible screw-based retractor is designed to be coupled to each pedicle screw inserted into adjacent vertebral bodies. A retractor system is provided in which a first retractor blade is mounted to one of the screws and a second movable retractor blade is moved away from the first blade, in a medial direction, to create a working channel through which the disc space may be accessed for passing instruments and implants. Light may be incorporated into the device to illuminate the surgical field. One or all of the retractor blades may be made of a sterilizable plastic or metal and be disposable or reusable.

17 Claims, 55 Drawing Sheets

Related U.S. Application Data continuation of application No. 14/614,682, filed on Feb. 5, 2015, now Pat. No. 9,675,337, which is a division of application No. 12/104,653, filed on Apr. 17, 2008, now Pat. No. 8,979,749.

(60) Provisional application No. 60/925,056, filed on Apr. 17, 2007.

(51) Int. Cl.
  *A61B 17/70* (2006.01)
  *A61B 17/16* (2006.01)
  *A61B 17/28* (2006.01)
  *A61B 90/30* (2016.01)
  *A61B 17/00* (2006.01)

(52) U.S. Cl.
  CPC ...... *A61B 17/7077* (2013.01); *A61B 17/7082* (2013.01); *A61B 17/0293* (2013.01); *A61B 17/1655* (2013.01); *A61B 17/1671* (2013.01); *A61B 17/7037* (2013.01); *A61B 90/30* (2016.02); *A61B 2017/00407* (2013.01); *A61B 2017/0256* (2013.01); *A61B 2017/2837* (2013.01)

(56) References Cited

U.S. PATENT DOCUMENTS

| | | |
|---|---|---|
| 3,129,706 A | 4/1964 | Reynolds |
| 3,227,156 A | 1/1966 | Gauthier |
| 3,724,449 A | 4/1973 | Gauthier |
| 3,749,088 A | 7/1973 | Kohlmann |
| 3,750,652 A | 8/1973 | Sherwin |
| 4,263,899 A | 4/1981 | Burgin |
| 4,300,541 A | 11/1981 | Burgin |
| 4,545,374 A | 10/1985 | Jacobson |
| 4,747,394 A | 5/1988 | Watanabe |
| 4,852,552 A | 8/1989 | Chaux |
| 4,924,857 A | 5/1990 | Mahmoodian |
| 4,926,849 A | 5/1990 | Downey |
| 4,989,587 A | 2/1991 | Farley |
| 5,167,223 A | 12/1992 | Koros et al. |
| 5,190,548 A | 3/1993 | Davis |
| 5,242,443 A | 9/1993 | Kambin |
| 5,339,801 A | 8/1994 | Poloyko et al. |
| 5,503,617 A | 4/1996 | Jako |
| 5,512,038 A | 4/1996 | O'Neal et al. |
| 5,520,608 A | 5/1996 | Cabrera et al. |
| 5,529,571 A | 6/1996 | Daniel |
| 5,582,577 A | 12/1996 | Lund |
| 5,616,117 A | 4/1997 | Dinkier et al. |
| 5,667,520 A | 9/1997 | Bonutti |
| 5,697,944 A | 12/1997 | Lary |
| 5,707,359 A | 1/1998 | Bufalini |
| 5,707,362 A | 1/1998 | Yoon |
| 5,725,528 A | 3/1998 | Errico et al. |
| 5,728,046 A * | 3/1998 | Mayer ............... A61B 17/0293 600/210 |
| 5,813,978 A | 9/1998 | Jako |
| 5,885,210 A | 3/1999 | Cox |
| 5,902,231 A | 5/1999 | Foley et al. |
| 5,902,233 A | 5/1999 | Farley et al. |
| 5,928,139 A | 7/1999 | Koros et al. |
| 5,931,777 A | 8/1999 | Sava |
| 5,944,658 A * | 8/1999 | Koros ............... A61B 17/0206 600/231 |
| 5,967,972 A | 10/1999 | Santilli et al. |
| 6,099,547 A | 8/2000 | Gellman et al. |
| 6,139,493 A * | 10/2000 | Koros ............... A61B 17/0206 600/213 |
| 6,187,000 B1 | 2/2001 | Davison et al. |
| 6,200,322 B1 | 3/2001 | Branch et al. |
| 6,206,826 B1 | 3/2001 | Mathews et al. |
| 6,224,545 B1 | 5/2001 | Cocchia et al. |
| 6,241,659 B1 | 6/2001 | Bookwalter et al. |
| 6,270,501 B1 | 8/2001 | Freiberg et al. |
| 6,322,500 B1 | 11/2001 | Sikora et al. |
| 6,360,750 B1 | 3/2002 | Gerber et al. |
| 6,447,443 B1 | 9/2002 | Keogh et al. |
| 6,524,320 B2 | 2/2003 | DiPoto |
| 6,530,926 B1 | 3/2003 | Davison |
| 6,530,929 B1 | 3/2003 | Justis et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,553 B2 | 11/2003 | Davison et al. |
| 6,659,944 B2 | 12/2003 | Sharratt |
| 6,688,195 B1 | 2/2004 | Hsien |
| 6,743,206 B1 | 6/2004 | Smith |
| 6,767,355 B2 | 7/2004 | Frova et al. |
| 6,796,422 B1 | 9/2004 | Lu |
| 6,800,084 B2 | 10/2004 | Davison et al. |
| 6,849,064 B2 | 2/2005 | Hamada |
| 6,869,398 B2 | 3/2005 | Obenchain et al. |
| 6,929,606 B2 | 8/2005 | Ritland |
| 6,945,933 B2 | 9/2005 | Branch et al. |
| 7,004,945 B2 | 2/2006 | Boyd et al. |
| 7,008,422 B2 | 3/2006 | Foley et al. |
| 7,011,660 B2 | 3/2006 | Sherman et al. |
| 7,056,321 B2 | 6/2006 | Pagliuca et al. |
| 7,056,329 B2 | 6/2006 | Kerr |
| 7,083,621 B2 | 8/2006 | Shaolian et al. |
| 7,108,705 B2 | 9/2006 | Davison et al. |
| 7,144,393 B2 | 12/2006 | DiPoto et al. |
| 7,150,714 B2 | 12/2006 | Myles |
| 7,160,300 B2 | 1/2007 | Jackson |
| 7,166,107 B2 | 1/2007 | Anderson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,318,817 B2 | 1/2008 | Hamada |
| 8,979,749 B2 | 3/2015 | Gorek et al. |
| 2002/0077531 A1 | 6/2002 | Puchovsky et al. |
| 2002/0095139 A1 | 7/2002 | Keogh et al. |
| 2003/0004401 A1 | 1/2003 | Ball et al. |
| 2003/0149341 A1 | 8/2003 | Clifton |
| 2003/0191371 A1 | 10/2003 | Smith et al. |
| 2004/0024291 A1 | 2/2004 | Zinkel |
| 2004/0068268 A1 | 4/2004 | Boyd et al. |
| 2004/0093000 A1 | 5/2004 | Kerr |
| 2004/0093001 A1 | 5/2004 | Hamada |
| 2004/0176665 A1 | 9/2004 | Branch et al. |
| 2004/0215199 A1 | 10/2004 | Zinkel |
| 2004/0230100 A1 | 11/2004 | Shluzas |
| 2004/0230191 A1 | 11/2004 | Frey et al. |
| 2005/0010220 A1 * | 1/2005 | Casutt ............... A61B 17/7077 606/86 A |
| 2005/0065517 A1 | 3/2005 | Chin |
| 2005/0070765 A1 | 3/2005 | Abdelgany et al. |
| 2005/0080320 A1 | 4/2005 | Lee et al. |
| 2005/0101985 A1 | 5/2005 | Hamada |
| 2005/0113644 A1 | 5/2005 | Obenchain et al. |
| 2005/0159650 A1 | 7/2005 | Raymond et al. |
| 2005/0159651 A1 | 7/2005 | Raymond et al. |
| 2005/0165408 A1 | 7/2005 | Puno et al. |
| 2005/0203533 A1 * | 9/2005 | Ferguson ........... A61B 17/7077 606/90 |
| 2005/0215866 A1 | 9/2005 | Kim |
| 2005/0234304 A1 | 10/2005 | Dewey et al. |
| 2005/0240209 A1 | 10/2005 | Hamada |
| 2005/0277812 A1 | 12/2005 | Myles |
| 2006/0052812 A1 | 3/2006 | Winer |
| 2006/0142643 A1 | 6/2006 | Parker |
| 2006/0167487 A1 | 7/2006 | Hamada |
| 2006/0178693 A1 | 8/2006 | Hamada |
| 2006/0195114 A1 | 8/2006 | Bertagnoli |
| 2006/0229614 A1 | 10/2006 | Foley et al. |
| 2006/0264962 A1 | 11/2006 | Chin et al. |
| 2006/0271096 A1 | 11/2006 | Hamada |
| 2007/0038216 A1 | 2/2007 | Hamada |
| 2007/0055247 A1 | 3/2007 | Jahng |
| 2007/0083267 A1 | 4/2007 | Miz et al. |
| 2007/0106123 A1 | 5/2007 | Gorek et al. |

(56) References Cited

U.S. PATENT DOCUMENTS

| | | | |
|---|---|---|---|
| 2007/0129731 A1 | 6/2007 | Sicvol et al. | |
| 2007/0167954 A1 | 7/2007 | Sicvol et al. | |
| 2007/0191856 A1* | 8/2007 | Gil | A61B 17/025 606/90 |
| 2007/0203399 A1* | 8/2007 | Gephart | A61B 17/025 600/219 |
| 2007/0260125 A1 | 11/2007 | Strauss et al. | |
| 2008/0021285 A1 | 1/2008 | Drzyzga et al. | |
| 2008/0027432 A1 | 1/2008 | Strauss et al. | |
| 2008/0177260 A1* | 7/2008 | McKinley | A61B 17/7037 606/60 |
| 2008/0177270 A1 | 7/2008 | Sorrenti et al. | |
| 2008/0255567 A1* | 10/2008 | Accordino | A61B 17/86 606/90 |
| 2008/0262501 A1* | 10/2008 | Chen | A61B 17/025 606/90 |
| 2008/0312703 A1* | 12/2008 | Hestad | A61B 17/7085 606/86 A |
| 2009/0048632 A1* | 2/2009 | Firkins | A61B 17/7032 606/246 |
| 2009/0187080 A1 | 7/2009 | Seex | |
| 2010/0094345 A1* | 4/2010 | Saidha | A61B 17/7052 606/250 |

OTHER PUBLICATIONS

Aldrich, "Posterolateral microdiscectomy for cervical monoradiculopathy caused by posterolateral soft cervical disc dequestration", J. Neurosurg. 72:370-377 (1990).

Aronson, "The management of soft cervical disc protrusions using the Smith-Robinson approach", Clinical Neurosurgery 20:253-258 (1973).

Caspar, "A new surgical procedure for lumbar disc herniation causing less tissue damage through a microsurgical approach", Adv Neurosurg 4:72-80 (1977).

Cloward, "The Anterior Approach for Removal of Ruptured Cervical Disks", Presented at the meeting of the Harvey Cushing Society, Washington, DC, Apr. 22, 1958, pp. 602-617.

Extended European Search Report from EP Application No. 08746083.8 dated Mar. 24, 2015.

Fessler, et al., "A minimally invasive technique for decompression of the lumbar spine", Spine 27:432-438 (2002).

Fessler, et al., "Minimally Invasive Cervical Microendoscopic Foraminotomy: An Initial Clinical Experience", Neurosurgery 51(2):2-10 (2002).

Foley, et al., "Microendoscopic Discectomy", Techniques in Neurosurgery 3(4):301-307 (1997).

Henderson, et al., "Posterior-Lateral Foraminotomy as an Exclusive Operative Technique for Cervical Radiculopathy: A Review of 846 consecutively Operated Cases", Neurosurgery, 13(5): 504-521 (1983).

Hermantin, et al., "A Prospective, Randomized Study Comparing the Results of Open discectomy with Those of Video-Assisted Arthroscopic Microdiscectomy", The Journal of Bone and Joint Surgery 81A(7):958-965 (1999).

International Search Report for Application No. PCT/US2008/060602 dated Nov. 5, 2008, 3 pages.

Kawaguchi, et al., "Back Muscle Injury After Posterior Lumbar Spine Surgery", Spine, 21(8):941-944 (1996).

Lin, "Posterior Lumbar Interbody Fusion Technique: Complications and Pitfalls", PLIF Complications and Pitfalls, No. 193, pp. 90-102 (1985).

Lin, et al., "Posterior Lumbar Interbody Fusion", Clinical Orthopedics and Related Research, No. 180, pp. 154-168 (1983).

Malis, "Instrumentation and Techniques in Microsurgery", Clinical Neurosurgery, 26:626-636 (1979).

Rantanen, et al., "The Lumbar Multifidus Muscle Five Years After Surgery for a Lumbar Intervertebral Disc Herniation", Spine, 18(5):268-274 (1993).

Roh, et al., "Endoscopic Foraminotomy Using MED System in Cadaveric Specimens", Spine, 25(2):260-264 (2000).

Sihvonen, et al., "Local denervation atrophy of paraspinal muscles in postoperative failed back syndrome", Spine 18:575-581 (1993).

Styf, et al., "The Effects of External Compression by Three Different Retractors on Pressure in the Erector Spine Muscles During and After Posterior Lumbar Spine Surgery in Humans", Spine, 23(3):354-358 (1998).

Supplementary Partial European Search Report from Application No. EP 08746083.8 dated Dec. 3, 2014.

Tsai, et al., "Microscopic Laminotomies for Degenerative Lumbar Spinal Stenosis", Journal of Spinal disorders, 11 (5):389-394 (1998).

Weber et al, "Posterior surgical approach to the lumbar spine and its effect on the multifidus muscle", Spine 22:1765-1772 (1992).

Weiner, et al., "Microdecompression for Lumbar Spinal Canal Stenosis", Spine, 24(21):2268-2272 (1999).

\* cited by examiner

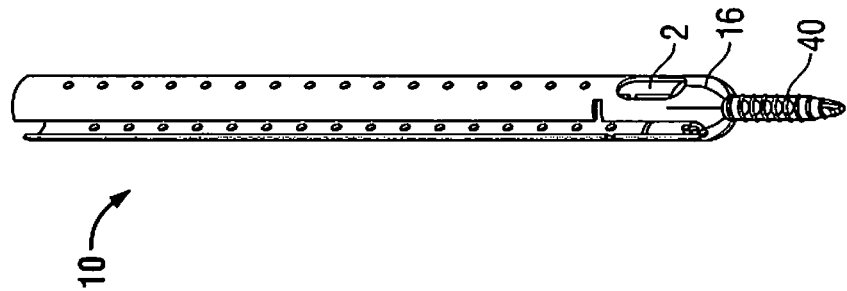
FIG. 4
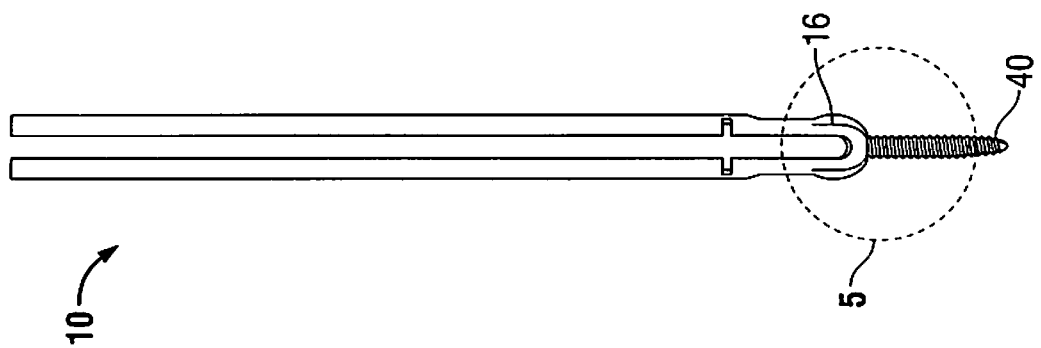
FIG. 3
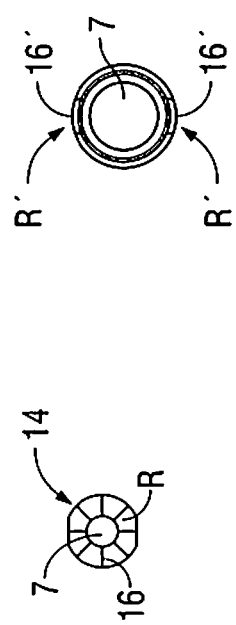
FIG. 2A
FIG. 2

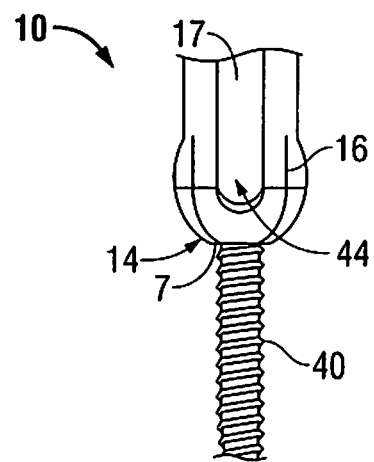
FIG. 5
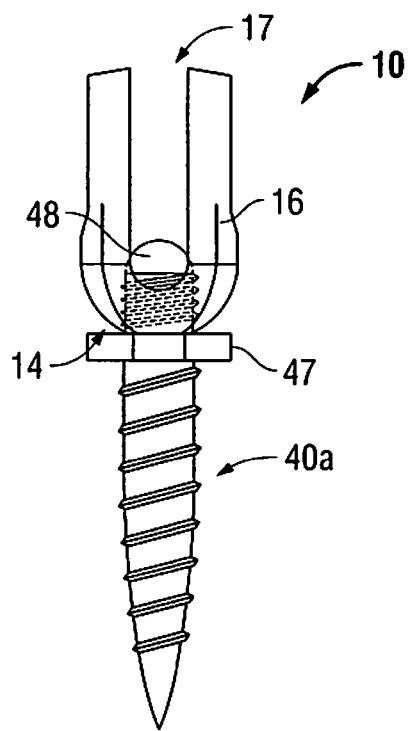 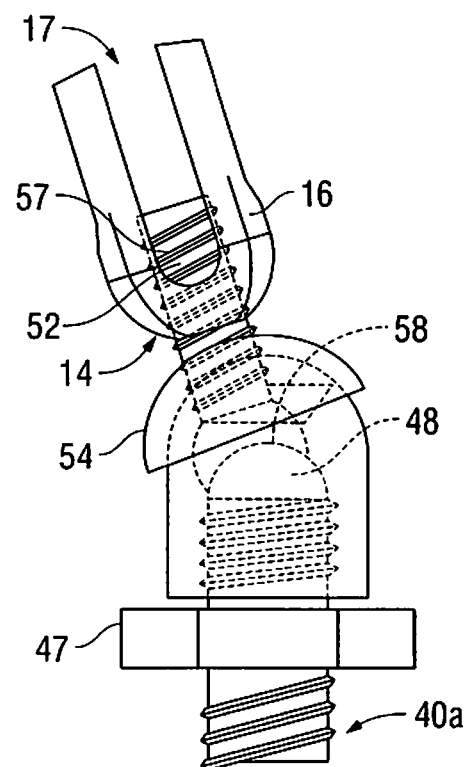
FIG. 5A      FIG. 5B

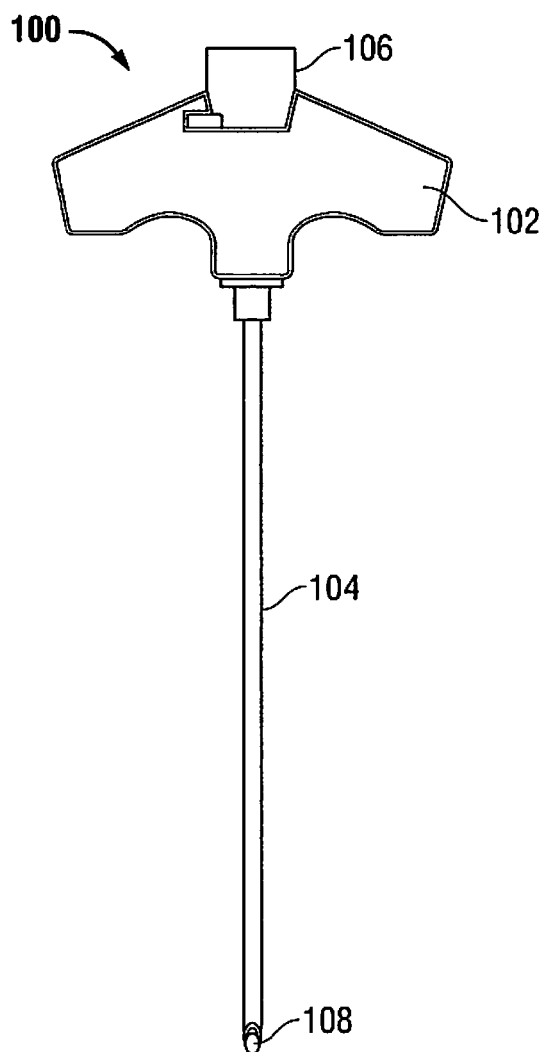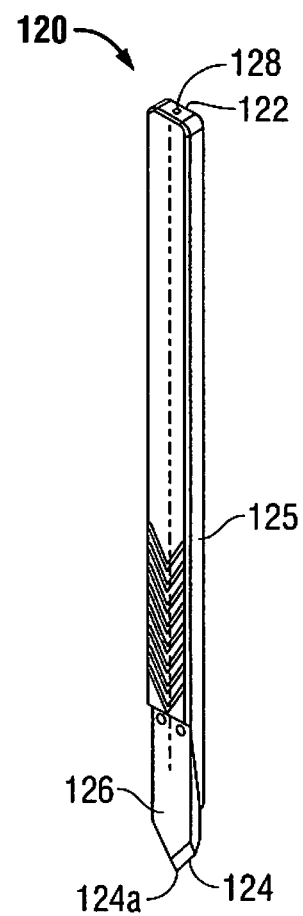
FIG. 8     FIG. 9

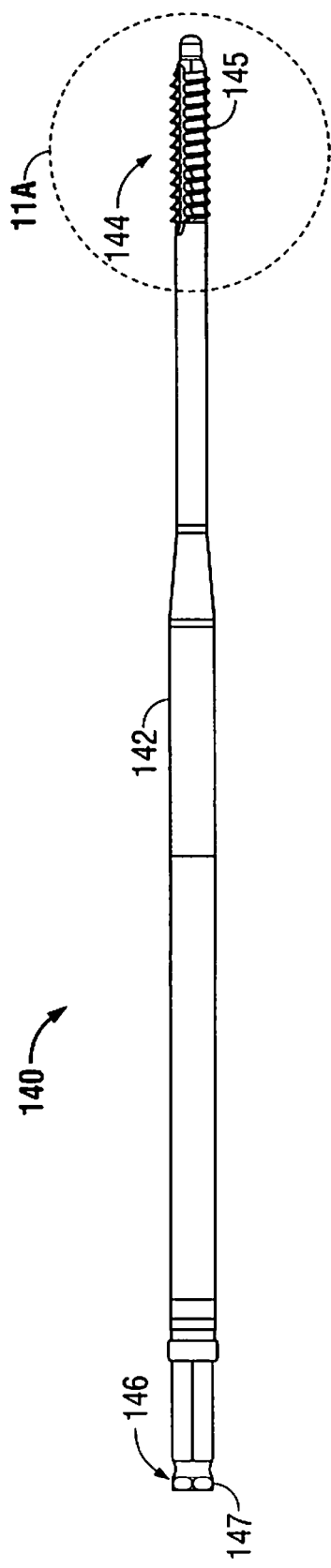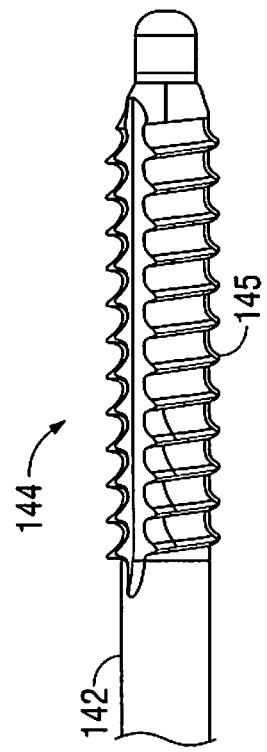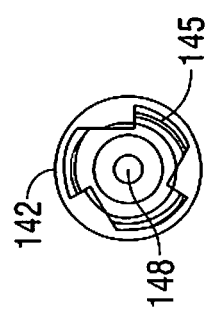
FIG. 11
FIG. 11B
FIG. 11A

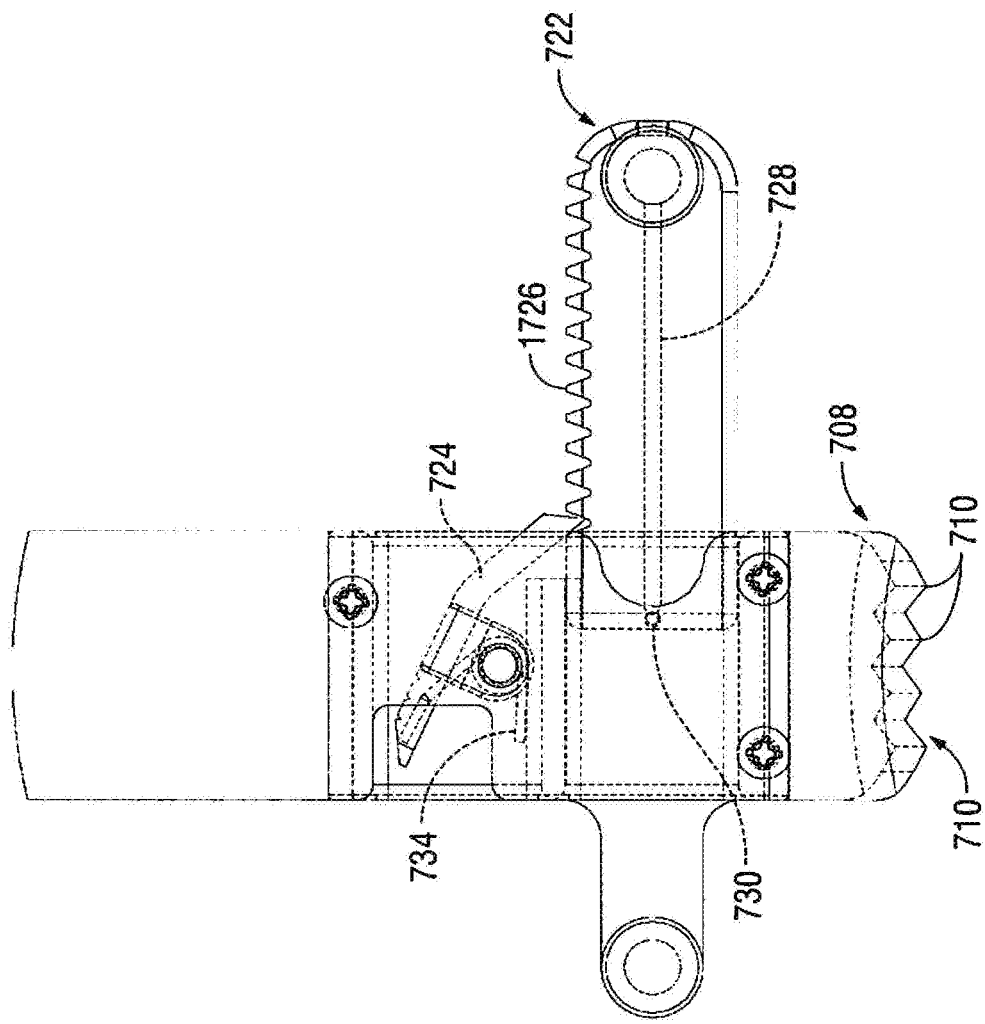
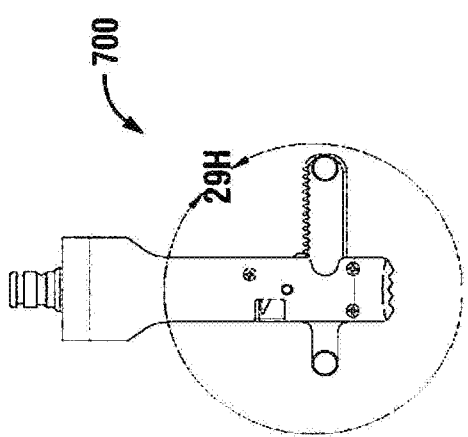

MINIMALLY OPEN INTERBODY ACCESS RETRACTION DEVICE AND SURGICAL METHOD

CROSS-REFERENCE TO RELATED APPLICATIONS

This application is a continuation of U.S. patent application Ser. No. 15/619,862, filed Jun. 12, 2017, which is a continuation of U.S. patent application Ser. No. 14/614,682, filed Feb. 5, 2015, which is a divisional of U.S. patent application Ser. No. 12/104,653, filed on Apr. 17, 2008, which claims priority to U.S. Provisional Patent Application Ser. No. 60/925,056, filed on Apr. 17, 2007, the contents of each of these prior applications are hereby incorporated by reference in their entirety.

TECHNICAL FIELD

The present disclosure relates generally to orthopedic spine surgery and in particular to devices, systems and methods for minimally open interbody access retraction devices and surgical methods.

BACKGROUND

The present disclosure relates generally to orthopedic spine surgery and specifically to unique retractor devices and surgical methods to perform orthopedic spine surgery by way of a minimally open or less invasive approach.

There has been considerable development of retractors and retractor systems for less invasive spine surgery procedures, with most of the new technologies being based on traditional types of surgical retractors for open procedures, predominantly table-mounted devices of various designs. These prior devices are large and bulky and frequently are not well suited to the smaller incisions and muscle sparing approaches desired for less invasive surgery. Most retractor systems may be classified as table mounted systems, handheld systems, and soft tissue anchored systems. Table-mounted systems generally contain a retractor attached to a surgical table through a support arm. As appreciated by one skilled in the art, the design of table-mounted systems is bulky and provides a user with limited degree of maneuverability. Standard hand-held surgical retractors are well known and can be modified to fit the contours of these smaller incisions, but they require manual manipulation to maintain position during surgery. Soft tissue anchored systems are positioned into the soft tissue and levered back to hold the wound open, frequently requiring re-positioning when they dislodge or obstruct the view or access pathways. The table mounted systems, handheld systems, and soft tissue anchored systems are all susceptible to displacement in numerous directions as a result of pressure exerted on the patient's body caused by, among other things, the surgeon's work within the body or the patient's breathing. The pressure exerted on the patient's body causes a reactionary force on the retractor and may displace the retractor from its original location.

There is, therefore, a demonstrated need for a retractor which can be self-retaining in the incision, can be fixed so as to inhibit dislodgement, does not require re-positioning yet allows for manual manipulation which increases the surgeon's procedural flexibility and is minimally obtrusive so as to not interfere with the surgical procedure.

Furthermore, the retractor should provide a protected working channel to access the disc space. To that end, it would be advantageous if the retractor could be expanded medially to increase visualization and exposure without enlarging the incision. Finally, a retractor device that is simple to introduce as well as remove will increase the likelihood of its use.

In recent years, minimally open surgical approaches have been applied to orthopedic spine surgery and, more recently, to spine fusions involving one or more vertebral bodies. Unlike minimally invasive procedures such as arthroscopic knee surgery or gallbladder surgery where the affected area is contained within a small region of the body, spine surgery involving a fusion typically spans a considerably larger length or portion of the body. For this reason, the idea of performing a minimally open procedure on the spine has only recently been approached.

By way of example, a typical spine fusion in the lumbar region, whereby at least two vertebral bodies are rigidly connected using screws implanted into the vertebral body and a rod spanning the distance between the screws is by its nature not very conducive to a minimally open approach. Furthermore, a spine fusion is typically supported by implanting one or more interbody devices into the disc space either using an anterior or posterior approach. An anterior approach requires a separate incision whereby the surgeon accesses the patient's spine through the abdomen. One advantage of the anterior approach is that the interbody used in this procedure closely matches the footprint of the adjacent vertebral bodies. The disadvantage is that an anterior procedure is typically performed at a different time and requires its own incision and access.

A posterior approach to interbody implantation can be achieved through the same incision as that of the pedicle screws. Implantation of a Posterior Lumbar Interbody Fusion (PLIF) device requires bilateral removal of the facet joints and requires introduction and implantation of two bilateral implants. A Transforaminal Lumbar Interbody Fusion (TLIF) approach can be achieved unilaterally and may require removal of only one facet joint. Another advantage of the TLIF approach is that only one device is implanted into the disc space While the implantation of pedicle screws can be achieved with relatively little site preparation, interbody implantation requires considerable access and surgical implant site preparation by the surgeon. Once the facet joint is removed, the surgeon can begin removing the disc. One or more instruments may be needed to access the site at any time as well as sufficient lighting and suction. To perform these tasks, the surgeon needs a suitable opening or channel to work through.

Several minimally open or minimally invasive access devices currently exist to achieve the goal of a suitable working channel. Most are either mounted to the surgical table or held in place by the surgeon or an assistant. Table mounted retractors offer little flexibility. Furthermore, such retractors do not offer a relationship or positional guidance with respect to the patient.

Handheld retractors provide greater flexibility but require an extra hand to maintain position. They also may or may not offer a fixed relationship to the patient but in either case can easily be knocked out of position. Furthermore, handheld retractors typically offer a very long and narrow fixed channel to work through making the procedure even more challenging. Several handheld retractors have been developed over the years. For example, U.S. Pat. No. 6,849,064 describes a handheld access system that has the ability to expand muscle tissue. To this end, this access system includes hinged bi-hemispherical or overall working tubes applied over an obturator that is controllably dilated to separate muscle tissue slowly.

Scientists have also developed soft tissue anchored retractors. These retractors are typically anchored to the patient's soft tissue rather than a table. As such, soft tissue anchored retractors offer the surgeon more flexibility than table mounted retractors but less flexibility than handheld retractors. There are different kinds soft tissue anchored retractors. U.S. Pat. No. 5,503,617 discloses a soft tissue anchored retractor for direct access endoscopic surgery. This retractor includes a rigid frame capable of supporting the applied loads required to perform retraction of an incision site. The rigid frame includes a handle at one end and a lower blade mount rotatably connected to the opposite end. A translation frame is slidably connected to the rigid frame and includes an upper blade mount rotatably connected thereto. Lower and upper blades are removably mounted on the lower and upper blade mounts, respectively.

Finally, any of the above-mentioned retractors typically require a form of dilation to obtain the initial opening. Circular or oblong dilators are well known in the art, but do not provide flexibility in configuring the desired access corresponding to the encountered anatomy. In addition, sequentially dilating tissue to make an opening large enough to perform surgery through the dilator or to accept a retracting device is tedious and can be traumatic to the patient. A retracting device that reduces or eliminates the steps associated with dilator devices would be advantageous. Minimally open surgery offers significant advantages over conventional open surgery. At the onset, the skin incision and subsequent scar are significantly smaller. A truly minimally open spine procedure should constitute the smallest damage or disruption possible to the surrounding anatomy. While there may be one or more incisions, depending on the number of levels needing attention, the amount of muscle and vascular retraction and scraping should be reduced to result in less operative trauma for the patient. A minimally open procedure also is likely to be less expensive, reduce hospitalization time, cause less pain and scarring, reduce the incidence of complications and reduce recovery time.

SUMMARY

The present disclosure illustrates several devices, methods and systems for performing orthopedic surgery, and more particularly spine surgery. Still more specifically, the instruments and methods of the present disclosure provide unique less invasive access to the spine from a posterior approach which facilitates interbody surgical procedures, including but not limited to a TLIF procedure, possibly supplemented by a screw and rod construct.

Broadly stated, the retractor system is secured relative to one or more surgical implants which, in turn, are affixed to bone, e.g., a pedicle screw, and a spreading device moves a retracting blade away from the portion of the system which is secured to the implant.

A first retraction system is disclosed having a first retractor blade which includes an extension member configured and dimensioned to be mounted temporarily into the rod receiving channel of an implanted pedicle screw. The system includes a second retractor blade and a spreading device. In use, the first retractor blade is mounted to an implanted pedicle screw and held in fixed relation thereto by temporarily locking the extension member to the screw, and the second retractor blade is inserted into the incision in opposing relation to the first blade. The spreading device is attached to both blades and is used to move the blades apart. Because the first blade is fixed relative to the pedicle screw, actuating the spreading device causes the second, movable blade to move apart from the first blade, thereby causing selective unilateral retraction in one direction. For a TLIF procedure, the first retractor is mounted to a screw and with the blade positioned on the lateral side of the incision, and the second retractor is moved away from the first retractor by the spreading device to cause medial retraction of the incision. In one embodiment, the first retractor mounted to the pedicle screw is offset laterally from the axis between a pair of screws implanted into adjacent vertebral bodies, thereby providing ideal access to the facet joint and the interbody space between the vertebral bodies when the retractor blades are spread apart.

The foregoing retractor system and method may be used in open or mini open surgery, where the surgeon creates an incision in the cephalad-caudad direction and implants at least one pedicle screw into a vertebral body. The retractor system may then be mounted to the at least one pedicle screw and used as described above to access the facet and interbody space.

The system and method may be used in conjunction with percutaneous, flexible screw based retractors to further reduce the invasive nature of the procedure. Thus, in this method, a pair of pedicle screws is inserted into the pedicles of adjacent vertebral bodies with a flexible retractor pre-assembled to each screw. The surgeon then rotates each flexible retractor such that the slot between the two blades of one retractor is perpendicular to the long axis of the spine. An incision is formed between the screws and the flexible retractors may be spread apart, such as with a Gelpi retractor, in a cephalad-caudad direction. Thereafter, the first substantially rigid retractor blade is mounted to one of the screws, with the refractor blade on the lateral side of the incision, a second blade is inserted opposite the first, and a spreading device is used to move the second blade in the medical-lateral direction to open the incision. In this manner, the flexible retractors define the cephalad-caudad boundaries of the access opening and the first and second relatively rigid retractors define the medial-lateral boundaries of the incision.

It has been found that this method provides ideal access for facet removal and a TLIF approach to interbody fusion. Once the facet and/or interbody work is complete, the surgeon removes the first and second rigid retractors and utilizes the flexible retractors in a medial-lateral orientation to insert a rod between the screws, compress or decompress the construct, and lock the rod to the screws in a manner appropriate for the particular screw system being utilized. The flexible retractors are then removed, such as with a retractor extractor instrument, the incision closed and the patient is permitted to recover. Because the size of the incision is minimized by the instruments and techniques described herein, it is anticipated that patient recovery time and post-operative comfort may be improved.

The systems and methods of the present disclosure advantageously permit spine surgery to be performed through an incision which closely approximates the minimum distance between two implanted spine screws, thereby sparing adjacent soft tissue, particularly muscle, from disruption. Indeed, fixing the lateral retractor relative to the screws advantageously permits the minimal length incision between the screws to be selectively retracted in the medial direction with the lateral blade slightly offset in the lateral direction from the axis between the screws, thus providing optimal access to the facet joint and the intervertebral space These and other advantages will be realized from the following detailed description of the several embodiments, and by practice with the systems and methods disclosed herein.

BRIEF DESCRIPTION OF DRAWINGS

Embodiments of the presently disclosed retraction device are described herein with reference to the accompanying drawings, wherein:

FIG. 2 is a bottom view of the flexible minimally invasive retractor of FIG. 1;

FIG. 2A is a bottom view of the flexible minimally invasive retractor of FIG. 1A;

FIG. 3 is a front view of the flexible minimally invasive retractor of FIG. 1 and screw assembly;

FIG. 4 is a perspective view of the minimally invasive retractor and screw assembly of FIG. 3;

FIG. 5 is an enlarged front sectional view of a portion of the minimally invasive retractor and screw assembly of FIG. 3, taken around section 5 of FIG. 3;

FIG. 5A is an alternate embodiment of the retractor of FIG. 5 illustrating the minimally invasive retractor disposed on a post of a monoaxial posted screw;

FIG. 5B is an alternate embodiment of the retractor of FIG. 5 illustrating the minimally invasive retractor disposed on a post of a polyaxial posted screw;

FIG. 8 is a side plan view of bone biopsy needle according to an embodiment of the present disclosure;

FIG. 9 is a perspective view of a cannulated scalpel according to an embodiment of the present disclosure;

FIG. 11 is a side plan view of a cannulated bone screw tap according to an embodiment of the present disclosure;

FIG. 11A is a front elevational view of the bone screw tap of FIG. 11;

FIG. 11B is an side enlarged sectional view of a portion of the bone screw tap of FIG. 11, taken around section A of FIG. 11;

FIG. 29G is a front view of the retractor of FIG. 29E;

FIG. 29H is an enlarged cross-sectional view of FIG. 29E, taken around section A of FIG. 29G;

DETAILED DESCRIPTION OF THE EMBODIMENTS

Figure 1C:
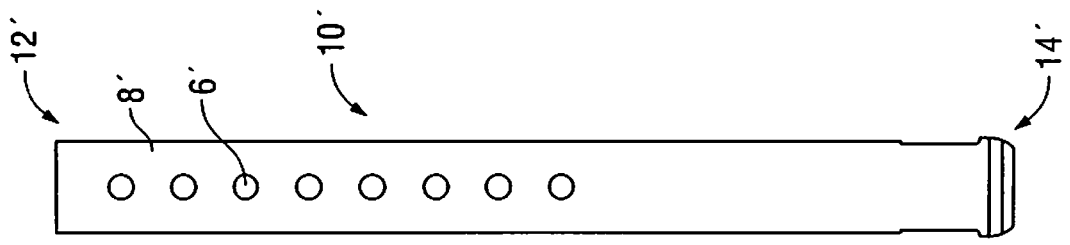
FIG. 1C is a side plan view of the flexible minimally invasive retractor of FIG. 1A.
Figure 1B:
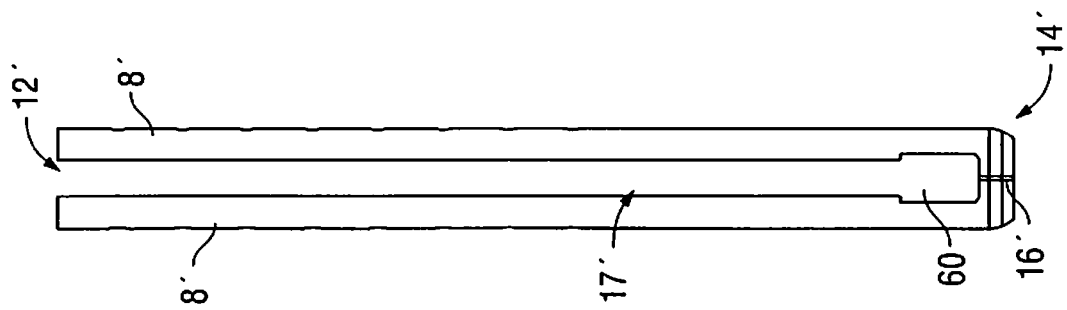
FIG. 1B is a front view of the flexible minimally invasive retractor of FIG. 1A.

The present disclosure describes devices, systems and methods for minimally open spine surgery. In the present disclosure, the pedicle screws may be inserted in an open, mini-open or percutaneous manner. In one embodiment of the methods and systems disclosed herein, the pedicle screws are introduced percutaneously with a screw based minimally invasive retractor or, more specifically, with a flexible percutaneous screw-based retractor that is removably attached to a pedicle bone screw. U.S. patent application Ser. No. 11/528,223, filed Sep. 25, 2006, entitled "Minimally Invasive Retractor and Methods of Use," which is hereby incorporated by reference in its entirety, describes several kinds of screw based retractors. The screw-based retractors disclosed in the foregoing application are designed to be spread apart in the medial-lateral direction to aid in rod introduction.

In one disclosed system and method, a pair of screws, each having a flexible screw based refractor, is percutaneously inserted into first and second adjacent vertebral bodies. In one embodiment, the configuration and orientation of the screw based retractors allows a Gelpi retractor to engage each retractor such that the Gelpi retractor is able to spread the retractor apart in a cephalad-caudad orientation. Either before or after engaging the Gelpi retractor with each of the flexible screw based retractors, an incision is made between the two implanted screws along a line between the two implanted screws to create a line of sight access directly to the facet joint and interbody space between the vertebral bodies to which the screws are implanted. Because the incision is made after the screws have been percutaneously implanted, the length of the incision is minimized and closely approximates the distance from one screw implantation site to the other. This spreading of the flexible screw based retractors and creation of an incision between the screws defines the cephalad and caudad boundaries of a working channel through which the disc space and associated anatomy may be accessed. In contrast, an open incision made to implant the screws would typically extend beyond the screw implantation sites in either direction, disrupting additional muscle and tissue. It is also contemplated, however, that the incision could be made first, the pedicle screws implanted with or without the flexible retractors, and a medial-lateral retractor system of this disclosure may be mounted to and used with at least one of the screws.

Once the cephalad-caudad boundaries of the working channel have been created, a second retractor system is introduced into the incision between the screws and spread in a medial-lateral fashion to create the desired opening to access the disc space.

In another embodiment, the second retractor system may include a pharyngeal-type rigid retractor blade. A distal end of the first rigid blade is mounted in fixed relation to one of the heads of the pedicle screws. A retractor blade has an integral extension configured and dimensioned to be inserted into the rod-receiving channel of the pedicle screw and to be temporarily fixed relative to the screw, such as by use of a temporary set screw. The blade extension is offset from the retractor blade, so that when the extension is fixed in the screw channel, the retractor blade is offset from the linear axis extending between the two screws. In one method, the retractor blade is offset in a lateral direction with the blade extension mounted in the rod-receiving channel of the screw.

The upper portion of the retractor blade extends out of the incision and is adapted to engage a spreading device. The spreading device has a first arm or side which attaches to the first relatively rigid retractor blade when the retractor blade is mounted to a screw. The spreading device has a second arm or side to which a second relatively rigid retractor blade may be attached. The second rigid blade is positioned in the incision opposite the first blade, and the spreading device is actuated to spread apart the two retractor blades. Because the first blade is fixed relative to one of the pedicle screws, the spreading device leverages off of that fixed blade and the second retractor blade is moved away from the first blade. If the first rigid blade is mounted laterally, the second rigid blade moves medially away from the first blade to retract tissue and provide access to the facet joint and disc space between the two vertebral bodies to which the pedicle screws are mounted. It has been found that the access provided by this approach is ideal for either a TLIF or PLIF approach to placing an intervertebral cage or spacer. Advantageously, because the first rigid retractor blade is fixed relative to one of the screws implanted in the vertebra, the retractor advantageously does not slide out of the incision or move within the incision to alter the boundaries or orientation of the incisional opening during surgery.

With the medial-lateral retractor in position, a surgical procedure may be performed on the facet joint and/or in the intervertebral space, including but not limited to a TLIF or PLIF approach fusion procedure.

After the desired surgical procedure has been performed, the medial-lateral refractor is removed. In this method the flexible percutaneous retractor blades are then spread apart in a medial lateral direction, and a rod is placed into the channel of each pedicle screw. Once the desired orientation and position of the rod and screws is achieved, the screws are locked onto the rod to complete the construct. The flexible percutaneous retractors are then removed from the screws and the incision is closed in a known manner to complete the procedure.

Embodiments of the presently disclosed minimally open interbody access retraction device will now be described in detail with reference to the drawings wherein like reference numerals identify similar or identical elements. In the drawings and in the description which follows, the term "proximal", as is traditional, will refer to the end of the minimally invasive retraction device which is closest to the operator while the term "distal" will refer to the end of the device which is furthest from the operator.

Figure 1A:
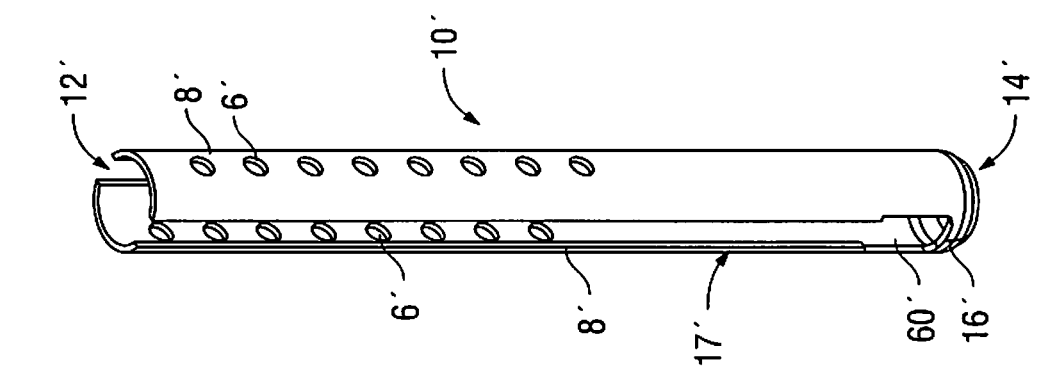
FIG. 1A is a perspective view of a flexible minimally invasive retractor according to an embodiment of the present disclosure.
Figure 1:
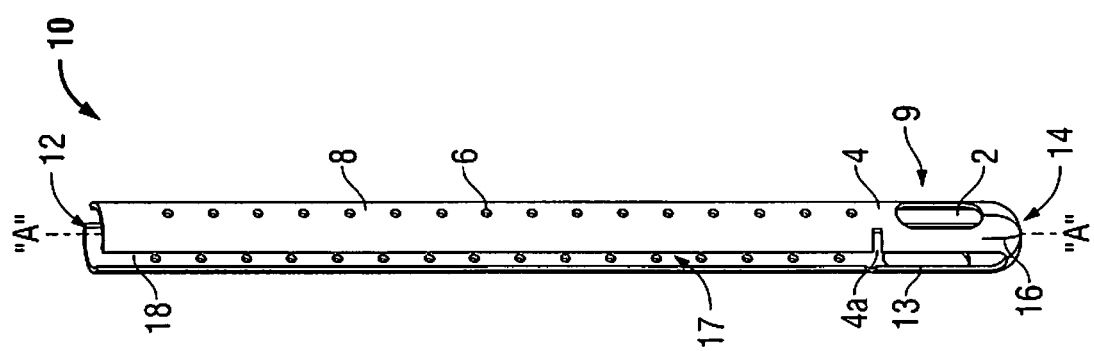
FIG. 1 is a perspective view of a flexible minimally invasive retractor according to an embodiment of the present disclosure.

Referring initially to FIGS. 1 and 2, a first embodiment of a flexible minimally invasive retractor is illustrated and generally designated as 10. Retractor 10 includes an open proximal end 12 and a distal end 14 and defines a longitudinal axis or centerline "A." In addition, retractor 10 includes a pair of flexible retractor blades 8 located on each side of the centerline "A" of retractor 10. Each flexible retractor blade 8 has a plurality of instrument holes 6 configured and dimensioned to cooperate with different surgical instruments as will be discussed in detail hereinafter. In this embodiment, the instrument holes 6 of each retractor blade 8 are arranged in a linear row that extends from a proximal portion to a distal portion of the retractor blade 8. Those skilled in art will contemplate other arrangements and configuration for instrument holes 6. A distal region 9 of retractor 10 includes an opening 7 (FIG. 2) and a pair of arms 13 extending from distal end 14 to a flexible region or living hinge 4. Each arm 13 may include at least one slot or window 2. Optional window 2 may be sized and configured to receive instruments or a rod therethrough. A living hinge 4 pivotally connects each flexible retractor blade 8 to a corresponding arm 13. Together, flexible retractor blade 8, living hinge 4, and arm 13 define a substantially continuous elongate member. A pair of recesses 4a, which are formed between flexible retractor blade 8 and arm 13, define each a living hinge 4. In addition, any suitable connecting apparatus or means may couple each flexible retractor blade 8 to a respective arm 13.

Distal end 14 further includes at least one relief region R (FIG. 2) defined by at least one slit 16 extending outwardly and proximally from opening 7 (FIG. 2). Alternatively, slit 16 may originate at window 2 and extend distally toward opening 7. It is contemplated that other arrangements of relief structures may be used to define relief region R and these may exist between opening 7 and window 2. Each slit 16 is a weakened portion of distal end 14. It may be a score in the material, a perforated region in the material, or another structural arrangement allowing relief region R to be radially displaced away from the centerline of retractor 10 in response to applied forces as will be discussed in detail hereinafter. In addition, distal end 14 has a generally convex outer surface that facilitates insertion of retractor 10 through layers of body tissue.

Flexible retractor blades 8 and arms 13 are generally arcuate structures that cooperate to define a substantially circular configuration for retractor 10. Each retractor blade 8 and each arm 13 have an arcuate configuration that is less than about 180.degree. and are radially spaced apart to define a continuous slot 17 along a substantial portion of retractor 10. In addition, each retractor blade 8 and its corresponding arm 13 define a passage 18 that also extends substantially the entire length of retractor 10. Passage 18 is expandable, as will be discussed in detail hereinafter, for receiving a rod 3 (FIG. 7) therein. Refractor blades 8 and arms 13 define a substantially circular ring shape, thereby providing sufficient stiffness (i.e. rigidity) such that retractor blades 8 and arms 13 resist bending from the counter forces of the retracted tissues.

Opening 7 is located at distal end 14 of retractor 10 and is sized for receiving the shank of a threaded screw 40 (FIGS. 3-4) therethrough, but inhibiting passage of a head 42 of screw 40 so as to support screw 40 at distal end 14 of retractor 10. The interior surface of distal end 14 has a generally concave spherical geometry that is adapted to receive, nest or mate with head 42 of pedicle screw 40.

One alternative version of flexible retractor which has proven acceptable is shown in FIGS. 1A-1C and 2A. As there shown, flexible minimally invasive retractor 10' has an open proximal end 12' and distal end 14'. Flexible retractor blades 8' have a plurality of instrument holes 6' on each of retractor blade arms 8' (shown in FIG. 1A as eight holes in each arm). Distal end 14' of retractor 10' includes an opening 7'. As in the prior embodiment, arms 8' are generally arcuate (although other cross-sectional configurations may be used) and together define a slot 17' along substantially the entire retractor 10'. As will be appreciated, in the configuration shown in FIG. 1A, slot 17' extends to the distal end 14' of the flexible retractor 10' and no separate window is defined. Likewise, no defined living hinge is shown in the configuration of FIG. 1A, as the configuration of FIG. 1A has been found suitable for molding and use without these features. As in the prior configuration, opening 7' is configured to receive a screw in the manner illustrated in FIGS. 3-4. In the configuration of FIGS. 1A-1C and 2A, a pair of opposed relief regions R' are defined by a pair of oppositely disposed score lines 16', or the like, extending partially through the wall of the distal end 14' of the flexible retractor 10'. This weakened section has been found appropriate for removal of the flexible retractor from the screw at the end of the procedure, as described below. As previously observed, flexible retractor 10' does not have a separate window adjacent the distal end of the retractor. Instead, flexible retractor 10' has an enlarged section of slot 17', which is generally designated as 60. Enlarged slot region 60 enhances visibility and access and provides sufficient flexibility of arms 8' without a separate window or separately defined living hinge.

In FIGS. 3-5, retractor 10 is illustrated in an assembled condition with a pedicle screw 40. Pedicle screw 40 extends through opening 7 (FIG. 2) such that threads of pedicle screw 40 extend beyond distal end 14 (FIG. 4) for insertion into a target site in a bone (e.g. a vertebral body). As shown in the figures, when pedicle screw 40 is inserted in retractor 10, the head 42 of the pedicle screw 40 sits within the interior geometry of distal end 14. As shown, rod receiving passage 44 of pedicle screw 40 (FIGS. 5 and 20) may align with opening 17 between retractor blades 8 facilitating the insertion of a rod into screw head 42. In addition, pedicle screw 40 is pivotable about the longitudinal axis of retractor 10 allowing retractor 10 to be attached in a first angular orientation with respect to the vertebral body, but pivotable about pedicle screw 40 increasing the amount of tissue that may be retracted using retractor 10.

Alternatively, the presently disclosed retractor 10 may be used in combination with a posted, monoaxial pedicle screw 40a (FIG. 5A) or with a polyaxial (i.e. multiaxial) pedicle screw 40b (FIG. 5B). Examples of suitable screws include the posted monoaxial screws of the TSRH® system available from Danek Medical, Inc. and the polyaxial screw disclosed in U.S. Pat. No. 5,725,528 to Errico et al., currently assigned to the assignee of the present application, the contents of which are hereby incorporated by reference in their entirety. In embodiments using posted pedicle screws, a separate plate (not shown) may be included for connecting the posted pedicle screws.

In FIG. 5A, the retractor 10 is positioned atop the posted screw 40a. The posted pedicle screw 40b includes a post 48 with threads thereon and a collar 47. The collar 47 has a greater circumferential diameter than either the post 48 or the shank of the posted pedicle screw 40a. In a previous embodiment, the distal tip of pedicle screw 40 was inserted through the distal opening of the retractor 10 (FIG. 4). In this embodiment, the posted pedicle screw 40b is installed in a desired location prior to installing the retractor 10. Subsequently, the retractor 10 is installed on top of the posted pedicle screw 40a by moving the retractor 10 toward the posted pedicle screw 40a such that the post 48 enters the distal opening of the retractor 10 and the distal end 14 of the retractor 10 rests upon a top surface of the collar 47.

Similarly, the retractor 10 may be used in combination with a polyaxial pedicle screw 40b as illustrated in FIG. 5B. The polyaxial pedicle screw 40b includes collar 47 and post 48 as previously described in connection with posted pedicle screw 40a. In addition, the polyaxial pedicle screw 40b includes a stem portion 52 having a threaded section 57 and a socket portion 56. The socket portion 56 includes a spherical recess formed at its bottom for slidably engaging the spherical portion of post 48. As such, the stem portion 52 is movable throughout a plurality of angles in relation to the shank of polyaxial pedicle screw 40b. After the polyaxial pedicle screw 40b is installed in a desired location, the retractor 10 is installed over the threaded section 57 of the stem portion 52 such that the distal end 14 of the retractor 10 abuts an outer surface of spacer 54.

Figure 7:
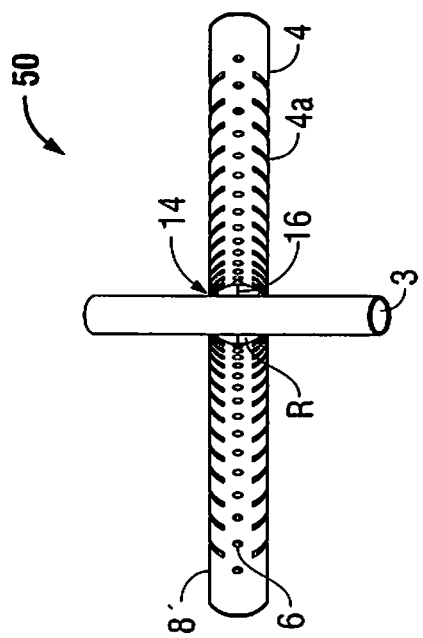
FIG. 7 is a top view of the minimally invasive retractor and screw assembly of FIG. 6 showing a rod extending through an expanded passage of the minimally invasive refractor.
Figure 6:
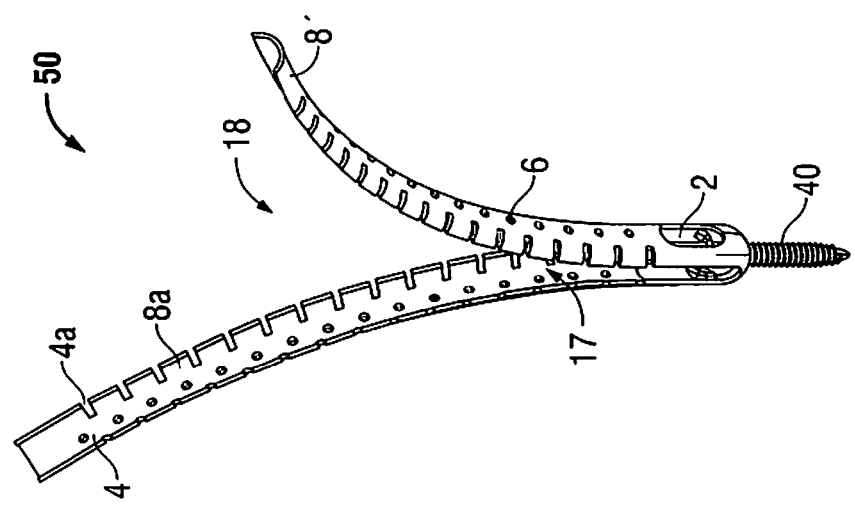
FIG. 6 is a perspective view of a flexible minimally invasive retractor and screw assembly according to another embodiment of the present disclosure.

Another embodiment of the flexible retractor is illustrated in FIGS. 6 and 7 and shown generally as retractor 50. Retractor 50 is similar to retractor 10, but includes a plurality of living hinges 4 along with their corresponding recesses 4a over the length of retractor 50. Each living hinge 4 is about 1-2 mm in height and each blade section 8a is about 5 mm in length.

In particular, each retractor blade 8' includes a plurality of blade sections 8a. Each blade section 8a is connected to an adjacent blade section 8a by a living hinge 4. Thus, the plurality of blade sections 8a and living hinges 4 define retractor blade 8'. As in the previous embodiment (FIG. 1), prior to spreading the flexible retractor each blade section 8' is substantially parallel to arm 13 to define slot 17 between retractor blades 8'.

When retractor blades 8' are urged radially outward from their initial or rest position towards their retracted position, the size of passage 18 increases. This increase in the size and area of passage 18 improves access to the surgical target site (i.e. near where the retractor is inserted into tissue), thereby increasing visibility of the target site, access for instruments, and access for surgical implants. As shown in FIG. 7, rod 3 is positioned in passage 18 after the surrounding tissue has been retracted using retractor 50. These advantages will be discussed in detail hereinafter. Additionally, the plurality of living hinges 4 greatly increases the adaptability of retractor 50 in comparison to retractor 10. While retractor blades 8 of retractor 10 (FIG. 1) generally bend at its single living hinge 4, the additional living hinges 4 present along retractor blades 8' of retractor 50 permit bending with increased flexibility at a number of positions along the length of each retractor blade 8'. Thus, retractor blades 8' will bend at the living hinge 4 that corresponds to the plane defined by the surface of the patient's body tissue. By using this construction, retractor 50 is usable in patient's having different tissue thicknesses between the vertebral body and the surface of their skin. In addition, since each retractor blade 8' has a plurality of living hinges 4 and blade sections 8a, it is not required for each retractor blade 8' to bend at the same point along the length of retractor 50, thereby accommodating variances in the depth that retractor 50 is inserted. For example, one retractor blade 8' may bend at its fourth living hinge 4, while the other retractor blade 8' may bend at its sixth living hinge 4, thereby accommodating variances in tissue thickness and orientation of retractor 50.

It is contemplated that any of the previously disclosed retractors may be formed of a bendable resilient material such that when external spreading forces (i.e. from a Gelpi retractor or the physician's hands) are removed, the retractor blades will return towards their initial position (e.g., substantially parallel to the centerline). It is also contemplated that any of the previously disclosed retractors may be formed of a bendable non-resilient material such that when the external spreading forces are removed, the retractor blades resist returning to their initial position and remain in the retracted position. All of retractors 10, 10' and 50 may be of any length suitable to extend out of the body with the retractor in place and the corresponding screw implanted. It is contemplated that the retractor may be about 6 inches long and may be readily adjusted to a desired length by removing excess material using scissors or a knife. In addition, the retractor may have an inner diameter that is approximately 16 mm and the retractor blades may be approximately 1 mm thick. Instrument holes 6 may be on 1 cm centerlines. Slot 17 is typically at least 5.5 mm wide, but will vary according to the size of the rod that will be inserted into the patient. The flexible retractor may be formed from any suitable biocompatible material having the desired physical properties. That is, retractor 10 is formed of a biocompatible, sterilizable material in a suitable configuration and thickness so as to be sufficiently rigid to be held on the screw when desired during insertion and a surgical procedure and to provide retraction of tissue, and yet is sufficiently bendable to be spread apart to provide retraction during surgery and sufficiently flexible to be forcibly removed from the screw as necessary and appropriate. It is contemplated that retractor 10 may be formed from polymers such as polypropylene, polyethylene, or polycarbonate, silicone, polyetheretherketone ("PEEK"), copolymers or blends of any of the foregoing, or another suitable material. Retractor blade 8 is bendable away from the centerline of retractor 10 in response to applied forces, wherein retractor blade 8 bends at living hinge 4 (or in the lower regions of the retractor if no living hinge is included). Bending retractor blade 8 away from the centerline (i.e. radially outwards) creates a larger opening through retractor 10 and also acts to retract the surrounding tissue at the selected surgical site.

Figure 23:
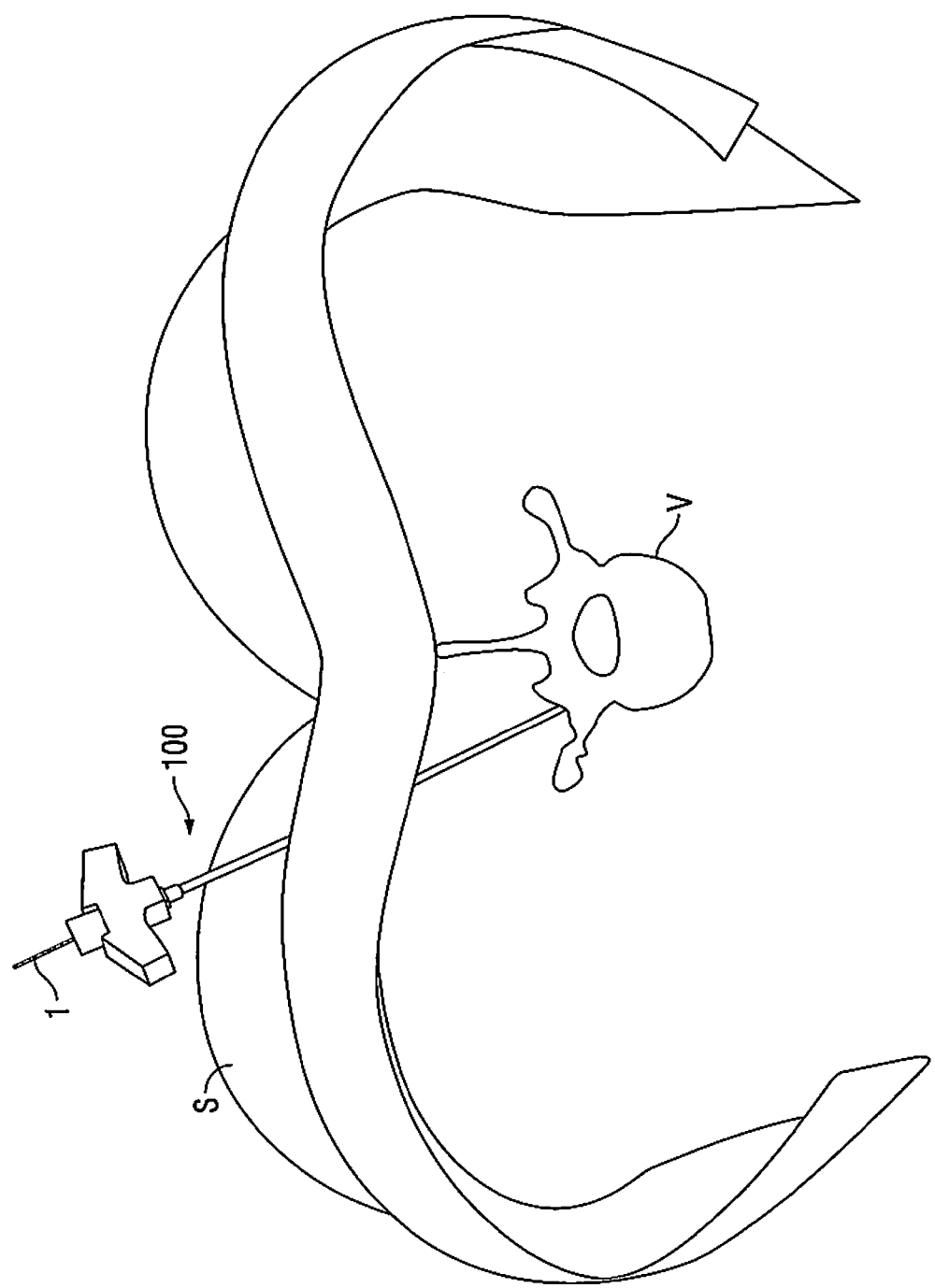
FIG. 23 is a front cross-sectional view of the body of FIG. 22 illustrating insertion of a guide wire through the bone biopsy needle.

Other components of the presently disclosed system will now be discussed with reference to FIGS. 8-19. In FIG. 8, a bone biopsy needle (e.g. a Jamshidi needle) 100 is illustrated. Needle 100 includes a handle 102 disposed at a proximal end of needle 100, an elongate tubular member 104 extending distally from handle 102, and a stylet 106. Stylet 106 has a sharpened distal tip 108 that is adapted for penetrating tissue, including bone. In addition, tubular member 104 has a lumen extending from its proximal end to its distal end for receiving stylet 106 therethrough. Stylet 106 is releasably attached to handle 102 such that it may removed once the target site has been pierced by distal tip 108. After stylet 106 is removed, a guidewire 1 (FIG. 23) may be inserted through tubular member 104 and secured or attached at the target site using known techniques.

Figure 24:
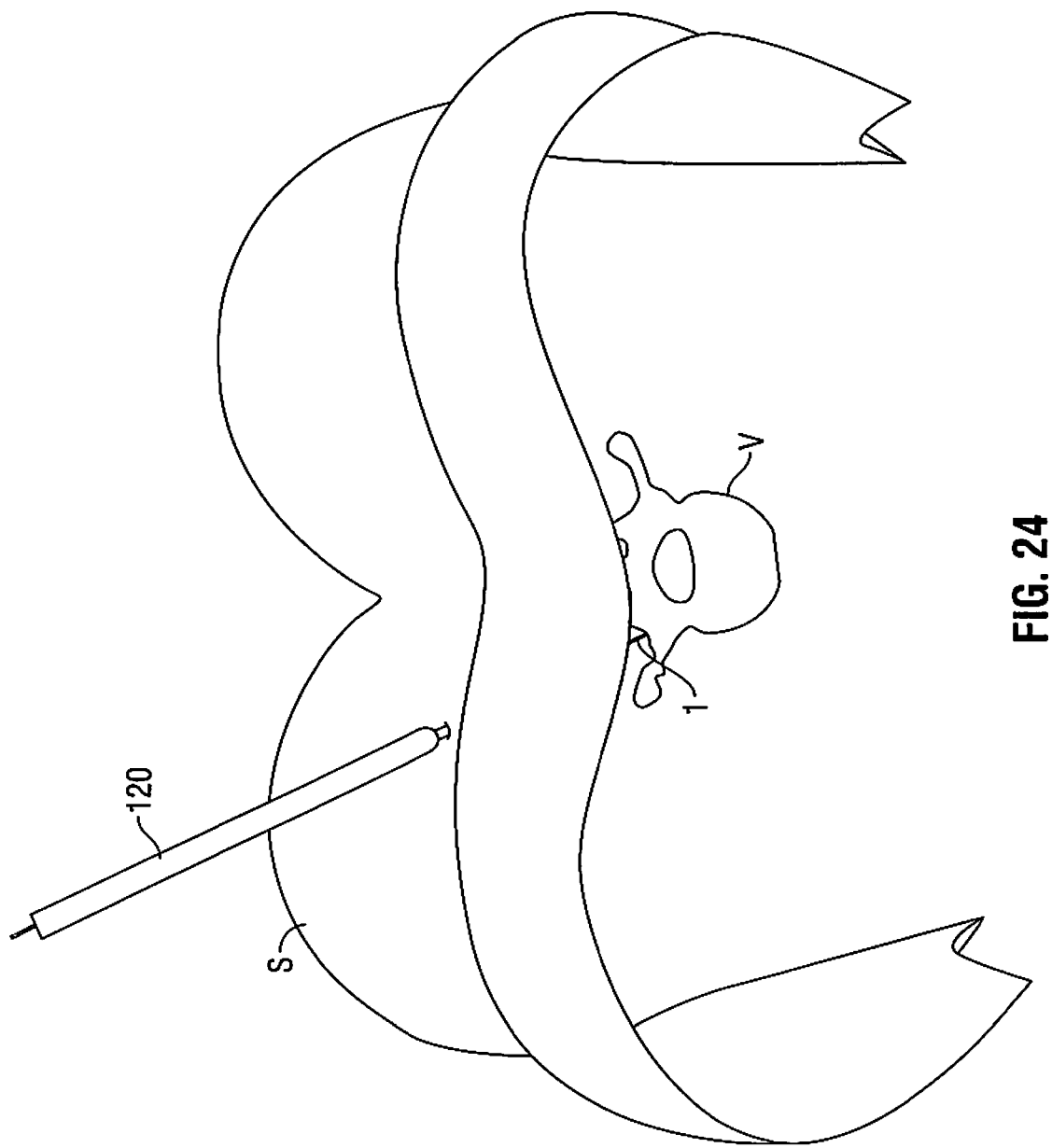
FIG. 24 is a front cross-sectional view of the body of FIG. 23 illustrating tissue separation using the cannulated scalpel of FIG. 9.

Referring now to FIG. 9, a cannulated scalpel 120 is illustrated. Scalpel 120 includes a housing 125 having a blade 126 disposed therein. Blade 126 has a sharpened distal end 124 for separating tissue. The width of the scalpel is selected to create an incision appropriately dimensioned to permit facile introduction of retractor 10, dilator 400 with retractor 10, or instrument inserter 500 (depending upon the surgical approach selected by the surgeon) over the guidewire as described below. In addition, distal end 124 includes an opening 124a that cooperates with an opening 128 located at proximal end 122 and defines a channel through scalpel 120 for slidably receiving guidewire 1 (FIG. 24) therethrough.

Figure 9A:
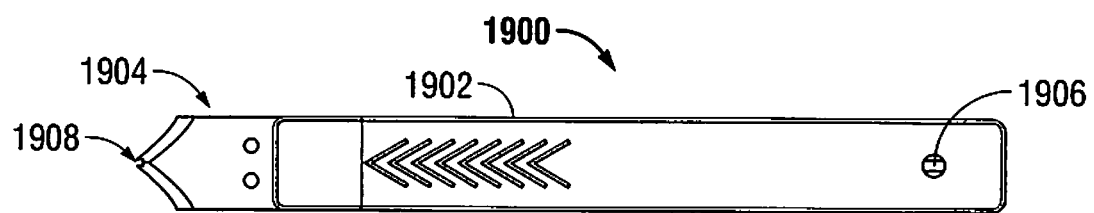
FIG. 9A is a top view of a cannulated scalpel according to an alternate embodiment of the present disclosure.
Figure 9B:
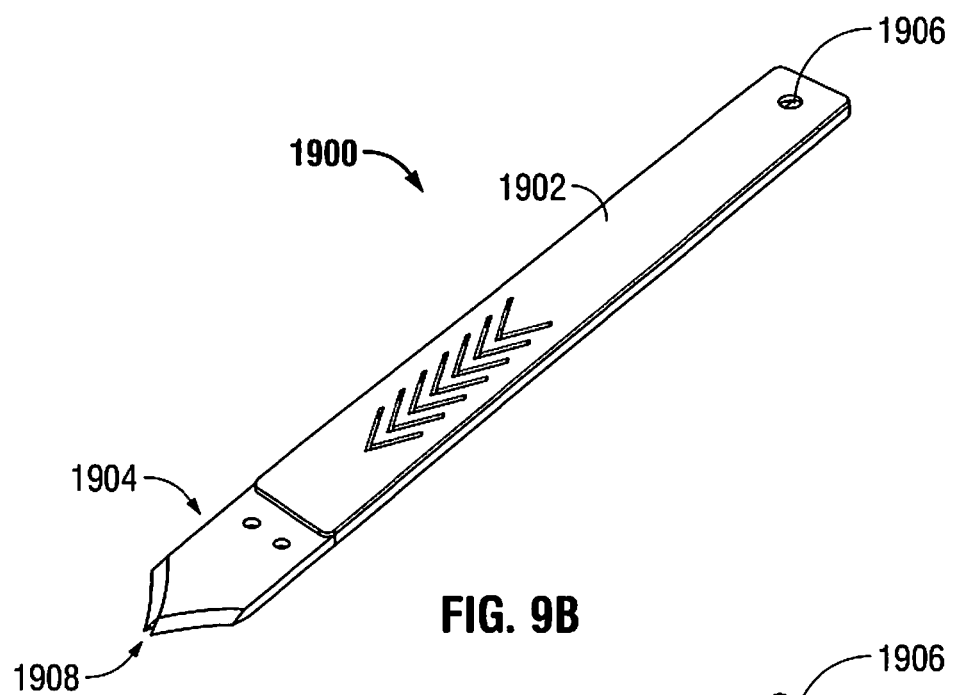
FIG. 9B is a top perspective view of the cannulated scalpel of FIG. 9A.
Figure 9C:
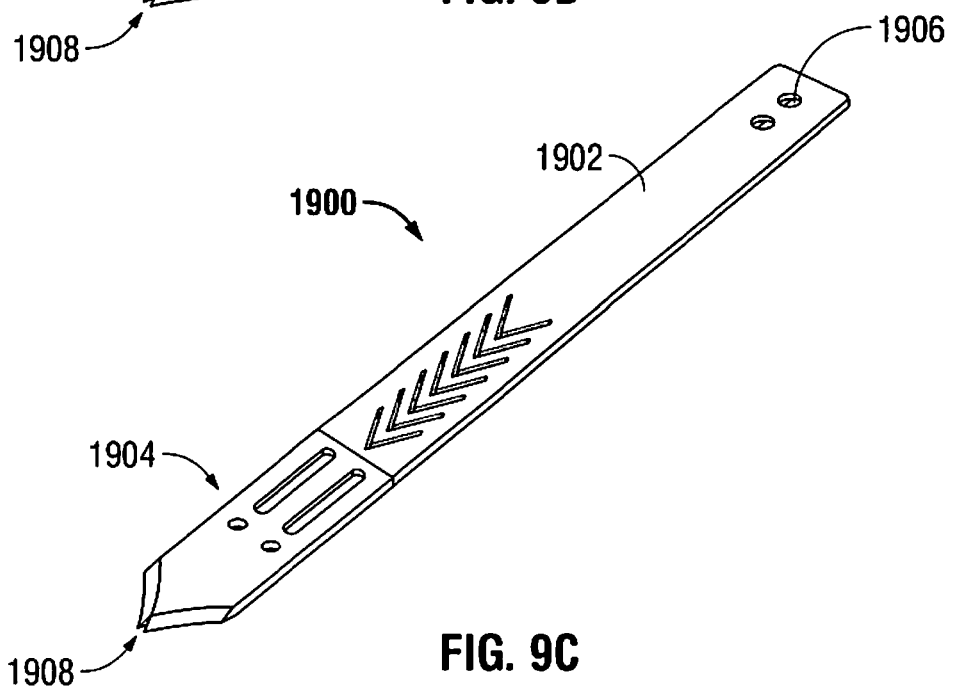
FIG. 9C is a bottom perspective view of the cannulated scalpel of FIG. 9A.
Figure 9D:
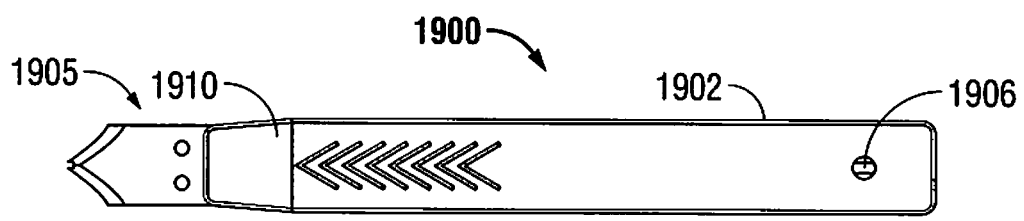
FIG. 9D is top view of a cannulated scalpel according to an alternate embodiment of the present disclosure.
Figure 9E:
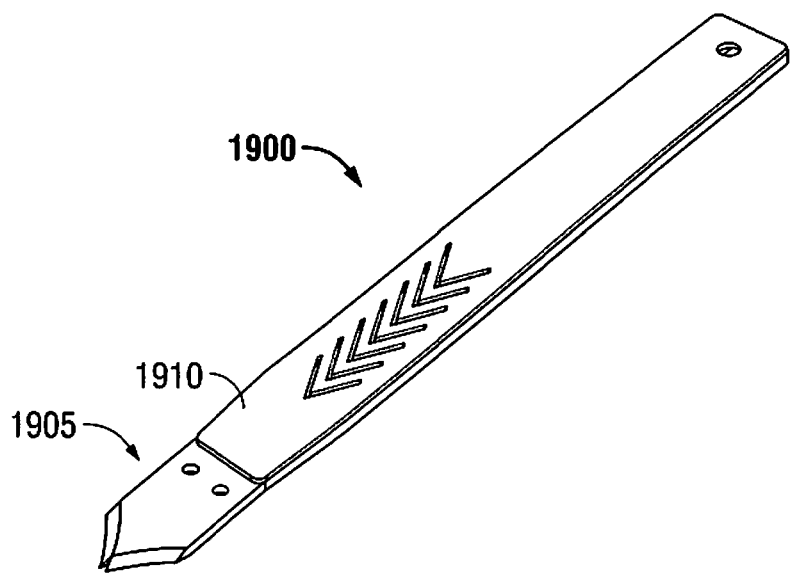
FIG. 9E is a top perspective view of the scalpel of FIG. 9D.
Figure 9F:
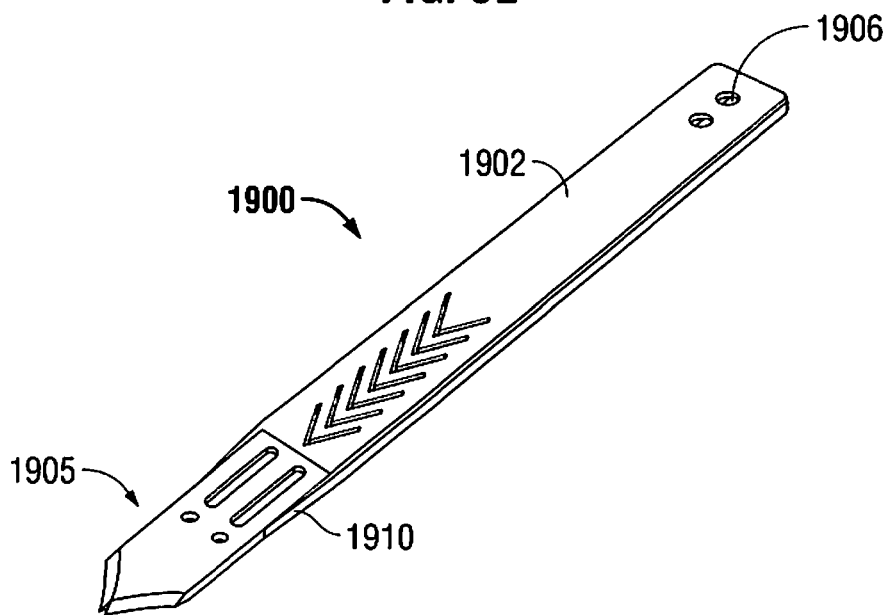
FIG. 9F is a bottom perspective view of the scalpel of FIG. 9D.

FIGS. 9A-9C illustrate an alternate embodiment of a cannulated scalpel 1900. The structure and operation of scalpel 1900 is substantially similar to the structure and operation of cannulated scalpel 120. Cannulated scalpel 1900, however, includes a handle 1902 molded onto blade 1904. Handle 1902 includes channel, passage, or lumen 1906 extending therethrough for receiving a guidewire (See FIG. 24). Lumen 1906 communicates an opening 1908 located on the distal end of blade 1904 with an opening (not shown) positioned on the proximal end of handle 1902. Handle 1902 may be made of any suitable moldable material such as a polymer. Blade 1904 has a sharpened distal end 1924 having an arcuate surface. In an alternative embodiment, handle 1902 has a tapered portion 1910 located at a distal portion thereof, as illustrated in FIGS. 9D-9F. In this embodiment, blade 1905 is narrower than blade 1904.

Figure 9G:
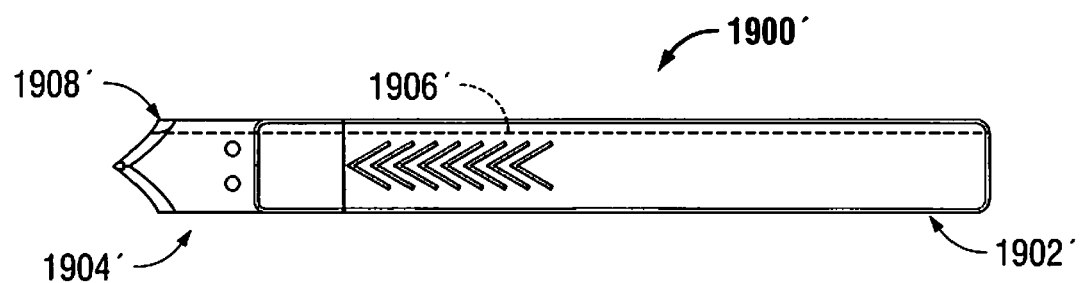
FIG. 9G is a top view of another embodiment of a cannulated scalpel with an offset lumen.
Figure 9H:
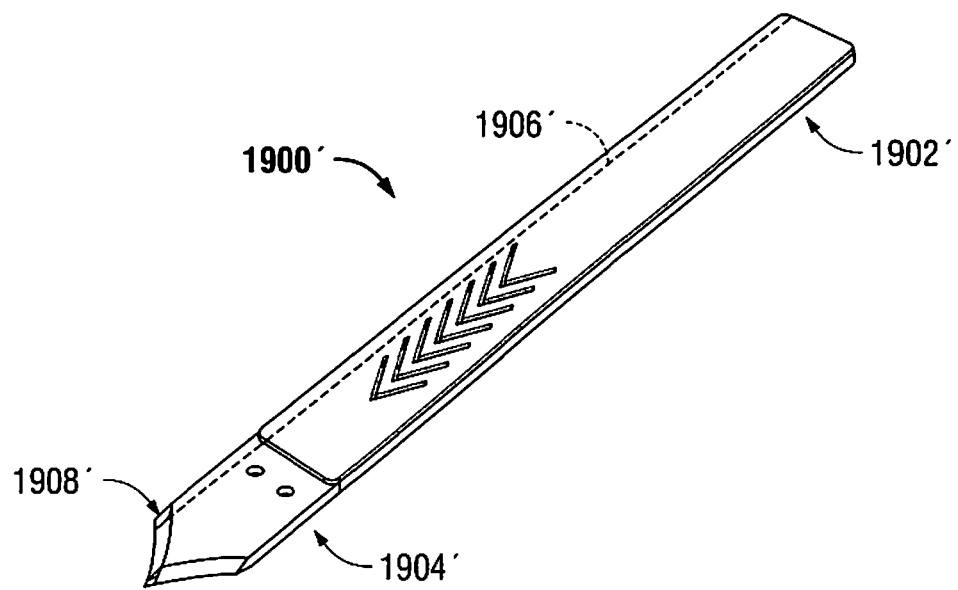
FIG. 9H is a perspective view of the cannulated scalpel of FIG. 9G.

FIGS. 9G and 9H show a further alternative embodiment of scalpel 1900'. Scalpel 1900' is substantially similar to scalpel 1900, but scalpel 1900' has a laterally offset lumen 1906' extending therethrough. Lumen 1906' is in communication with a distal opening 1908' located on a lateral edge of blade 1904' and with a proximal opening (not shown) positioned on a lateral edge of handle 1902'. In operation, scalpel 1900' facilitates cutting tissue between vertebral bodies. Initially, a surgeon places pedicle screws over a guidewire and directs the pedicle screws toward vertebral bodies. Once the pedicle screws are attached to the vertebral bodies, the surgeon guides the scalpel 1900' to a first pedicle screw by positioning lumen 1906' over the guidewire. Motion of the scalpel 1900' toward the first pedicle screw cuts through tissue, creating an incision that is oriented toward the second pedicle screw. The surgeon then removes scalpel 1900' from the guidewire, reverses the orientation of scalpel 1900', and places lumen 1906' over the guidewire leading to the second pedicle screw. Motion of scalpel 1900' toward the second pedicle screw cuts through tissue, creating an incision that is oriented toward the first pedicle screw.

Figure 10:
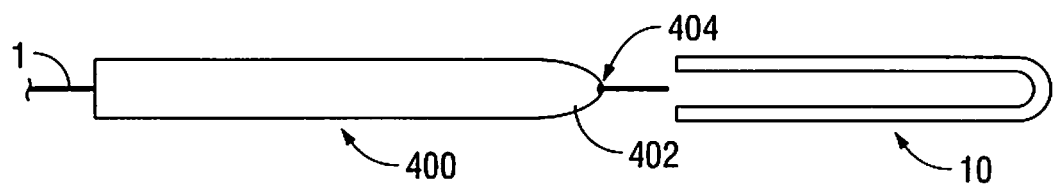
FIG. 10 is a side plan view of a dilator and retractor according to an embodiment of the present disclosure.

FIG. 10 shows a dilator 400 configured and dimensioned to be received through a retractor 10 with distal atraumatic blunt tip 402 protruding through opening 7 in retractor 10. Dilator 400 includes a longitudinal passage therethrough having a distal opening 404 for receiving guidewire 1 therethrough. Alternatively, it is contemplated that rather than a retractor, dilator 400 may be used together with a cannula (not shown). In either case, the atraumatic tip of the dilator extending through opening 7 of retractor 10 atraumatically spreads tissue so that the retractor may be inserted through the tissue to the bone.

Figure 10A:
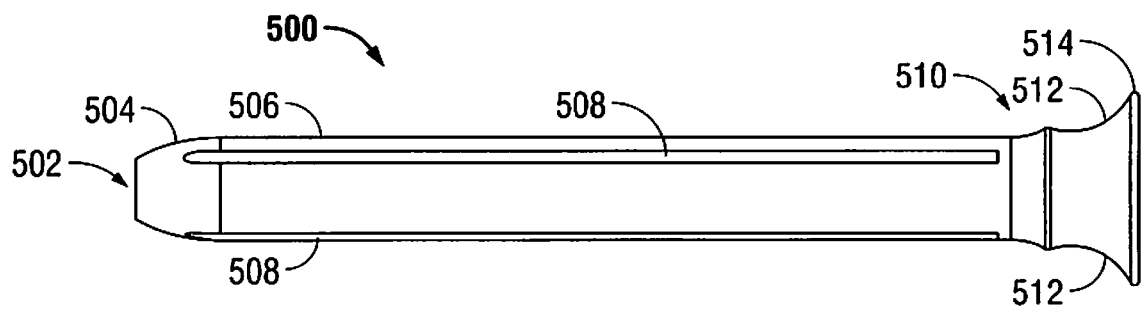
FIG. 10A is a side plan view of an instrument introducer according to an embodiment of the present disclosure.

As an alternative or in addition to using a dilator to inspect the target site, the surgeon may choose to use an instrument inserter to atraumatically introduce an awl, drill, bone tap or the like to prepare the implant site to receive the bone screw. FIG. 10A illustrates an instrument introducer 500. Instrument introducer 500 has an open distal end 502 configured and dimensioned to permit an appropriate instrument (e.g., awl, drill or bone tap) to pass therethrough. The instrument is cannulated to receive the guidewire. Adjacent open distal end 502 is a dilating tip surface 504, a generally atraumatic dilating tip. The atraumatic tip transitions to a substantially straight introducer shaft 506, which may include longitudinal grooves 508 to facilitate insertion through tissue. Proximal end 510 is trumpet shaped to facilitate one handed removal. That is, with a finger disposed on each side of the introducer in recesses 512 distal to lip 514, the introducer may readily be pulled out of tissue. Introducer 500 is hollow through the center to receive a suitable surgical instrument. As stated, a surgeon may desire to use an awl, drill or tap over the guidewire to penetrate the cortical bone and prepare the target site for screw implantation. In such a case, introducer 500 may be useful to insert the instrument and shield the surrounding tissue from the instrument and vice versa. Indeed, the surface of such an instrument can be highly traumatic to surrounding soft tissue, and the drill or tap can become fouled with soft tissue that may inhibit obtaining the desired results in bone if the instrument and soft tissue are not shielded from each other during instrument insertion. While introduction of the instrument may be performed through a small incision without a guidewire, in this method the instrument is cannulated and the instrument and introducer are led through the tissue over the guidewire. Thus, with the desired instrument disposed within the introducer 500 and the guidewire inserted through the cannulated instrument, the introducer and instrument are inserted over the guidewire through the tissue by gently spreading the tissue as the introducer is advanced into and through the tissue until the tip of the introducer 500 reaches the target bone site. At this point the instrument may be advanced out of the distal end of the introducer to engage the bone and perform its intended function. Retractor 10 may be on the order of about 15 mm to about 20 mm in outer diameter in order to accommodate a screw therein. In comparison, the instrument introducer 500 may be smaller in diameter, on the order of about 10 mm to 12 mm in outer diameter depending upon the instrument to be introduced therethrough.

Figure 25:
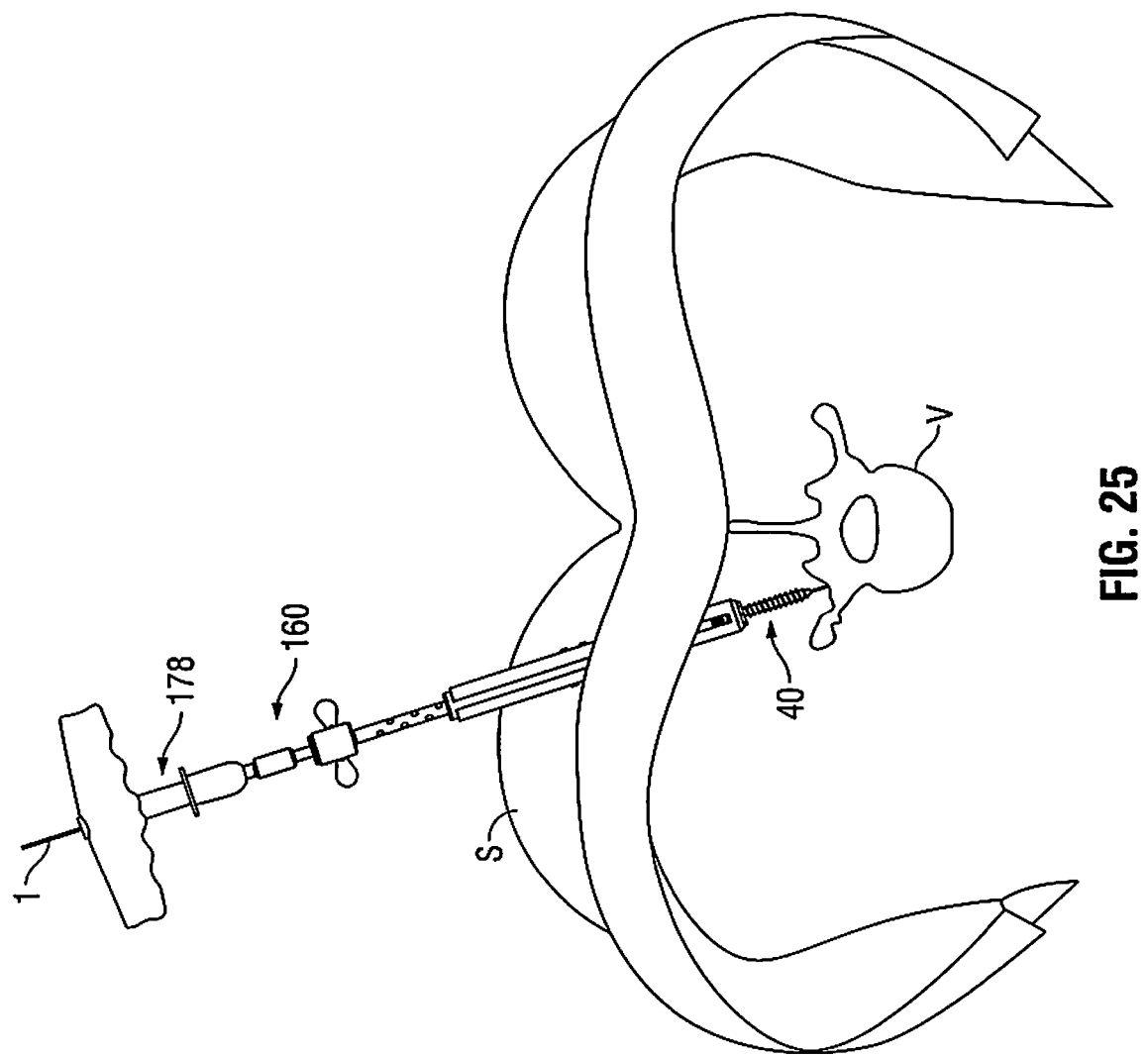
FIG. 25 is a front cross-sectional view of the body of FIG. 23 illustrating insertion of the screw insertion assembly of FIG. 14.

In FIGS. 11, 11A and 11B, a cannulated bone tap 140 is shown. Bone tap 140 includes an elongated body 142 having a proximal end 146 and a distal end 144. Distal end 144 includes a helical thread 145 for forming threads in a hole that is formed in a bony structure (e.g., a vertebral body). Proximal end 146 includes a tool engagement region 147 that is adapted for cooperating with a driving or rotating tool 178 (FIG. 25) and forming the threads in the bony structure. Driving and rotating tools are well known in the art. In addition, proximal end 146 and distal end 144 cooperate to define a channel 148 extending through bone tap 140 such that bone tap 140 may be slid along guidewire 1. Bone tap 140 is available in a number of different sizes in a range of about 5.5 mm to about 7.5 mm. Alternatively, other bone taps may be used that match the size of the screw threads of the screw that will be implanted into bone. It is also contemplated that one or more awls, cannulated drills or the like may be used by the surgeon, all of which may be used with an instrument introducer.

Figure 12:
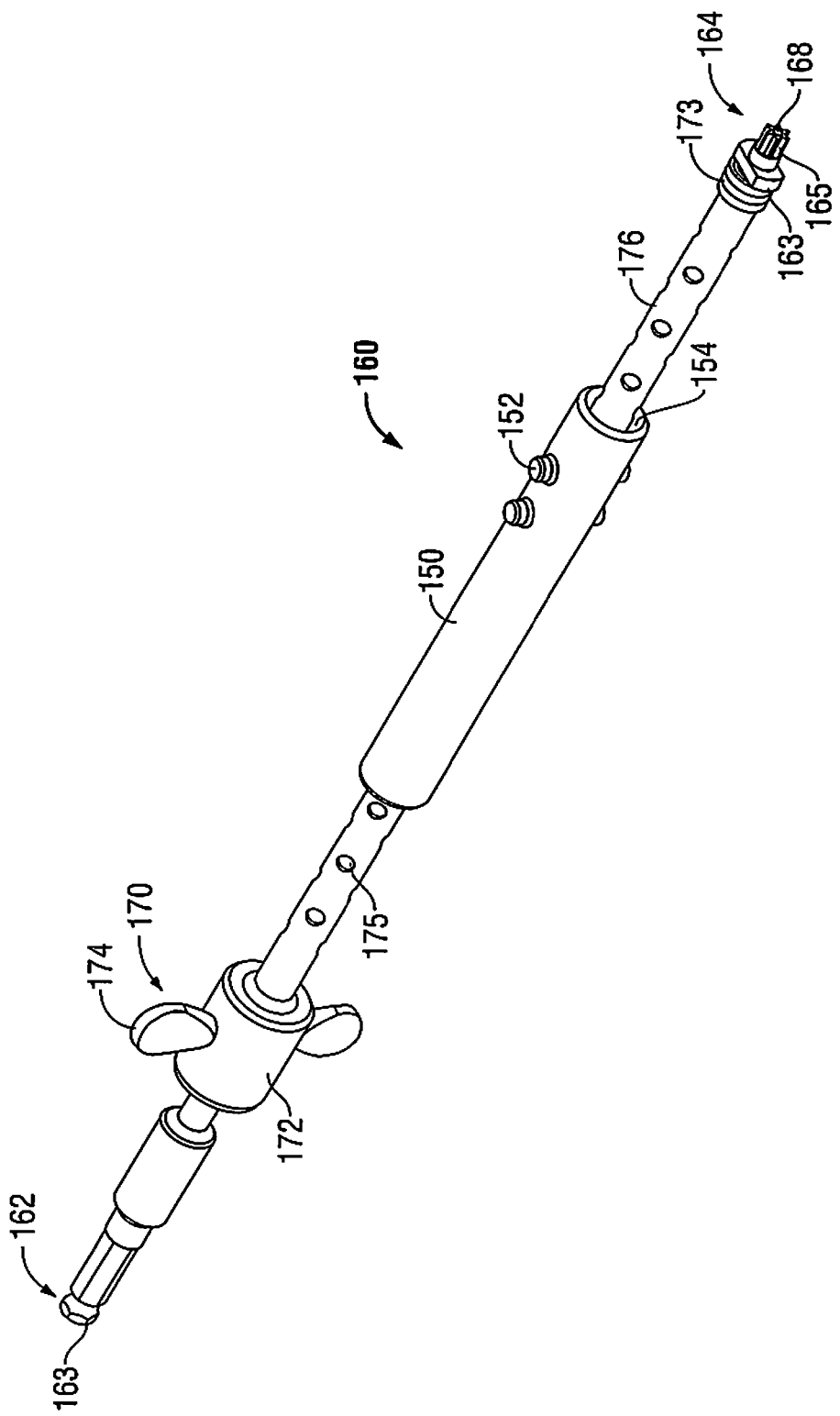
FIG. 12 is a perspective view of a screw inserter having an anti-rotation sleeve according to an embodiment of the present disclosure.
Figure 13:
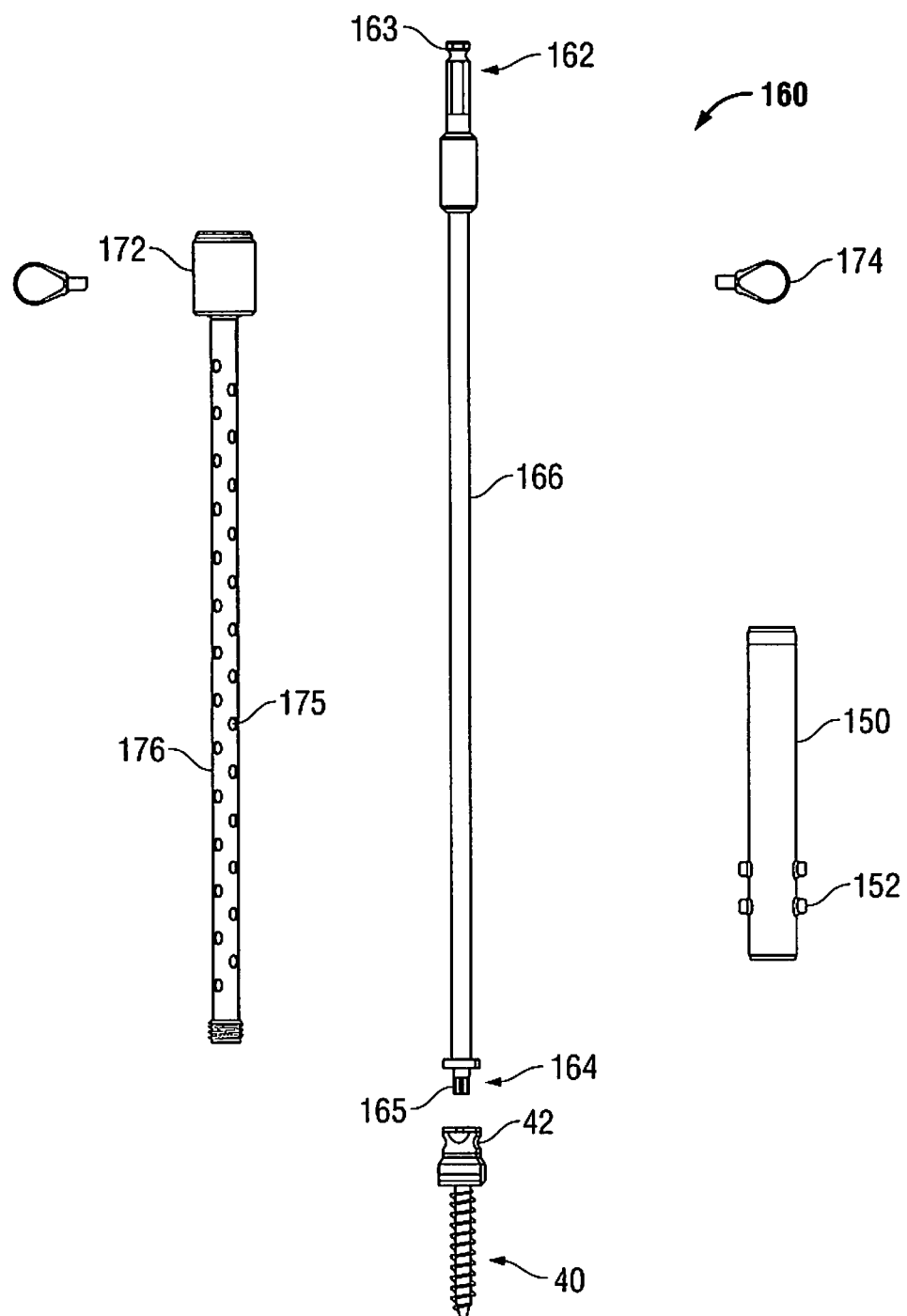
FIG. 13 is a side exploded view of the screw inserter of FIG. 12 shown with a spine screw.

A screw inserter 160 is illustrated in FIGS. 12 and 13. Screw inserter 160 includes an anti-rotation sleeve 150 and a housing 170. Housing 170 includes a body 172 having a pair of handles 174 extending therefrom. A tubular member 176 extends distally from body 172 and includes a plurality of holes 175. A shaft 166 (FIG. 13) is disposed through a lumen of tubular member 176 and is rotatable therein. A screw engaging structure 165 is disposed at a distal end 164 of shaft 166 is adapted and configured to releasably engage a head 42 of pedicle screw 40. In particular, screw inserter 160 includes a cross-member 164 and threads 173, which releasably connect the screw inserter 160 to screw 40. During assembly of screw inserter 160 and pedicle screw 40 (FIG. 25), screw engaging structure 165 is inserted into head 42 with cross-member 163 occupying rod receiving recess 44 and threads 173 engaging threads 45 of pedicle screw head 42. Handles 174 are used to rotate tubular member 176 and threads 173 to engage threads 173 with screw 40. This arrangement releasably secures pedicle screw 40 to screw inserter 160. When assembled with pedicle screw 40, rotation of shaft 166 also causes rotation of pedicle screw 40 without causing rotation of housing 170. Anti-rotation sleeve 150 is located along an outer surface of tubular member 176 and includes protruding pins or buttons 152.

Figure 14:
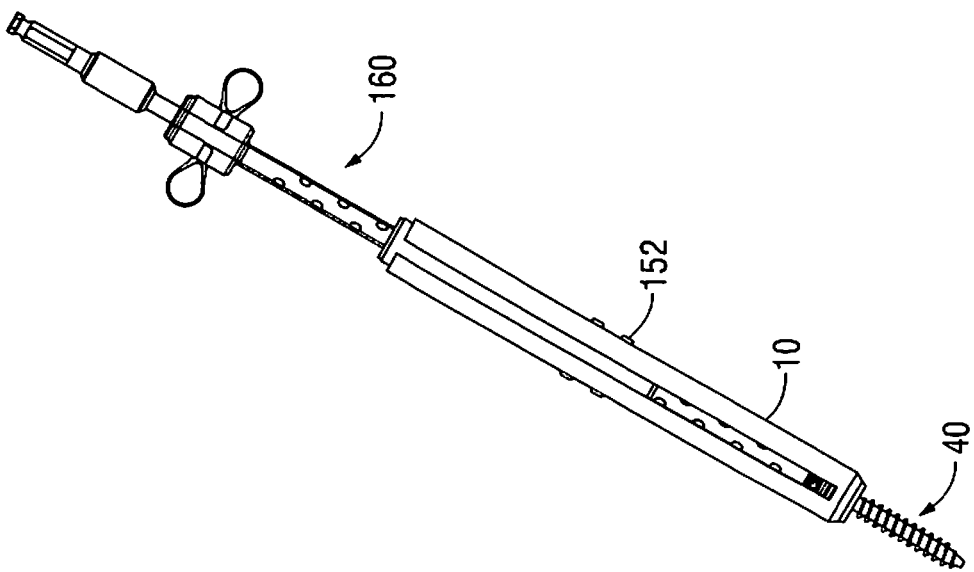
FIG. 14 is a side view of a screw insertion assembly including the screw inserter of FIG. 12, a flexible minimally invasive retractor, and a spine screw.

As best seen in FIG. 14, buttons 152 are configured and adapted to releasably engage instrument holes 6 of retractor 10. Although retractor 10 is illustrated in cooperation with screw inserter 160, screw inserter 160 is configured and adapted to cooperate with retractor 50. Buttons 152 of screw inserter 160 engage instrument holes 6. Because buttons 152 are mounted to anti-rotation sleeve 150, as shaft 166 is rotated to rotate screw 40 during implanting of the screw 40, retractor 10 remains stable and does not rotate. The ability to rotate screw 40 without rotating the retractor is important, as rotation of the retractor during implanting of the screw 40 could cause trauma to surrounding soft tissue. This arrangement permits insertion of pedicle screw 40 while minimizing displacement of the selected retractor from its desired location and orientation.

Figure 15:
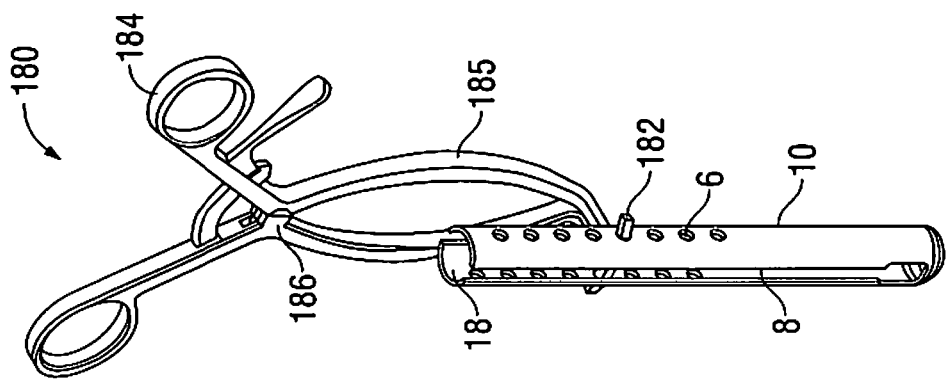
FIG. 15 is a perspective view of a retraction assembly including a flexible minimally invasive retractor and a Gelpi retractor.

A common spreader, or Gelpi retractor 180 is shown in FIG. 15 in cooperation with retractor 10. Gelpi retractor 180 includes a pair of curvate arms 185 that are pivotably connected at pivot point 186. A pair of finger rings 184 is located at a proximal end of Gelpi retractor 180 that permit the physician to move arms 185 selectively toward and away from each other. A finger 182 is located at a distal end of each arm 185 and is configured to releasably engage an instrument hole 6 in retractor 10. As shown, finger rings 184 are laterally offset from arms 185. Thus, pivotable movement of arms 185 urge retractor blades 8 towards and away from each other in response to movement of finger rings 184. Moving finger rings 184 toward each other pivots arms 185 away from each other and urge retractor blades 8 away from each other, thereby enlarging passage 18. Consequently, movement of finger rings 184 away from each other has the opposite effect. Gelpi retractor 180 is also configured and adapted to cooperate with retractor 50, 60, and 70.

Figure 16:
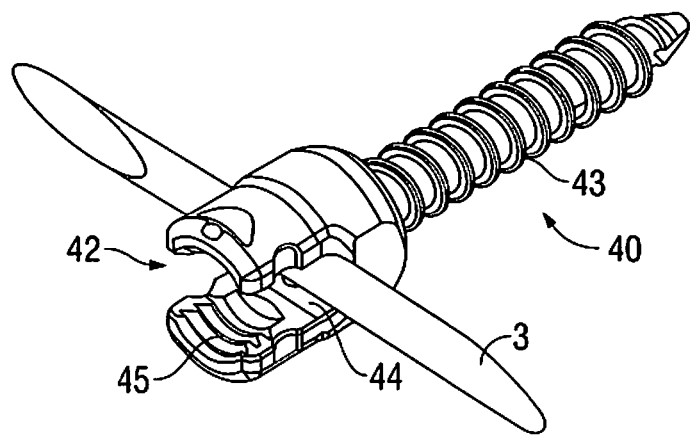
FIG. 16 is a perspective view of a cannulated screw with a rod positioned in a rod receiving passage.
Figure 16A:
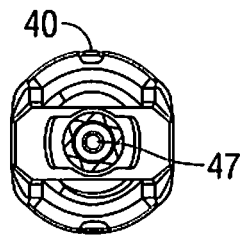
FIG. 16A is top view of the cannulated screw of FIG. 16.
Figure 16B:
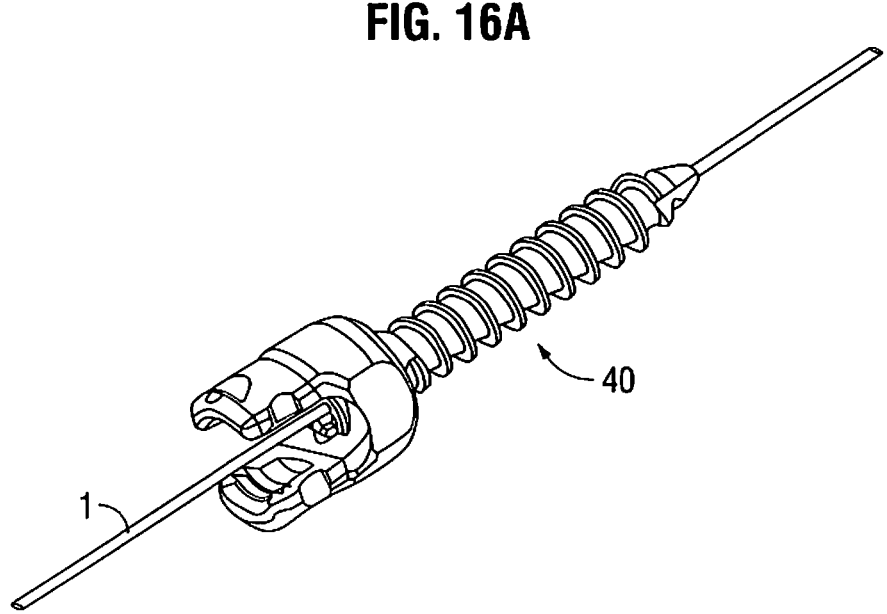
FIG. 16B is a perspective view of the cannulated screw of FIG. 16 illustrating an optional guidewire inserted therethrough.

FIGS. 16, 16A, and 16B illustrate a cannulated minimally invasive pedicle screw 40. Pedicle screw 40 includes a helical thread 43 that is sized and configured for insertion into a threaded hole created by bone tap 140. A head 42 includes a tool engaging portion that is adapted to cooperate with screw inserter 160 as previously discussed. A rod receiving passage 44 is formed in head 42. In addition, head 42 includes a threaded portion 45 that is adapted to removably attach to the screw inserter 160 and receive a setscrew (not shown). The setscrew compresses against rod 3 in passage 44 and frictionally engages rod 3 to hold it in a desired position. Set screws are well known in the art. A throughbore 47 extends between a proximal end and a distal end of pedicle screw 40 for receiving guidewire 1 therethrough (FIG. 16B).

Figure 17:
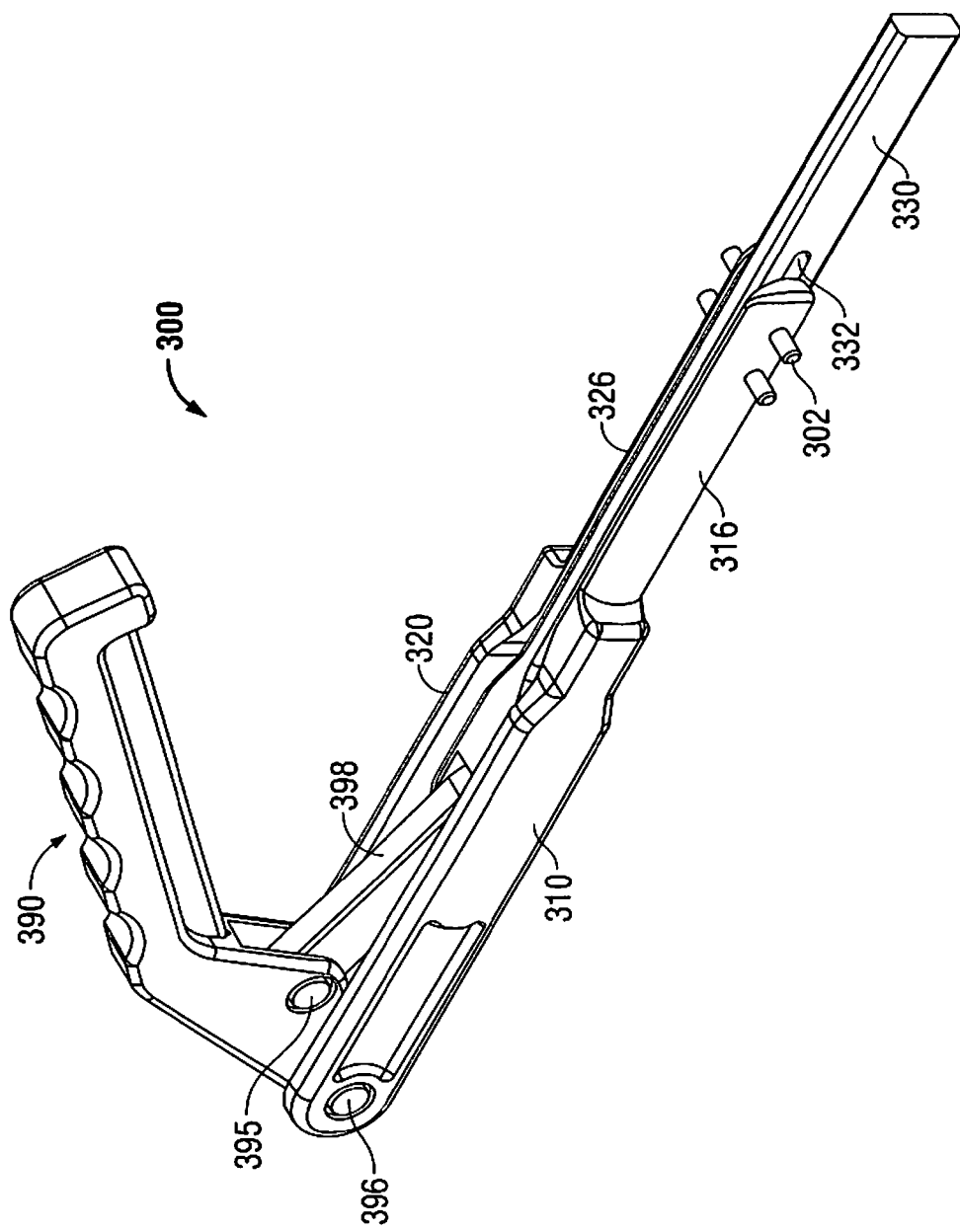
FIG. 17 is a perspective view of a retractor extractor instrument according to an embodiment of the present disclosure.
Figure 18:
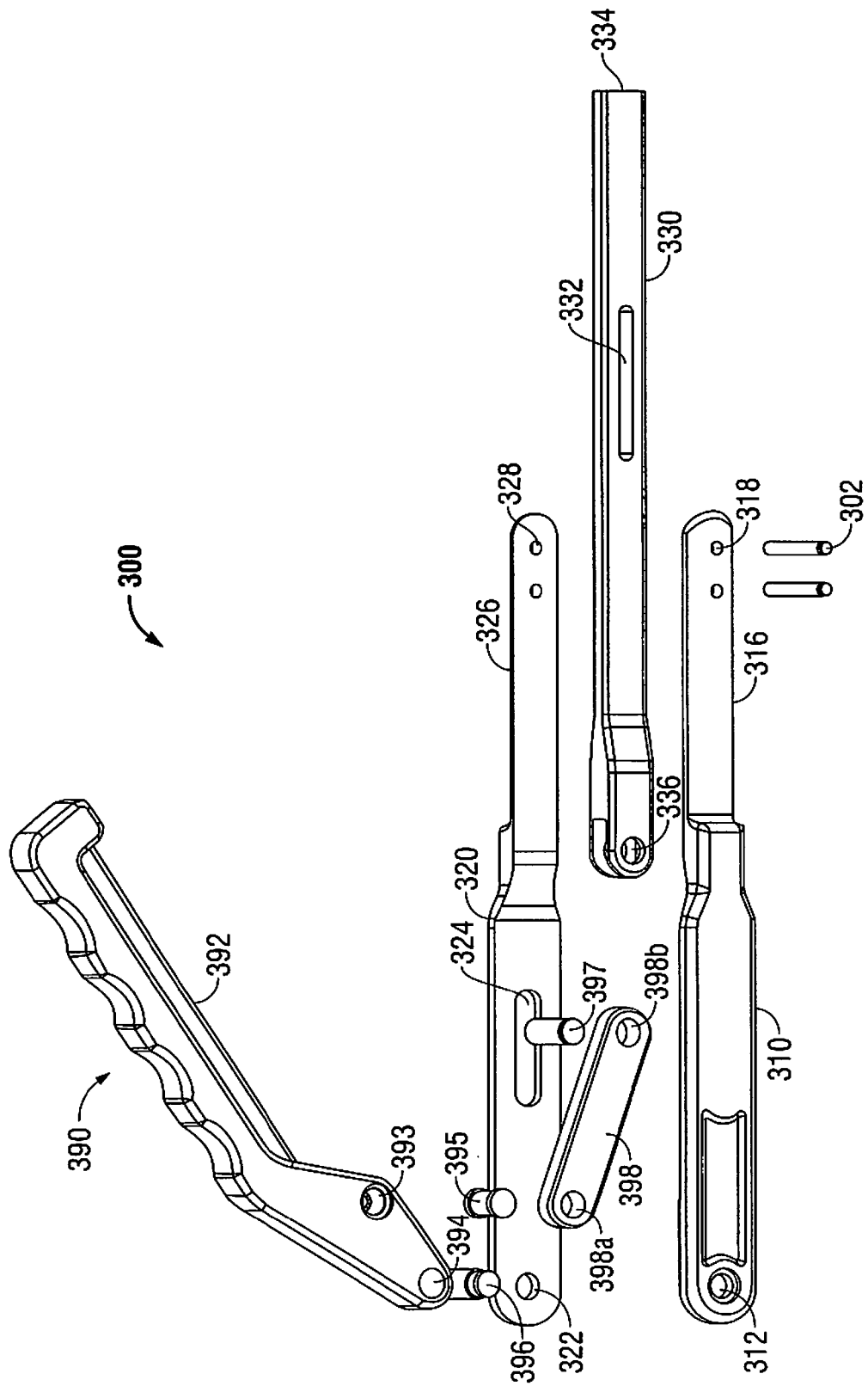
FIG. 18 is a perspective exploded view of the retractor extractor instrument of FIG. 17.
Figure 19:
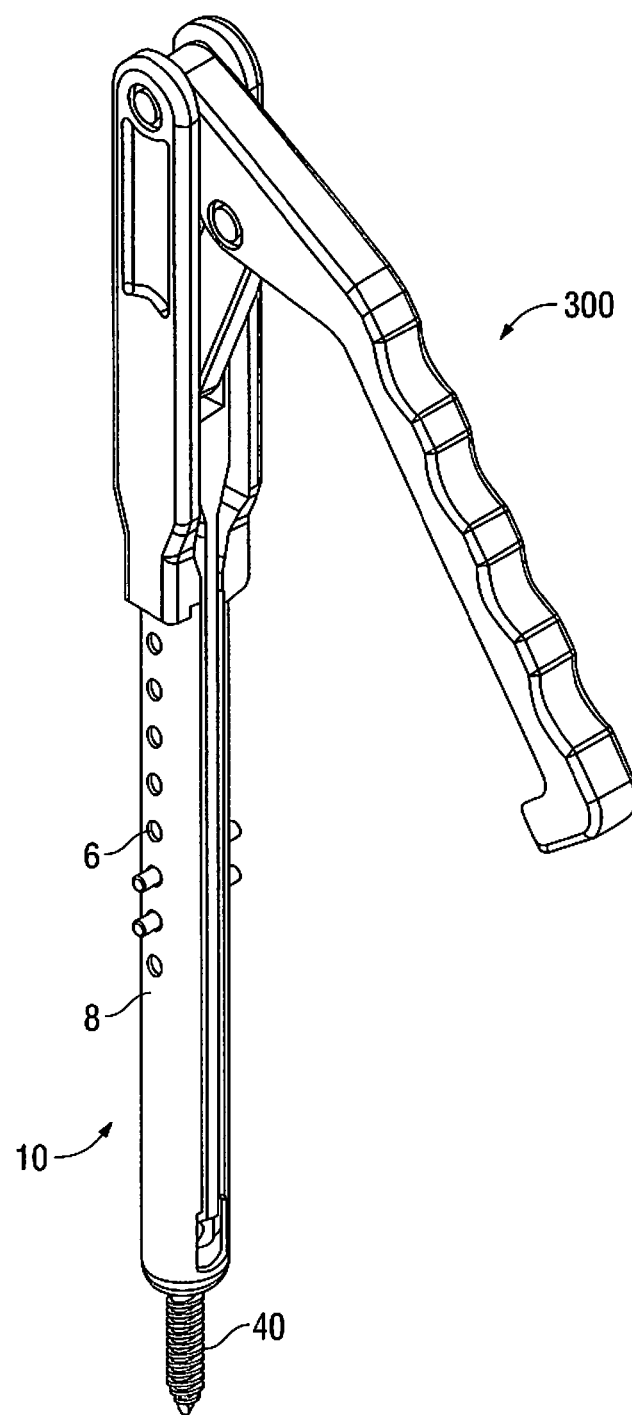
FIG. 19 is a perspective view of the retractor extractor instrument of FIG. 17 coupled to a minimally invasive retractor operatively associated with a spine screw.

A retractor extractor instrument 300 is illustrated in FIGS. 17-19. Retractor extractor 300 includes handle portion 390, arms 310 and 320, and extractor bar 330. Handle portion 390 includes a handle grip 392 having openings 393, 394 disposed at one end thereof. Pin 396 extends through opening 394 and pivotably couples handle portion 390 to arms 310, 320 by extending through holes 312, 322 of arms 310, 320. A pin 395 extends through opening 393 and pivotably couples handle portion 390 to pivot bar 398 through hole 398a. At an opposing end of pivot bar 398, hole 398b receives a pin 397. Pin 397 extends between arms 310, 320 and is slidably captured therebetween. In particular, pin 397 slides proximally and distally within a recess 324 of arm 320. Arm 310 has an identical recess that is not shown. Additionally, pin 397 extends through an opening 336 of extractor bar 330. Retractor bar 330 has a slot 330 that extends parallel to its longitudinal axis and slidably receives posts 302 therethrough. Posts 302 are attached to blade portions 316, 326 through openings 318, 328. Additionally, posts 302 are adapted to releasably engage instrument holes 6 of the previously disclosed retractors (FIG. 19). At a distal end of extractor bar 330, an optional extension tip 334 may engage the screw head or the set screw driving recess. Alternatively, the distal end of extractor bar 330 may be a flat end to bluntly engage head 42 of pedicle screw 40, a set screw or a rod disposed therein.

Pivoting handle grip 392 toward arms 310, 320 simultaneously moves extractor bar 330 distally (i.e. toward the screw) such that pins 302 on arms 310, 320 and distal blunt end 334 move apart relative to each other. This simultaneous relative movement between extractor bar 330 and pins 302 causes the refractor to separate from the pedicle screw at the relief regions without applying any appreciable downward forces on the implant or the patient.

Figure 33:
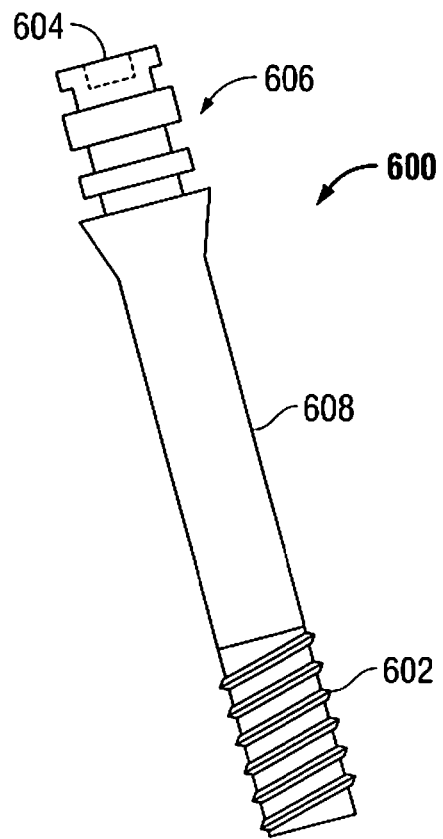
FIG. 33 is a side view of a temporary set screw with a quick connect feature in accordance with an embodiment of the present disclosure.

FIG. 33 is a side view of a specialized set screw 600 having a threaded distal tip 602 configured and dimensioned to engage screw head 42. Temporary set screw 600 has a proximal end with a screwdriver engaging feature 604 (shown as a recess) and a quick connect stem 606. The length of shaft 608 is selected so that the quick connect feature 604 extends out of and above the incision to when threaded tip 602 is engaged with the head of an implanted pedicle screw.

Use of the flexible retractor and related instruments to implant pedicle screws will now be described. In a first method, retractor 10 is assembled with pedicle screw 40 and screw inserter 160 as shown in FIG. 14. The assembled apparatus is inserted into an incision through the patient's skin and muscle/fat tissue such that pedicle screw 40 is subsequently threaded into a vertebral body V under direct visualization. Alternatively, retractor 50 may be assembled with pedicle screw 40 and screw inserter 160 and the assembled apparatus is inserted into an incision through the patient's skin and muscle/fat tissue such that pedicle screw 40 may be threaded into a vertebral body.

Referring now to FIGS. 22-26, an alternate, less invasive technique is illustrated. Biopsy needle 100 is inserted through skin S of the patient until its distal end contacts the selected point on vertebral body V. Biopsy needle 100 may be inserted in a known manner, such as percutaneously under fluoroscopic imaging, or under optical or magnetic image guidance (such as the STEALTH® system available from Medtronic Sofamor Danek). A small puncture in the vertebral body V is made using sharpened distal tip 108 (FIG. 8). After pin 106 is removed from biopsy needle 100, guidewire 1 is inserted through biopsy needle 100 and affixed to vertebral body V. Guidewire 1 now is in position to direct further instruments and devices to the selected location on vertebral body V. Alternately, guidewire 1 may be inserted into vertebral body V without first using biopsy needle 100. The size of the working area may be increased at the physician's discretion. In order to permit inspection of the position of guidewire 1 prior to insertion of a spine screw, a dilator 400 and optional retractor 10 may be inserted over the guidewire by inserting guidewire 1 through dilator opening 404 (FIG. 10) with the dilator inserted through retractor 10. Once the dilator tip with retractor is inserted to the target site, the dilator may be removed and placement of the guidewire may be inspected through the retractor. If the surgeon is satisfied with the placement of guidewire 1, then the procedure may continue through the retractor or the retractor may be removed and another inserted with a screw. If, on the other hand, the surgeon desires to change the guidewire location, another guidewire may be placed through the retractor, such as by inserting bone biopsy needle 100 through the retractor to a different placement in the bone and inserting a new guidewire at the new location. The former guidewire may then be removed. If desired, the physician may pre-drill a threaded bore in vertebral body V using bone tap 140 inserted along guidewire 1 to prepare the bore. Instrument introducer 500 may be used for this purpose.

Figure 20:
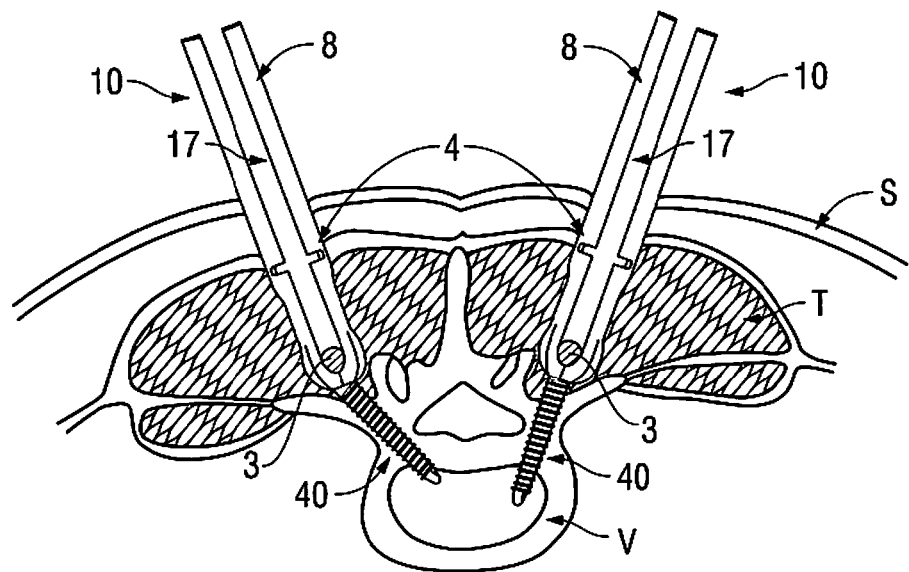
FIG. 20 is a front cross-sectional view of a vertebral body with a pair of flexible minimally invasive retractors attached thereto with screws, showing the flexible retractor blades in their initial position and rods positioned in the passages of the minimally invasive retractors.
Figure 21:
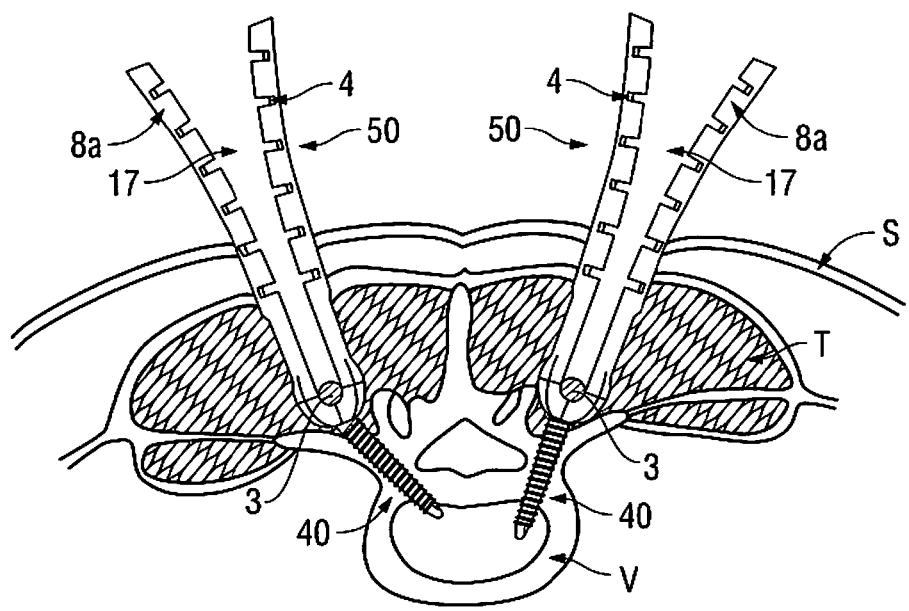
FIG. 21 is a front cross-sectional view of the vertebral body with a pair of flexible minimally invasive retractors attached thereto with screws, illustrating the flexible retractor blades in a second position and the rods positioned in the passages of the minimally invasive retractors.
Figure 22:
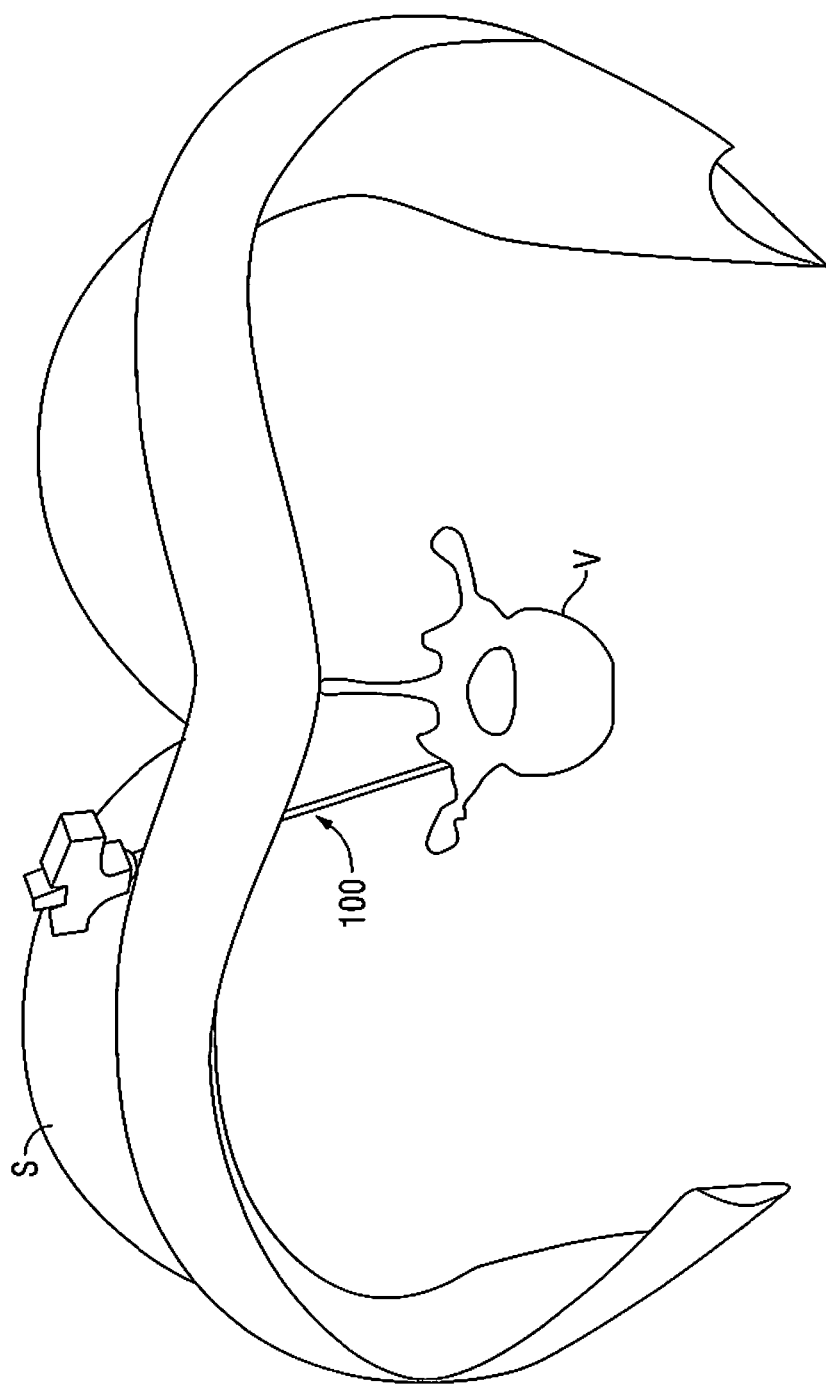
FIG. 22 is a front cross-sectional view of a body illustrating insertion of the bone biopsy needle of FIG. 8 into a vertebral body.
Figure 26:
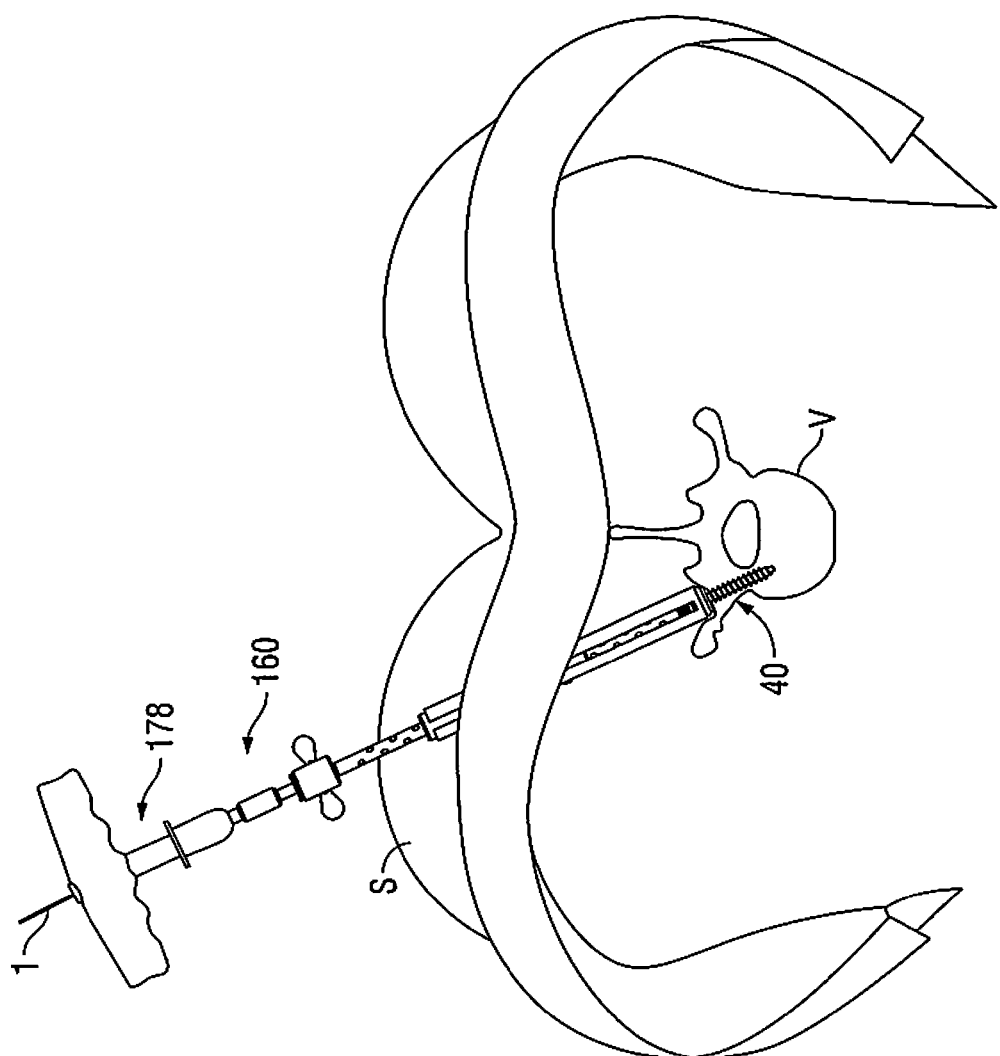
FIG. 26 is a front cross-sectional view of the body of FIG. 23 with the vertebral body illustrating the screw of the screw insertion assembly inserted into the vertebral body.

Once the target site is ready to accept a pedicle screw and retractor, an assembly including pedicle screw 40, retractor 10, and screw inserter 160 is slid along guidewire 1 to reach the target site. Using optional driving handle 178 (FIG. 25), the physician rotates screw inserter 160 to drive pedicle screw 40 into vertebral body V (FIG. 26). After pedicle screw 40 is secured in vertebral body V, screw inserter 160 is removed and retractor 10 remains in place secured by the screw which has been inserted into bone. This technique is also adapted for use with retractor 50. The result of the attached retractors is the same as shown in FIGS. 20 and 21, albeit without the rod in place as there illustrated.

In one method of the present application, rather than spread the flexible arms in a medial-lateral direction at this point in the procedure as described in U.S. patent application Ser. No. 11/528,223, the flexible retractors are re-oriented in a cephalad-caudad orientation, i.e. rotated approximately 90.degree. from the position illustrated in FIGS. 20-21. For reasons which will be explained below, at least one polyaxial screw head body for receiving a rod in also reoriented 90.degree., such that the rod receiving channel of the screw is oriented in the medial-lateral direction. With the screw-based retractors of two adjacent screws on the same side of the spine oriented in the cephalad-caudad direction, a first spreading instrument, such as a Gelpi retractor, is used to spread the two independent flexible retractors apart from one another. That is, rather than spreading the arms of one flexible retractor apart from each other, at this point two separate retractors are spread apart from each other using the Gelpi retractor. Either before or after the flexible retractors are spread apart in the cephalad-caudad orientation and direction, an incision is made between the screws. Thus, the flexible screw-based retractors define the cephalad-caudad boundaries of an incision made between two screws implanted into the pedicles of adjacent vertebral segment on the same side of the spine.

Figure 27:
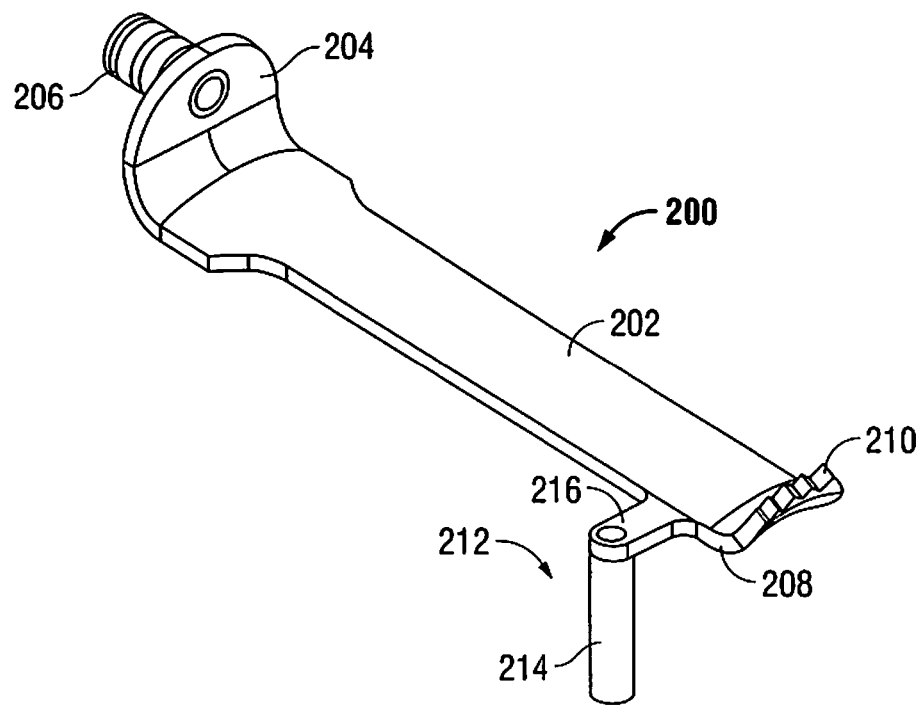
FIG. 27 is a perspective view of a substantially rigid retractor designed to be mounted in the rod-receiving channel of a screw.
Figure 27A:
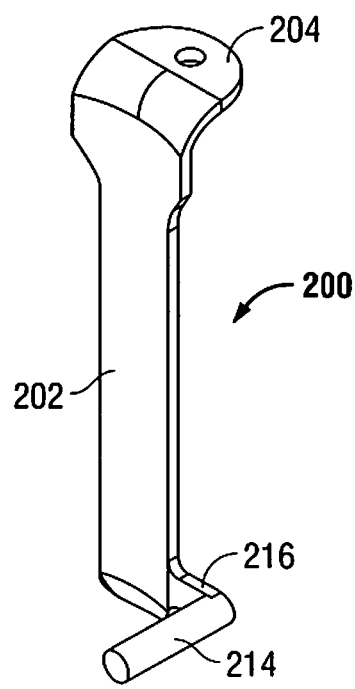
FIG. 27A is a perspective view of the retractor blade of FIG. 27.
Figure 27B:
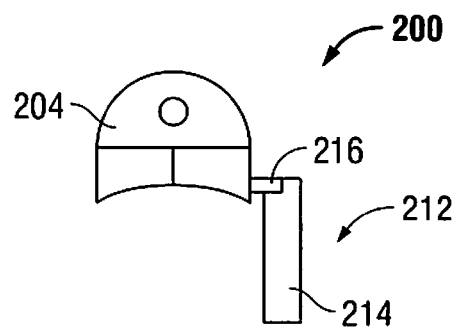
FIG. 27B is a top view of the retractor blade of FIG. 27.
Figure 27D:
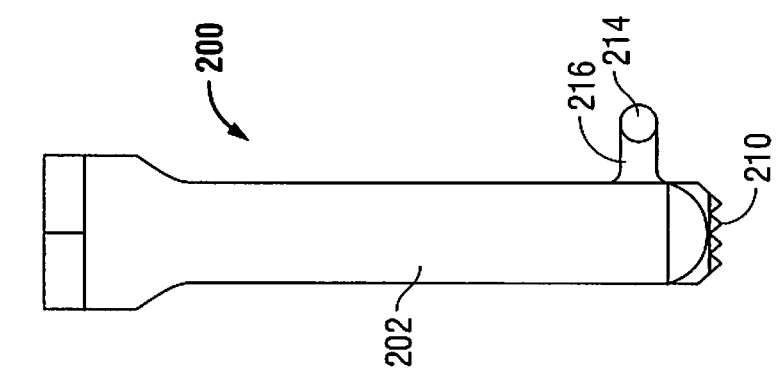
FIG. 27D is a front view of the retractor of FIG. 27.
Figure 27C:
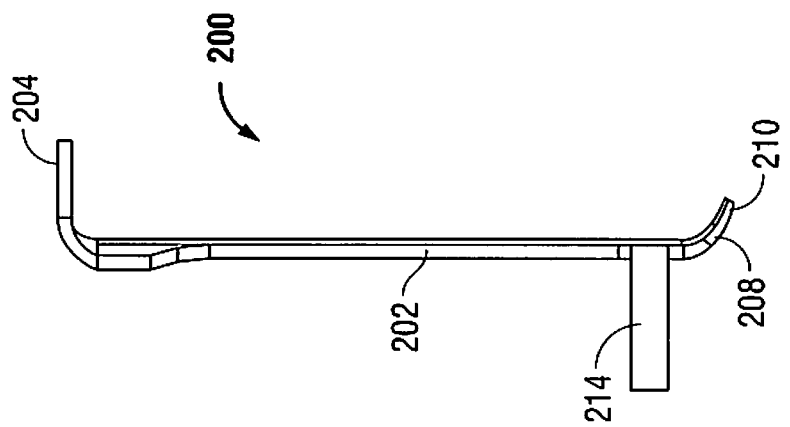
FIG. 27C is a side view of the retractor of FIG. 27.

With the incision between the screws defined, a specialized rigid retractor blade is inserted into the incision. A rigid retractor blade 200 is shown in FIGS. 27 through 27D. As there shown, the rigid blade portion resembles a pharyngeal type retractor. The specialized retractor 200 has a retractor blade portion 202, a proximal flange 204 extending substantially perpendicular to the blade portion a quick release connector extension 206 (shown only in FIG. 27, but intended to be attached to the corresponding opening in FIGS. 27A-27D) extending proximally from flange 204, and an angled distal foot portion 208 with ridges 210 to hold tissue aside and prevent the tissue from slipping under the distal end of the retractor. In addition, retractor 200 includes an extension member 212. Extension member 212 has a rod-shaped portion 214 and a lateral offset arm 216. Lateral offset arm 216 extends to the side of retractor blade 202 and may be formed integrally with the blade. Rod-like portion 214 is attached to and extends from lateral offset arm 216 in a direction generally orthogonal or perpendicular to blade 202, and extending away from the direction of angled foot portion 208 and ridges 210. Rod-like portion 214 has a diameter that substantially corresponds to the diameter and shape of the rod-receiving channel 44 of the polyaxial screw (see FIGS. 16 and 28), the reasons for which will be explained below.

In this method, substantially rigid blade 200 is inserted into the incision and extension member 214 is inserted into the rod receiving channel of one of the screws. In order to accomplish this, it may be desirable to release pressure on the Gelpi retractor which is holding the flexible screw based retractors apart, and insert the extension member down to the desired screw between the flexible arms of the retractor associated with that screw. As will be appreciated, the screw to which extension member is to be inserted should be oriented with the rod receiving channel in the medial-lateral direction, as pointed out above. Once the rigid retractor 200 is positioned in the incision with extension member 18 situated in a rod receiving channel of the screw, the extension member is temporarily fixed to the screw. In the case of a pedicle screw which utilizes a set screw, a known temporary set screw (not shown) may be inserted and tightened to an appropriate degree to secure the extension member to the screw. Of course, it is contemplated that other types of pedicle screws could be used which do not involve a set screw above, in which case the corresponding rod-locking mechanism (e.g. nut, nut screw combination, taper or friction lock) is utilized to temporarily fix the extension member to the screw. One friction lock screw is disclosed in U.S. patent application Ser. No. 11/493,625, filed Jul. 27, 2006, entitled "Multi-Planar Taper Lock Screw," the entire contents of which is herein incorporated by reference.

Figure 28:
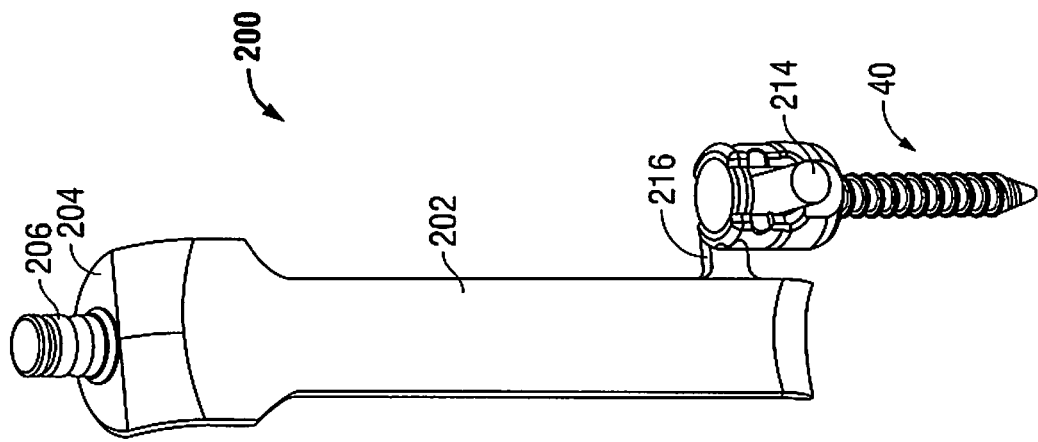
FIG. 28 is a perspective view of the retractor of FIG. 27 with a pedicle screw mounted thereon.

FIG. 28 illustrates the positional relationship of retractor 200 and the pedicle screw 40 with the retractor blade extension member 214 secured in the rod receiving channel of the screw with a set screw, albeit without the screw implanted into bone. Although the retractor 200 is shown in combination with a monoaxial pedicle screw, it is contemplated that the retractor 200 may be used in combination with a polyaxial pedicle screw. Alternatively, the retractor 200 may include a modified lateral offset arm that includes a polyaxial joint that increases the flexibility of the retractor and permits greater ranges of movement during a surgical procedure when combined with a monoaxial pedicle screw. The polyaxial joint is located between the retractor blade and the extension portion. In a further alternate embodiment, the retractor blade and the lateral extension are modular. In this embodiment, the retractor blade is configured and adapted for receiving either a fixed lateral extension or a polyaxial lateral extension. When provided in a kit, the practitioner may select either lateral extension for use with the pedicle screw. Typically, the polyaxial lateral extension is used in conjunction with a monoaxial pedicle screw, while the fixed lateral extension is used with a polyaxial pedicle screw, but other combinations of these structures are contemplated.

Figure 30:
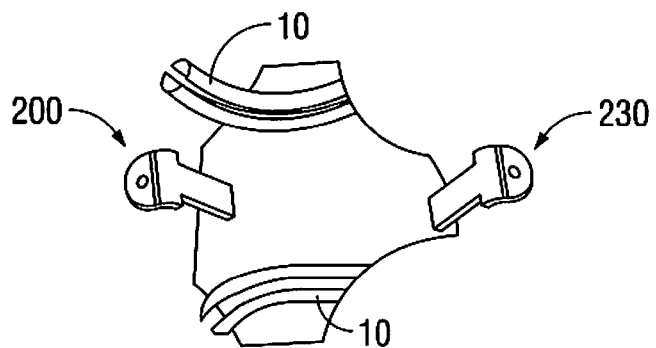
FIG. 30 is a top view of a model illustrating schematically a one-level, unilateral minimally open interbody access channel formed by two flexible minimally invasive retractors oriented cephalad-caudad, and a substantially rigid retractor assembly oriented medial-lateral, with spreading devices removed for viewing purposes.

It is contemplated that rigid retractor blade 200 may be oriented to either the lateral or medial side of the incision. In one embodiment, the rigid retractor is mounted to a pedicle screw so that the rigid blade is disposed on the lateral side of the incision. As will be appreciated, with the extension member mounted and secured to one of the pedicle screws, the rigid refractor blade is fixed in relation to that screw. A second rigid retractor blade 230 (see FIGS. 29A-29D) is then inserted into the incision opposite the first rigid retractor blade 200. Second rigid retractor blade 230 has an elongated rigid blade 232, a horizontal proximal flange 234 having an aperture 236 for a quick connect post, and an angled distal end 23 with ridges 240. FIG. 30 is a schematic illustration of the orientation of the flexible retractors 10 in the cephalad-caudad orientation (without showing the Gelpi retractor holding them apart) and the first rigid retractor 200 (which is fixed to an implanted screw, not shown) disposed laterally and the second rigid retractor disposed medially. Of course, the fixed retractors could not spread apart as illustrated unless attached to a spreading device, as will now be explained.

Figure 31:
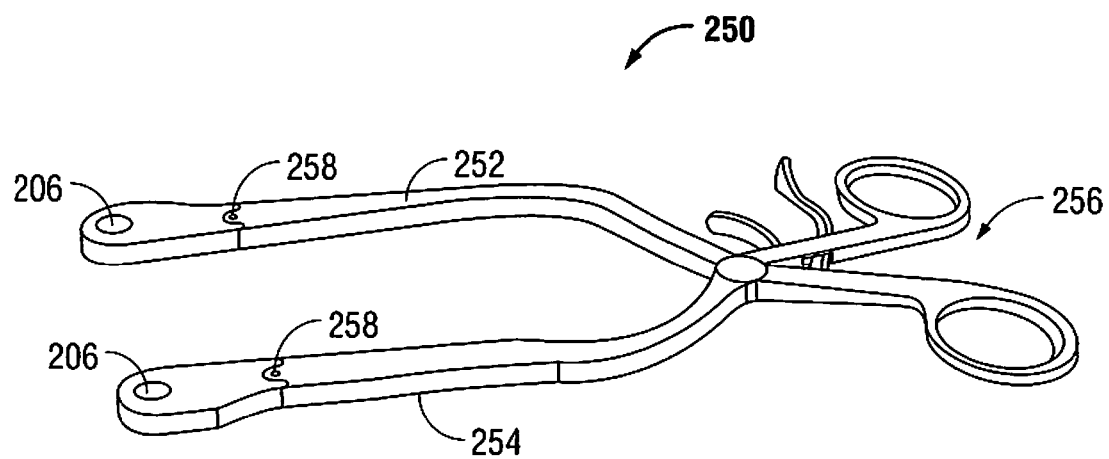
FIG. 31 is a top view of a spreading device in accordance with an embodiment of the present disclosure.
Figure 32:
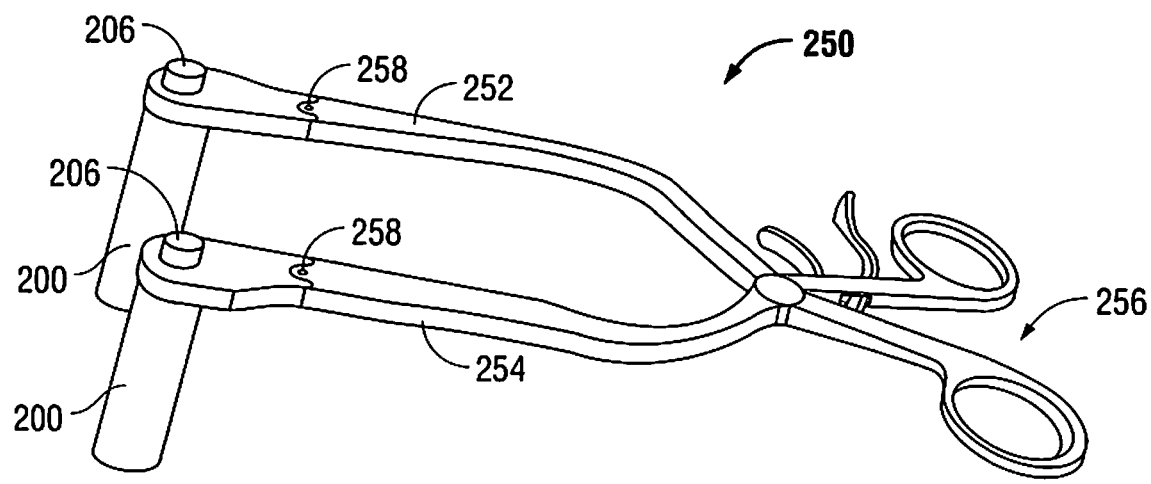
FIG. 32 is a perspective view of the retractor assembly of FIG. 31 with first and second retractor blades attached thereto.

FIG. 31 illustrates a spreading device 250 having a first arm 252 and a second arm 254 connected to a pair of handles 256. Arms 252, 254 have hinges 258 which permit adjustment of the arms 252, 254 in a vertical direction to facilitate manipulation. The distal end of each arm 252, 254 includes an aperture 260 to receive and engage a quick connect post 206 on one of retractor blades 200, 230. As will be appreciated, squeezing handles 256 spreads apart arms 252, 254 to spread retractor blades 200, 230 attached at the distal ends of the arms. FIG. 32 shows spreading device 250 with rigid retractor blades 200, 230 attached by quick connect posts 206 to the distal end of each arm 252, 254.

With rigid retractor 200 disposed in the incision with the extension member secured to the screw and the retractor blade 202 disposed on the lateral side of the incision, and rigid retractor 230 disposed in the incision on the lateral side, and both retractors connected to the distal end of arms 252, 254 of spreading device 250, the handles of the spreading device are squeezed together (and may be latched in position, as appropriate) to cause arms 252, 254 to spread apart the rigid refractor blades in a medial-lateral direction. Because one blade, the lateral blade, is in fixed relation to one of the pedicle screws, spreading the arms of the spreading device will not effect retraction in that direction, but rather will move the opposite retractor away from the retractor blade which is fixed to the screw. Where the fixed retractor blade is the lateral blade, the spreading device will move the opposite blade in the medial direction to give medial retraction and exposure (See FIG. 30). It is also significant that the rigid blade fixed to the screw is or may be laterally offset from the linear axis directly between the screws. In this manner, the fixed retractor blade that is slightly offset from the screw-screw axis does not obstruct the surgeon's view and access along the screw-screw axis. With the fixed retractor blade offset laterally, and the movable rigid blade movable in the medial direction by the spreading device, a highly desirable access path is provided directly to the facet joint and the interbody space for the surgeon to perform a surgical procedure such as a TLIF. Substantially rigid retractor blades 200, 230 are illustrated as metal retractors. However, it is contemplated that the blades may be made of any material that is sufficiently rigid to retract the desired tissue, and may for example be made of stainless steel, titanium, nitinol, rigid plastics such as polycarbonate or glass filled polycarbonate, and may be transparent or opaque and may be provided with means to convey illumination to the surgical site.

After the surgeon has performed the portion of the procedure requiring access to the facet joint and/or interbody space, such as a TLIF procedure, the spreading device is released, disconnected from the retraction blades, and removed. The movable rigid retractor blade 230 is removed from the incision, and the fixed rigid retractor blade 200 is released from the pedicle screw and removed from the incision. The flexible screw-based retractors and the rod-receiving channels of the pedicle screws are then re-oriented so that the flexible arms of each screw-based retractors may be spread apart in the medial-lateral direction.

Figure 29A:
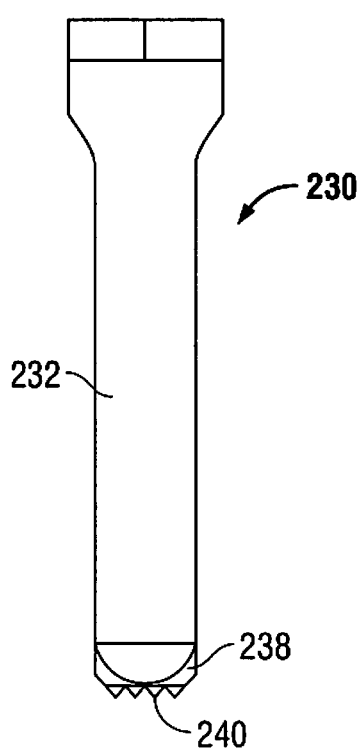
FIG. 29A is a front view of a second rigid retractor blade in accordance with an embodiment of the present disclosure.
Figure 29B:
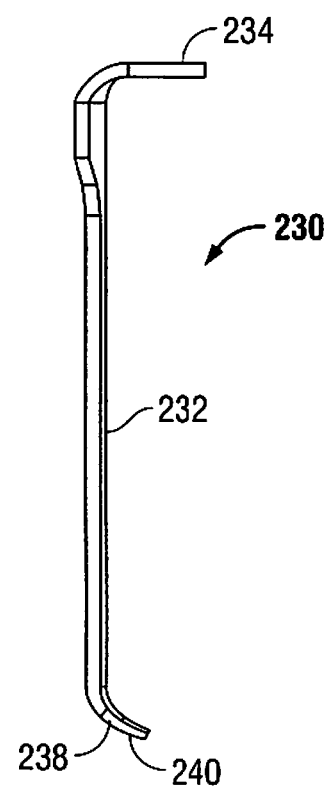
FIG. 29B is a side view of the second rigid retractor blade of FIG. 29A.
Figure 29C:
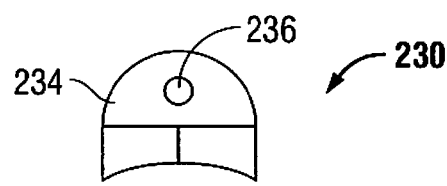
FIG. 29C is a top view of the second rigid retractor blade of FIG. 29A.
Figure 29D:
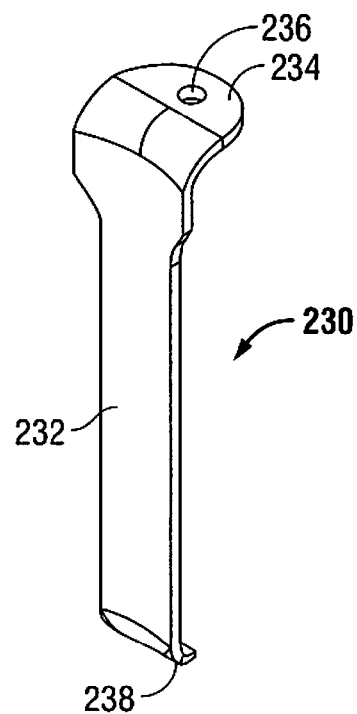
FIG. 29D is a perspective view of the second rigid retractor blade of FIG. 29A.
Figure 29E:
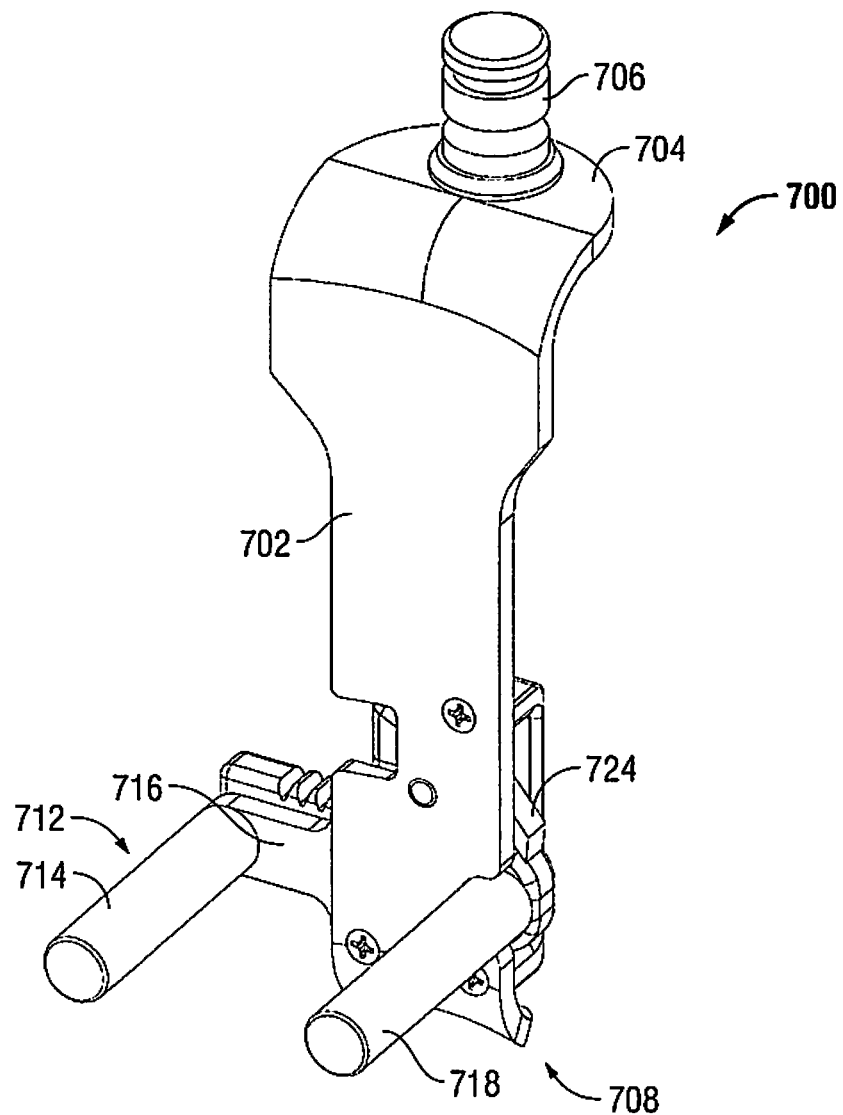
FIG. 29E is a perspective view of a retractor in accordance with an embodiment of the present disclosure, showing the rod-shaped portions approximated to each other.
Figure 29F:
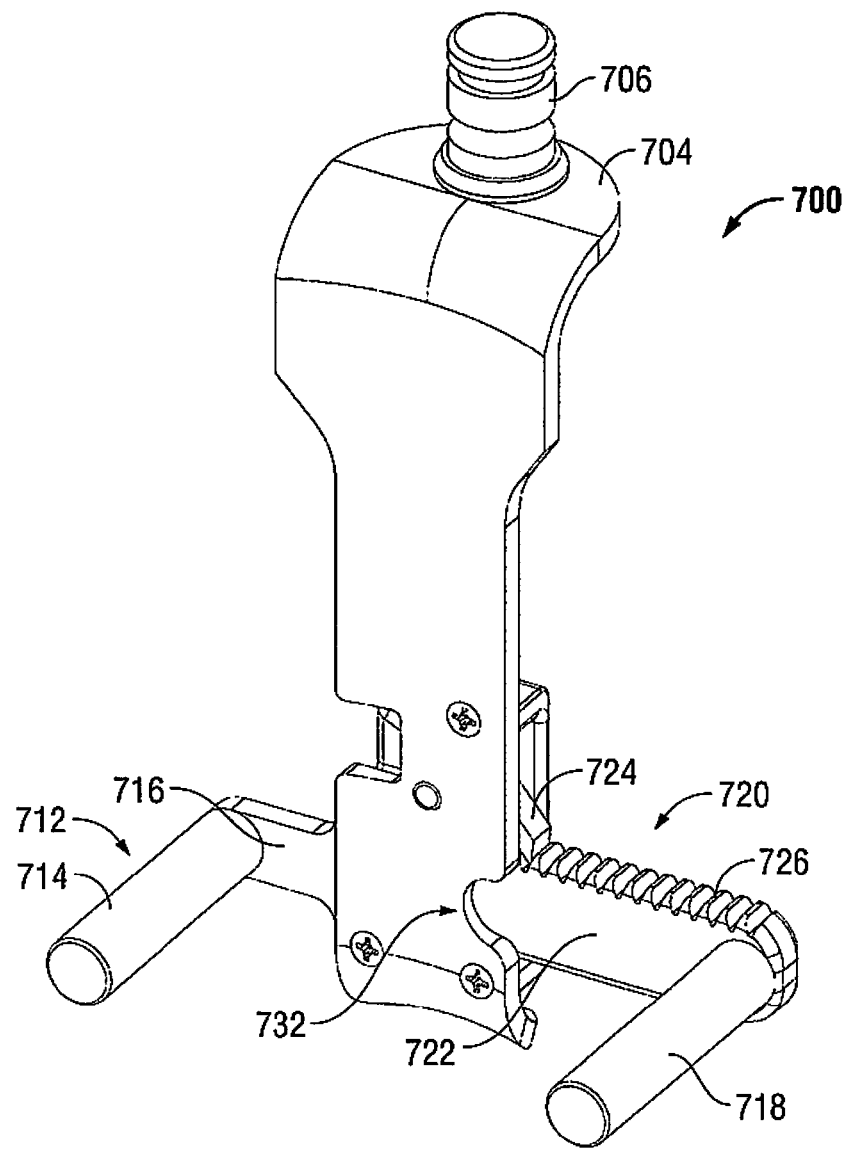
FIG. 29F is a perspective view of the retractor of FIG. 29E with the rod-shaped portions spaced apart from each other.

With reference to FIGS. 29E-29H, an alternate embodiment of the retractor blade is generally designated as 700. Retractor blade 700 is similar to retractor blade 200. As such, retractor blade 700 includes a retractor blade portion 702, a proximal flange 704 extending substantially perpendicular from blade portion 702, a quick release connector extension 706 extending proximally from proximal flange 704, and an angled distal foot portion 708 with ridges 710 for holding tissue laterally relative to the retractor blade 700 and inhibiting tissue from slipping under the distal foot portion 708. Retractor blade 700 also includes an extension member 712 having a first rod-shaped portion 714 and a lateral offset arm 716. First rod-shaped portion 714 protrudes in a substantially perpendicular direction with respect to the lateral offset arm 716. Retractor blade 700 additionally includes a second rod-shaped portion 718 operatively connected to a ratchet mechanism 720. Ratchet mechanism 720 includes an arm 722 configured to slide laterally relative to lateral offset arm 716 and a pawl 724 pivotally coupled to the retraction blade portion 702. Arm 722 of ratchet mechanism 720 has teeth 726 adapted to engage the pawl 724. Aside from teeth 726, arm 722 may contain a slot 728 formed along at least a portion of a length thereof, as depicted in FIG. 29H. Slot 728 slidably engages a pin 730 protruding from lateral offset arm 716. Slot 728 and pin 730 intersect to maintain relative positioning of arm 722 and blade portion 702. Pawl 724 is capable of pivoting toward arm 722 in order to engage teeth 726 and lock arm 722 into position and helps maintain the relative positioning of rod-shaped portions 714, 718. Arm 722 may be repositioned by pivoting pawl 724 away from arm 722 such that the pawl 722 no longer engages teeth 726. Once the pawl 724 has been disengaged from teeth 726, second rod-shaped portion 718 may be translated away or toward first rod-shaped portion 714. As shown in FIG. 29H, ratchet mechanism 720 further includes a spring 734, or any other suitable biasing member, operatively associated with pawl 724. Spring 734 biases pawl 724 toward teeth 726. Since spring 734 is biased toward teeth 726, a surgeon has to use a separate tool, or any other means, to release pawl 724 from teeth 726, allowing arm 722 to move toward blade portion 702. To facilitate movement of second rod-shaped portion 714, retractor blade portion 702 has a lateral cutout or opening 732 dimensioned to receive second rod-shaped portion 718, as shown in FIG. 29E. Lateral cutout 732 allows second rod-shaped portion 718 to move closer to first rod-shaped portion 714. Each of the first and second rod-shaped portions 714, 718 may have a diameter that substantially corresponds to the diameter of the rod-receiving channel 44 of a polyaxial screw illustrated in FIGS. 16 and 28.

Although the drawings show rod-shaped portions 714, 718 having a cylindrical shape, rod-shaped portions 714, 718 may feature a half-rounded shape with rounded bottom section for locking the polyaxial screw in position and a flat top section for engages a set screw. During use, the set screw engages the flat top section to orient rod-shaped portions 714, 718 relative to the set screw and applies force on rod-shaped portions 714, 718. The force exerted on the rod-shaped portions is transmitted to the set screw to lock the set screw to the screw-rod housing.

The method of using retractor blade 700 is substantially similar to the method of employing retractor blade 200. One retractor blade 700, however, is capable of moving two pedicle screws mounted on first and second rod-shaped portions 714, 718. To approximate and separate first and second rod-shaped portions 714, 718 from each other, a surgeon may employ the spreading device illustrated in FIG. 34.

Figure 34:
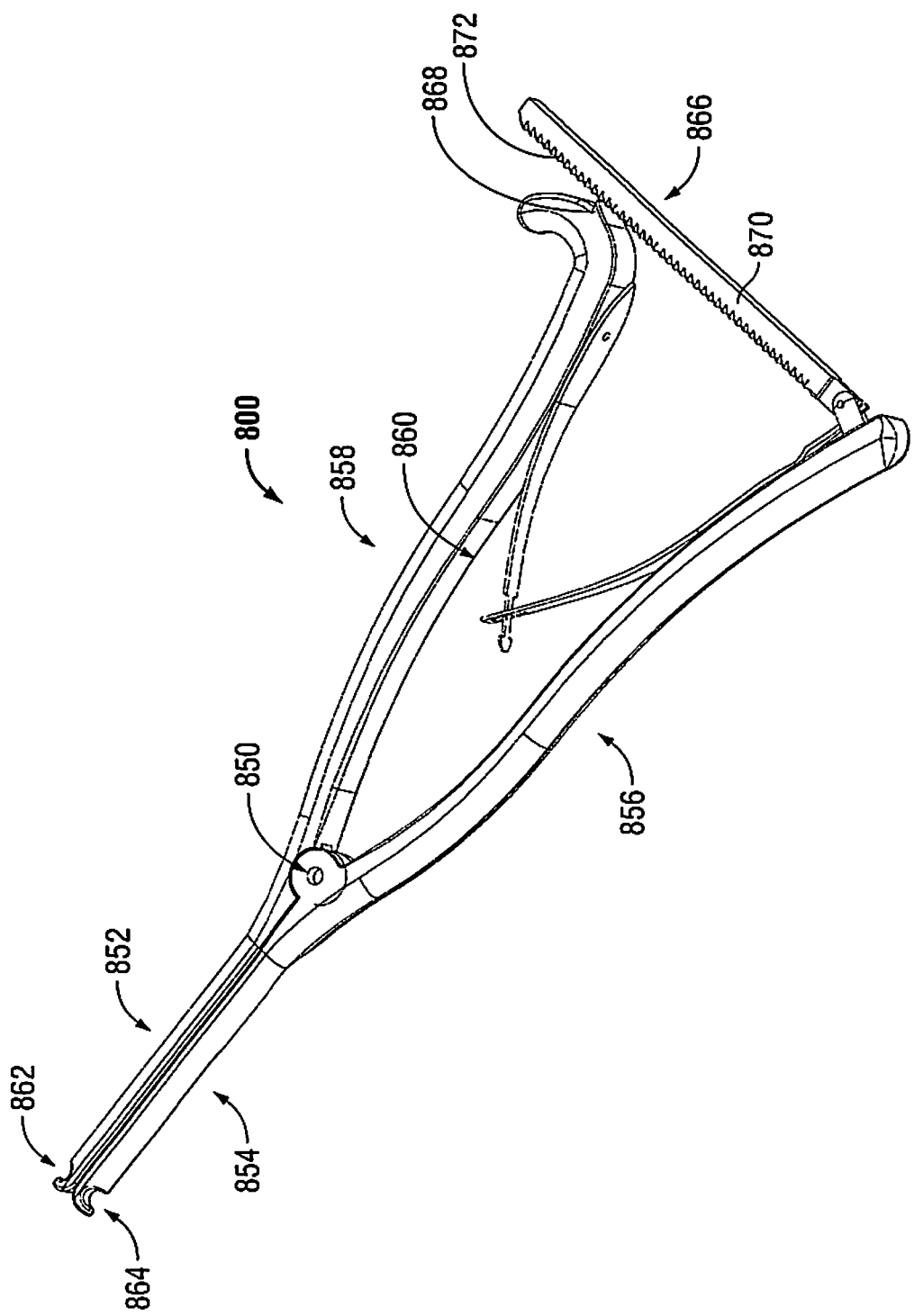
FIG. 34 is a perspective view of a spreading device in accordance with an embodiment of the present disclosure.
Figure 35:
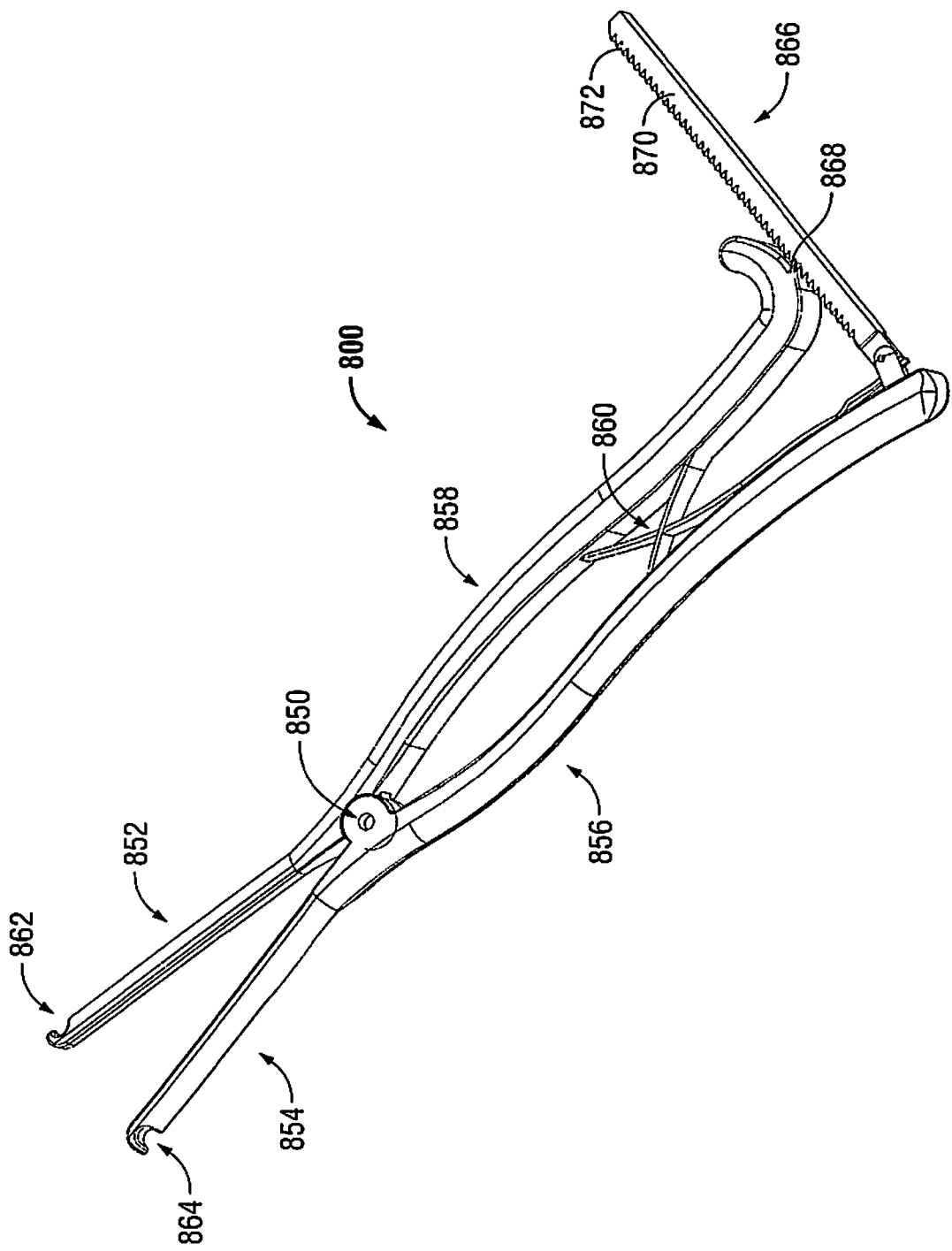
FIG. 35 is a perspective view of the spreading device of FIG. 34, showing the arms spaced apart from each other.

FIGS. 34 and 35 show a spreading device 800 including a first arm 852 and a second arm 854 pivotally coupled to each other. A pivot pin 850, or any other suitable apparatus, operatively connects first and second arms 852, 854. Each of first and second arms 852, 854 includes a respective recess 862, 864 adapted for receiving the rod-shaped portions of a retractor. Recesses 862, 864 face away from each other and are formed on the lateral surfaces of the corresponding first and second arms 852, 854. In addition, first and second arms 852, 854 are each operatively coupled to a corresponding handle 858, 856. Due to the structural relationship between first and second arms 852, 854 and handles 856, 858, approximating or squeezing handles 856, 858 toward each other causes first and second arms 854, 856 to spread apart, as shown in FIG. 35. Conversely, separating handles 856, 858 away from each other moves the arms 854, 856 close to each other, as seen in FIG. 34. Spreading device 800 may include a biasing member 860 operatively associated with handles 856, 858. Biasing member 860 urges handles 856, 858 away from each other, thereby biasing the first and second arms 852, 854 toward each other. Handles 856, 858 may also be operatively connected to a ratchet mechanism 866 for locking arms 852, 854 into position. Ratchet mechanism 866 includes a pawl 868 coupled to handle 858 and a linear rack 870 attached to handle 856. As seen in FIG. 34, linear rack 870 contains teeth 872 adapted to engage pawl 868 and may be pivotally connected to handle 856 to allow disengagement of linear rack 870 from pawl 868. Linear rack 870 may be pivoted away from pawl 868 to unlock ratchet mechanism 866. Normally, linear rack 870 is placed against pawl 868 and a movement of handles 856, 858 causes pawl 868 to rise and fall over teeth 872 and ultimately locks handle 856, 858 in place. Alternatively, the user initially squeezes handles 856, 858 and then moves linear rack 870 toward pawl 868 until pawl 868 engages a tooth 872 of linear rack 870 to lock arms 852, 854 in place. During use, spreading device 800 may be utilized to spread rod-shaped portions 714, 718 of retractor blade 700, as discussed hereinbelow.

In operation, the retractor blade 700 is mounted to two adjacent pedicle screws attached to vertebral bodies. These pedicle screws may be inserted percutaneously into a vertebral body with retractor 10, 10', 50, or any other suitable apparatus. Spreading device 800, or any other suitable spreading instrument, is then used to spread the rod-shaped portions 714, 718 apart, thereby distracting the vertebral bodies to which the screws are mounted. Afterwards, spreading device 250, or any other suitable device such as a Gelpi retractor, is connected to retraction blade 700. As discussed above with regard to retraction blade 200, the surgeon may then utilize spreading device 250 to spread apart two retractor blades 700 from each other. Since the retraction blade 700 is affixed to the pedicle screws mounted on the vertebral bodies, the pedicle screws are less likely to be dislodged or dislocated by the patient's breathing, physical contact with the patient, or manipulation of tools or instruments.

Figure 35A:
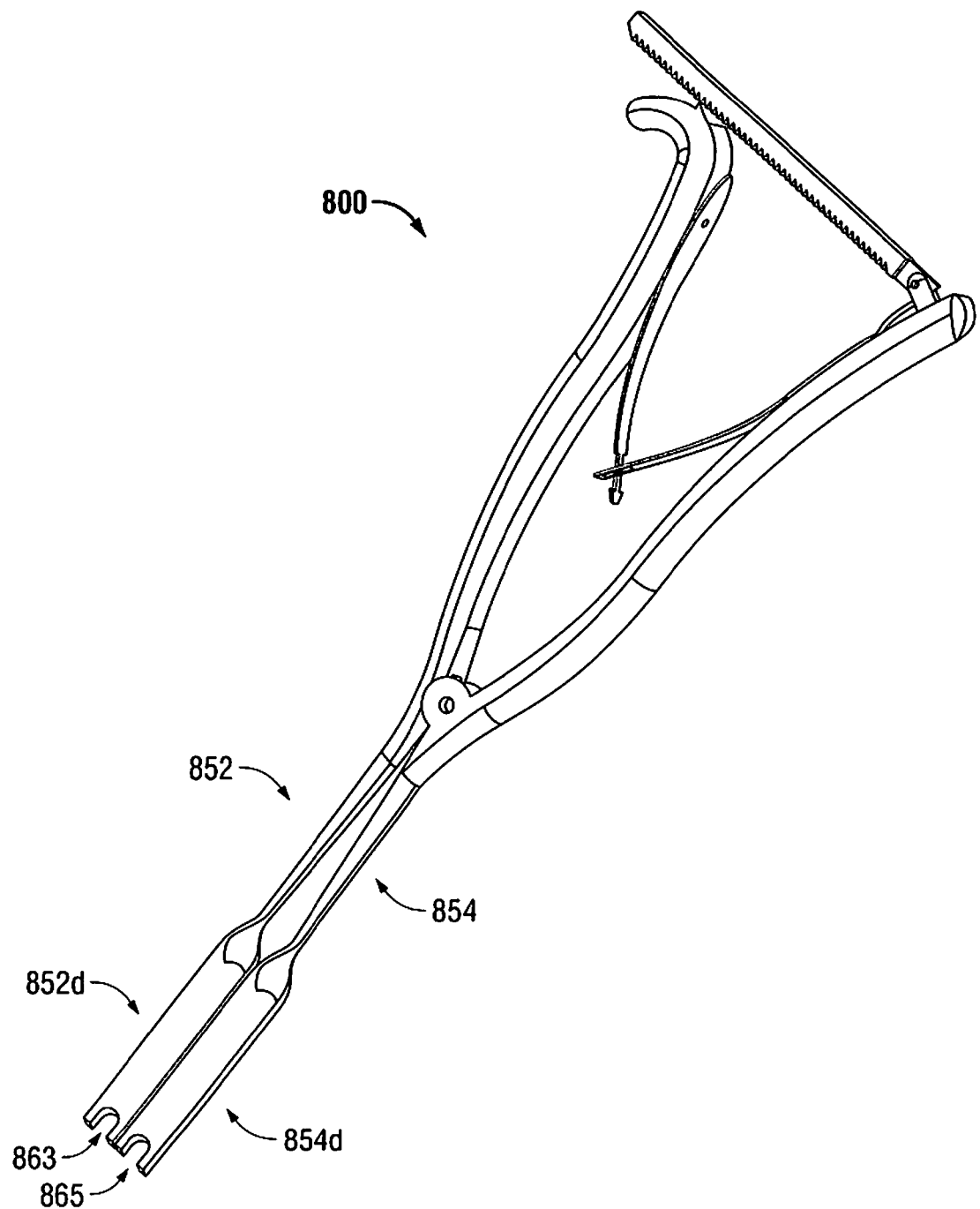
FIG. 35A is a perspective view of a spreading device according to an embodiment of the present disclosure.

In an alternative embodiment of spreading device 800, the distal regions 852d, 854d of first and second arms 852, 854 are flat structures, as shown in FIG. 35a. Each distal region 852d, 854d includes a recess 863, 865 formed at the longitudinal end surfaces of first and second arms 852, 854. Recess 863, 865 are each adapted to receive a rod-shaped portions of a retraction system.

Figure 51:
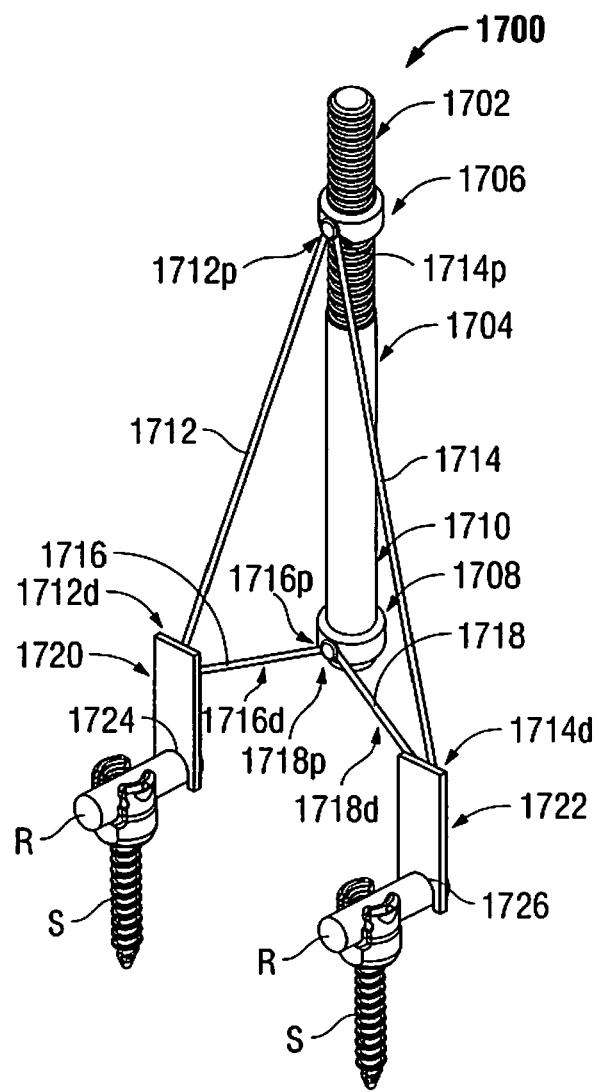
FIG. 51 is a perspective view of a spreading device according to an embodiment of the present disclosure.
Figure 52:
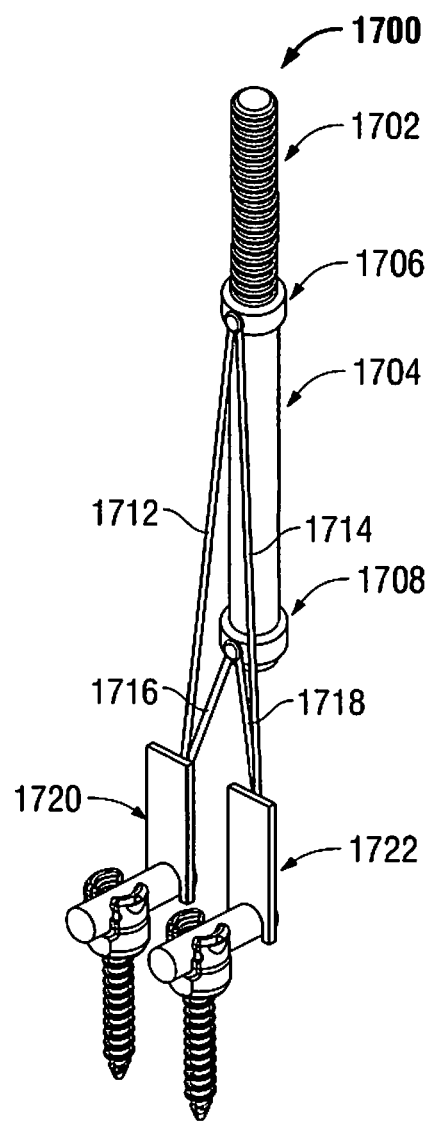
FIG. 52 is perspective view of the spreading device of FIG. 51 with the spreading plates approximated to each other.

FIGS. 51 and 52 show an alternate embodiment of a spreading device generally designated as 1700. Spreading device 1700 is configured to spread the rod-shaped portions of a retraction system and includes an externally threaded shaft 1702 and a hollow shaft 1704 having a bore adapted to receive externally threaded shaft 1702. The inner surfaces of hollow shaft 1704 may form an internal thread configured to engage the external threads of shaft 1702. Due to the structural relationship between externally threaded shaft 1702 and hollow shaft 1704, rotating threaded shaft 1702 clockwise moves threaded shaft 1702 distally relative to hollow shaft 1704. Conversely, rotating threaded shaft 1702 counterclockwise moves threaded shaft 1702 proximally with respect to hollow shaft 1704. Spreading device 1700 further includes a movable ring 1706 positioned around a portion of threaded shaft 1702. During operation, movable ring 1706 moves concomitantly with threaded shaft 1702 when threaded shaft 170 moves proximally or distally. Nonetheless, movable ring 1706 does not rotate with threaded shaft 1702. In addition, spreading device 1700 includes a fixed ring 1708 fixedly attached to a distal portion 1710 of hollow shaft 1704.

Spreading device 1700 further contains first, second, third and fourth rods 1712, 1714, 1716, 1718. Together, first, second, third and fourth rods 1712, 1714, 1716, 1718 form a four-bar linkage. Each rod 1712, 1714, 1716, 1718 has a respective proximal and distal ends 1712p, 1712d, 1714p, 1714d, 1716p, 1716d, 1718p, 1718d. Proximal ends 1712p, 1714p of corresponding first and second rods 1712, 1714 are pivotally coupled to movable ring 1706. Proximal ends 1716p, 1718p of third and fourth rods 1716, 1718 are pivotally connected to fixed ring 1708. Distal ends 1712d, 1716d of first and third rods 1712, 1716 are pivotally connected to a first spreading plate 1720. Distal ends 1714d, 1718d of second and fourth rods 1714, 1718 are pivotally connected to a second spreading plate 1722. First and second spreading plates each include a recess 1724, 1726 adapted to receive a rod-shaped portion "R" of a retraction system. Generally, rod-shaped portions are secured to pedicle screws "S."

During operation, a surgeon utilizes spreading device 1700 to separated rod-shaped portions "R" of a retraction system. To space apart the rod-shaped portions "R," the surgeon first positions grabs rod-shaped portions "R" with recess 1724, 1726, while first and second spreading plates 1720, 1722 are approximated to each other, as seen in FIG. 52. Thereafter, the surgeon rotates threaded shaft 1702 in a counterclockwise direction to move threaded shaft 1702 proximally. As threaded shaft 1702 translates proximally, movable ring 1706 also translates in a proximal direction. The proximal translation of movable ring 1706 causes the distal ends 1712d, 1714d, 1716d, 1716d of first, second, third and fourth rods 1712, 1714, 1716, 1718 to move proximally and outwardly relative to hollow shaft 1704. This movement of first, second, third and fourth rods 1712, 1714, 1716, 1718 separates first and second spreading plates 1720, 1722 from each other, thereby spreading apart rod-shaped portions "R." Since each rod-shaped portion "R" is secured to a pedicle screw "S," separating the rod-shaped portions "R" increases the distance between the pedicle screws. Due to its versatility, a surgeon may use spreading device 1700 with retraction blade 700, or any other suitable retraction system, to separate pedicles screws implanted in vertebral bodies.

Figure 29I:
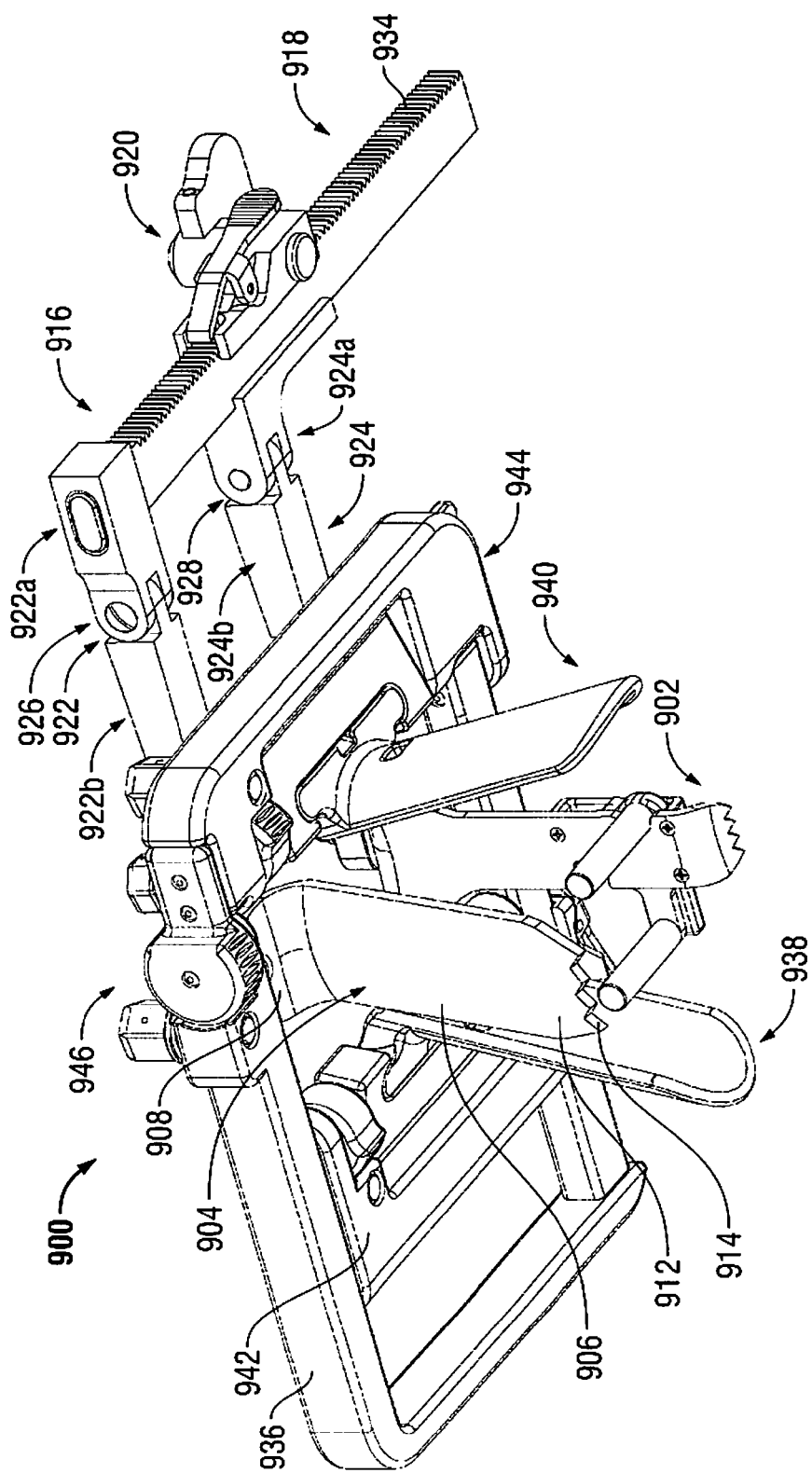
FIG. 29I is a perspective view of a retraction system according to an embodiment of the present disclosure.
Figure 29J:
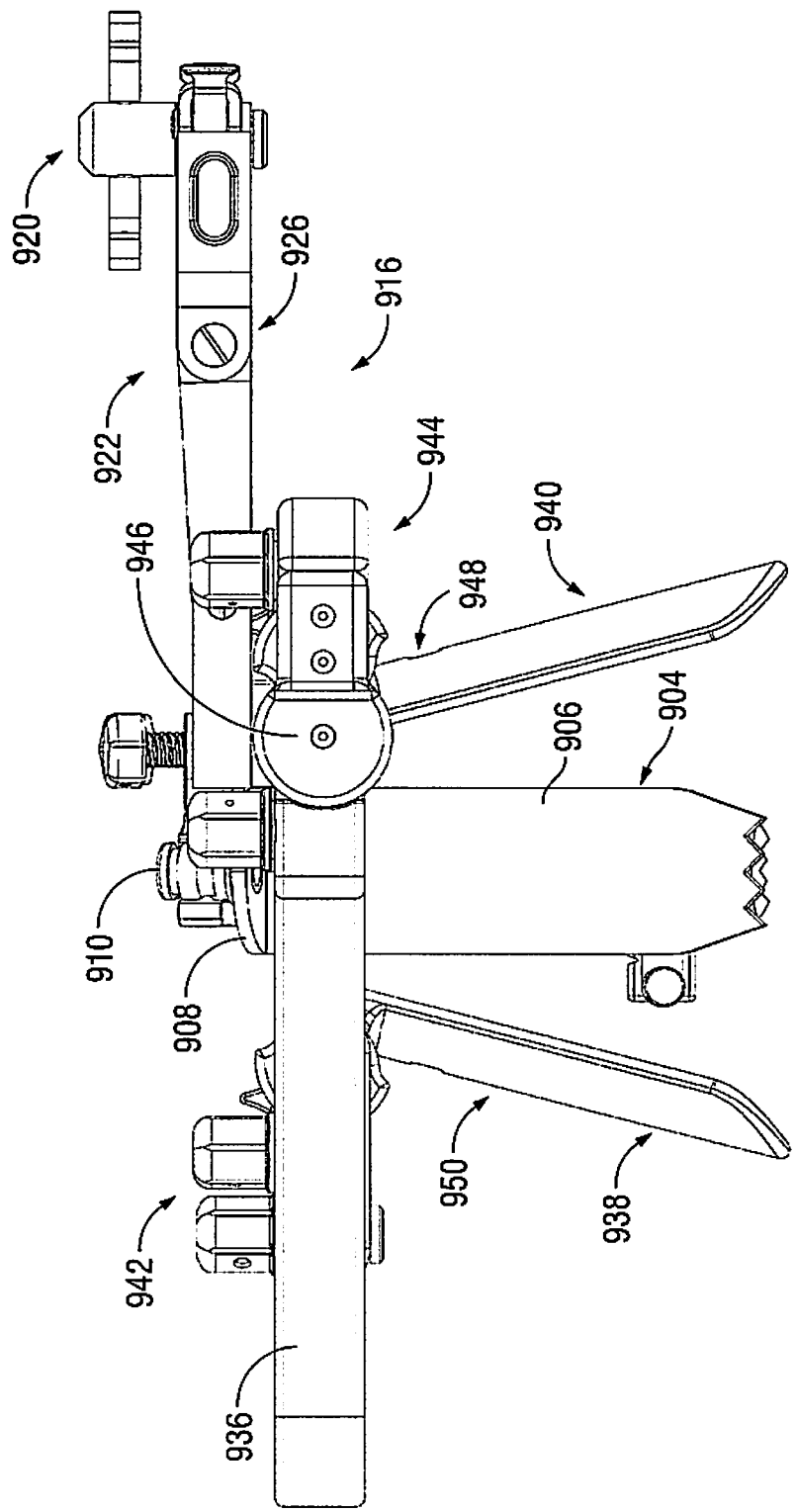
FIG. 29J is a front view of the retraction system shown in FIG. 29I.
Figure 29K:
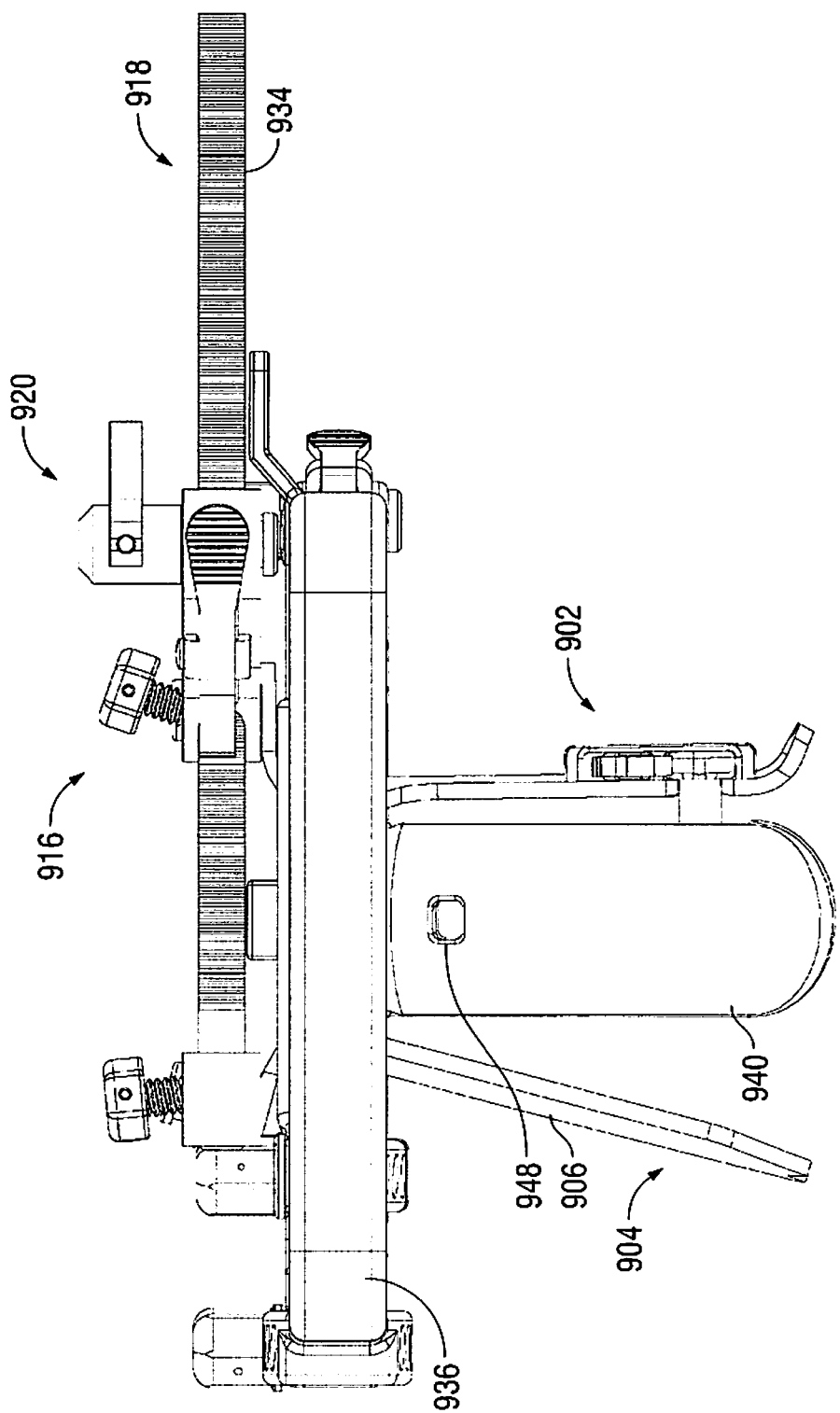
FIG. 29K is a rear view of the retraction system shown in FIG. 29I.

As seen in FIGS. 29I-29K, retractor blade 700, or any other suitable retractor blade, may alternatively be mounted on a substantially rigid frame 900 capable of moving rod-shaped portions 714, 718 and distracting tissue or vertebral bodies at an incision site. Rigid frame 900 includes a ratchet mechanism 916 operatively connected to a pair of retraction blades 902, 904. Ratchet mechanism 916 includes a rack 918, a pawl 920 slidably mounted on the rack 918, and two extension arms 922, 924 extending from the rack 918. Rack 918 has teeth 934 adapted to engage pawl 920. Pawl 920 is capable of sliding along rack 918 and engages a tooth 934 to lock extension arm 924. Ratchet mechanism 916 may include a spring (not shown), or any other suitable biasing member, to bias pawl 920 toward teeth 934 of rack 918. A user may employ a separate tool, or any other means, to release pawl 920 from teeth 934, allowing extending arm 924 to move toward extension arm 922. Extension arm 924, which is attached to retraction blade 902, is operatively connected to pawl 920. Hence, extension arm 924 moves concomitantly with pawl 920 when pawl 920 moves along rack 918. Moving extension arm 924 moves the retraction blade 902 attached to it. Conversely, retraction blade 902 may locked into position by engaging pawl 920 with one of the teeth 934 of rack 918. When pawl 920 engages a tooth 934, extension arm 924 fixes its position and inhibits movement of retraction blade 902.

As discussed above, extension arms 922, 924 are each connected to a corresponding retraction blade 902, 904. In addition, extension arms 922, 924 include first and second portions 922a, 924a, 922b, 924b separated by hinges 926, 928.

First retraction blade 902 is substantially similar to retraction blade 700. Second retraction blade 904 includes a retraction blade portion 906, a proximal flange 908 extending substantially perpendicular from blade portion 906, a quick release connector extension 910, and a distal foot portion 912 with ridges 914 to hold tissue. Quick release connector extension 910 is operatively connected to extension arm 922 of the ratchet mechanism 916.

In addition to ratchet mechanism 916, rigid frame 900 includes a body 936 supporting first and second distraction blades 938, 940. First and second distraction blades 938, 940 feature concave profiles and are adapted to displace tissue. Moreover, each distraction blade 938, 940 includes a window 948, 950 to enable observation of a patient's anatomy beyond the blades. First distraction blade 938 is attached to a slidable mount 942 configured to move with respect to body 936. In operation, moving mount 942 translates distraction blade 938 closer or farther from retraction blade 940. Second distraction blade 940 is coupled to an end portion 944 of the body 936. A hinge 946 pivotally attaches end portion 944 to the remaining part of body 936. As a result, end portion 944 has the ability to pivot with respect to the body 936. Since second distraction blade 938 is operatively connected to end portion 944, a pivoting of end portion 944 causes second distraction blade 938 to pivot about hinge 946.

In operation, a surgeon may employ rigid frame 900 to distract tissue and separate vertebral bodies. Initially, the surgeon makes an incision in the medial lateral direction or in the cephalad-caudal direction. Then, the incision is then retracted by placing distraction blades 938, 940 with their free ends close together into the incision. The surgeon may illuminate the surgical site with a fiberoptic lighting instrument or any other suitable lighting device. After placing the distraction blades 938, 940 in the desired surgical site, the surgeon may slide first distraction blade 938 relative to body 936 of frame 900 to separate first and second distraction blades 938, 940 from each other, thereby retracting soft tissue at the incision. Subsequently, the surgeon utilizes the ratchet mechanism 916 to separate soft tissue with first and second retraction blades 902, 904. To separate first and second retraction blades 902, 904, the surgeon moves the pawl 920 along rack 918 until the pawl 916 reaches the desired position. As pawl 920 moves along rack 918, first retraction blade 902 moves and separates from second retraction blade 904, thereby retracting tissue. Since pawl 920 is biased toward rack 918, moving pawl 920 away from extension arm 922 causes pawl 920 to rise and fall over teeth 934, and ultimately pawl 920 locks extension arm 924 in place. Following tissue retraction, the surgeon inserts pedicle screws in the vertebral bodies by employing any of the methods described above. Alternatively, the surgeon may insert pedicle screws percutaneously before retracting tissue. Then, the rod-shaped portions of first retraction blade 902 are mounted on the pedicle screws. The surgeons subsequently retracts vertebral bodies by separating the rod-shaped portions of first retraction blade 902 as discussed above with regards to retraction blade 700.

Figure 29L:
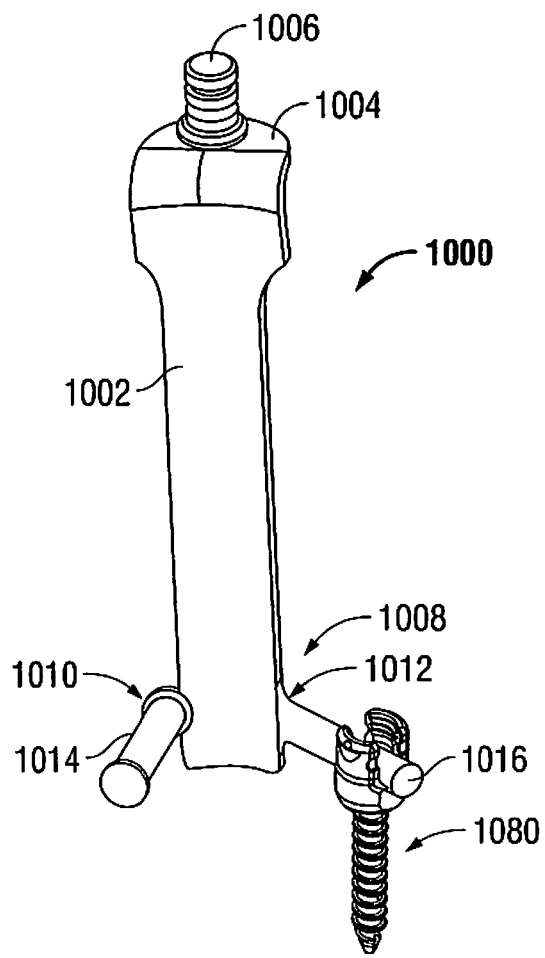
FIG. 29L is a perspective view of a retraction system according to an embodiment of the present disclosure with a pedicle screw mounted on a rod-shaped portion of the retraction system.
Figure 29M:
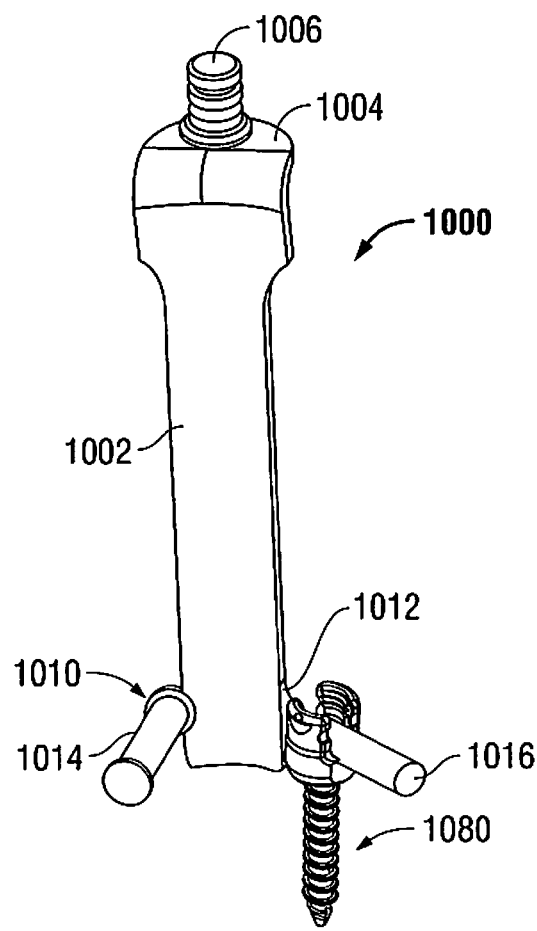
FIG. 29M is a perspective view of the retraction system of FIG. 29L with the pedicle screw approximated to the retraction blade portion of the retraction system.

With reference to FIGS. 29L and 29M, another embodiment of the retractor blade is generally designated as 1000. Retraction blade 1000 is substantially similar to retraction blade 200. Like retraction blade 200, retraction blade 1000 contains a retraction blade portion 1002, a proximal flange 1004 extending substantially perpendicular from retraction blade portion 1002, a quick release connector extension 1006 extending proximally from the proximal flange 1004, and a distal foot portion 1008. The distal foot portion 1008, however, includes first and second extension members 1010, 1012 that are laterally offset relative to retraction blade portion 1002. First and second extension members 1010, 1012 each include a respective a rod-shaped portion 1014, 1016 extending from the corresponding therefrom. Second extension member 1012 may be pivotally attached to retraction blade portion 1002. Both rod-shaped portions 1014, 1016 are adapted to be positioned within the rod-receiving channel of a pedicle screw 1080. The first rod-shaped portion 1014 extends in a substantially perpendicular direction from first extension member 1010, whereas the second rod-shaped portion 1016 extends obliquely from second extension member 1012.

During operation, a surgeon utilizes retractor blade 1000 to separate pedicle screws inserted in vertebral bodies. Initially, the surgeon inserts retraction blade 1000 through an incision and rod-shaped portions 1014, 1016 are placed within the rod receiving channels of pedicle screws 40. The rod-shaped portions 1014, 1016 are then fixed to the pedicle screws with any suitable apparatus, component, or device. For instance, the surgeon may employ a set screw to secure the rod-shaped portions 1014, 1016 to the pedicle screws. At the outset, the pedicle screw 40 mounted on the second rod-shaped portion 1016 are positioned closer to retractor blade portion 1002 to minimize the distance between the pedicle screws positioned on rod-shaped portions 1014, 1016. To increase the distance between pedicle screws 40, the surgeon slides the pedicle screw 40 away from retractor blade portion 1002 along rod-shaped portion 1016 and/or pivots second extension member 1012 away from first extension member 1010. As pedicle screw 40 moves along rod-shaped portion 1016, the distance between the two pedicle screws 40 increases and the vertebral bodies attached to the pedicle screws 40 move away from each other.

Figure 29N:
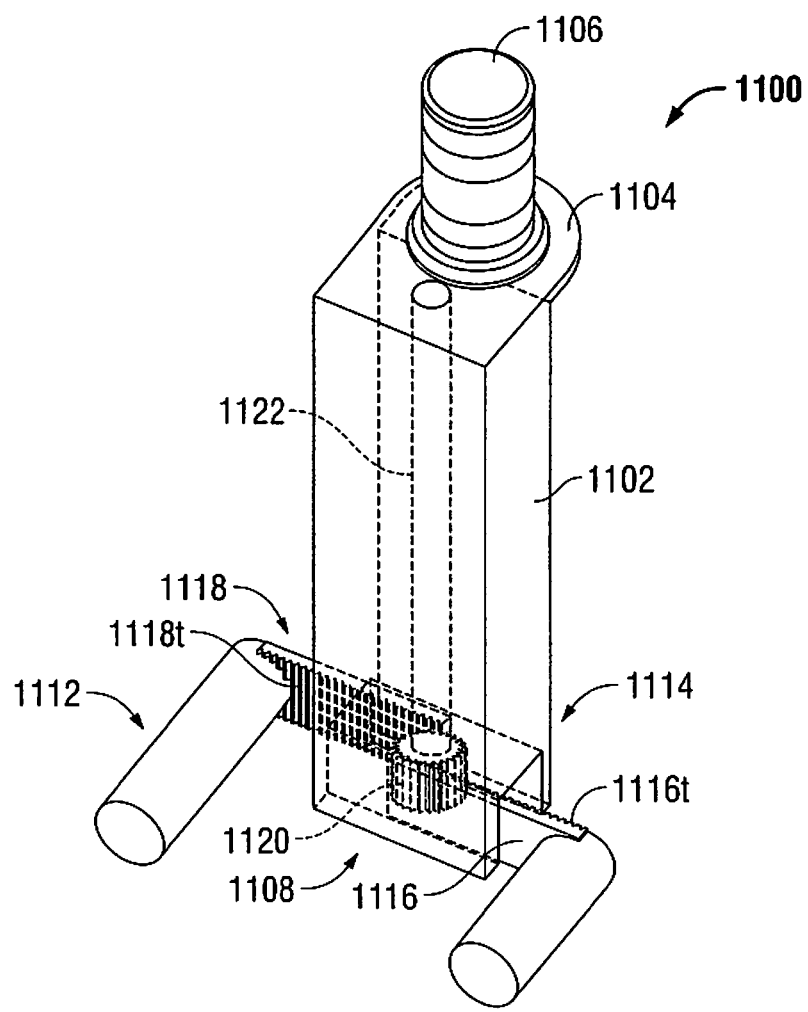
FIG. 29N is a perspective view of a retraction system according to an embodiment of the present disclosure.

Referring to FIG. 29N, still another embodiment of the retractor blade is identified in the drawings as 1100. Retractor blade 1100 includes a retraction blade portion 1102, a proximal flange 1104 extending substantially perpendicular form retraction blade portion 1102, a quick release connector portion 1106 extending proximally from proximal flange 1104, and a distal foot 1108. Distal foot 1108 includes a ratchet mechanism 1114 operatively associated with first and second rod-shaped portions 1110, 1112. Ratchet mechanism 1114 includes first and second racks 1116, 1118, a pinion 1120, and a shaft 1122 operatively connected to pinion 1120. First rack 1116 contains teeth 1116$t$ adapted to engage pinion 1120 and is operatively coupled to first rod-shaped portion 1110. Similarly, second rack 1118 includes teeth 1118$t$ configured to engage pinion 1120 and is operatively connected to second rod-shaped portion 1112. Shaft 1122 extends from the pinion 1120 to proximal flange 1104.

During operation, any suitable apparatus, device, system, or means may rotate or lock shaft 1122. Since shaft 1122 is disposed in mechanical cooperation with pinion 1120, rotating shaft 1122 prompts the rotation of pinion 1120. As pinion 1120 rotates, teeth 1116$t$ and 1118$t$ of first and second racks 1116, 1118, respectively, engage pinion 1120 and cause the translation of racks 1116 and 1118. Specifically, when pinion 1120 rotates clockwise, first and second racks 1116, 1118 move toward a centerline of retraction blade portion 1102, causing first and second rod-shaped portions 1110, 1112 to move toward each other. Conversely, when pinion 1120 rotates counterclockwise, first and second racks 1116, 1118 move away from retraction blade portion 1102, thereby increasing the distance between rod-shaped portions 1110, 1112. In a surgical procedure, the surgeon inserts retraction blade 1100 with rod-shaped portions 1110, 1112 close to each other. The surgeon then attaches each rod-shaped portion 1110, 1112 to a pedicle screw. Each pedicle screw is already fixed to a vertebral body. After securing the rod-shaped portions 1110, 1112 to the pedicle screws, the surgeon rotates shaft 1122 counterclockwise to separate rod-shaped portions 1110, 1112. While rod-shaped portions 1110, 1112 separate from each other, the pedicle screws move away from each other and separate the vertebral bodies attached thereto.

Figure 29P:
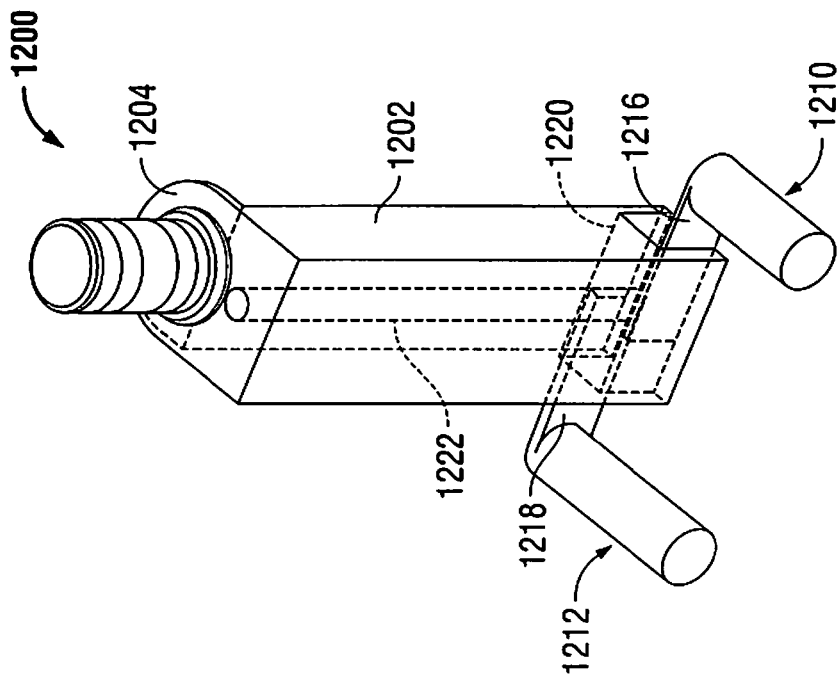
FIG. 29P is a perspective view of the retraction system of FIG. 29O with the rod-shaped portions spaced apart from each other.
Figure 29O:
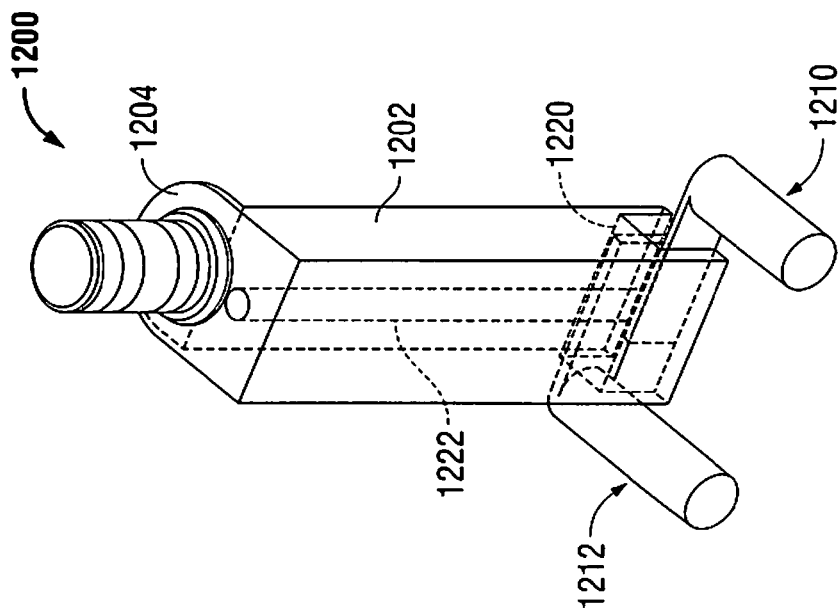
FIG. 29O is a perspective view of a retraction system according to an embodiment of the present disclosure with rod-shaped portions approximated to each other.

FIGS. 29O and 29P illustrate an alternate embodiment of the retraction blade 1200. The structure and operation of retraction blade 1200 is substantially similar to the structure and operation of retraction blade 1100. Retraction blade 1200, however, includes a translation mechanism 1202 instead of a ratchet mechanism. Translation mechanism 1202 is operatively associated with rod-shaped portions 1210, 1212 and includes a housing 1220 containing a pair of slidable arms 1216, 1218. First and second slidable arms 1216, 1218 are configured to slide longitudinally with respect to each other. Translation mechanism 1202 may further include a locking pin 1222 extending from the housing to the proximal flange 1204 of the retraction blade 1200. A portion of pin 1222 is positioned between first and second arms 1216, 1218. When externally engaged, locking pin 1222 inhibits translation of first and second arms 1216, 1218.

In use, a surgeon initially secures each rod-shaped portion 1210, 1212 to a pedicle screw to a vertebral body, while the rod-shaped portions are approximated to each other. Thereafter, the surgeon separates the pedicle screws, and thus the vertebral bodies, by physically spacing apart rod-shaped portions 1210, 1212 with any suitable instrument or device. Subsequently, the surgeon rotates pin 1222 and fixes the relative position of rod-shaped portions 1210, 1212 by locking arms 1216, 1218 in place.

Figure 36:
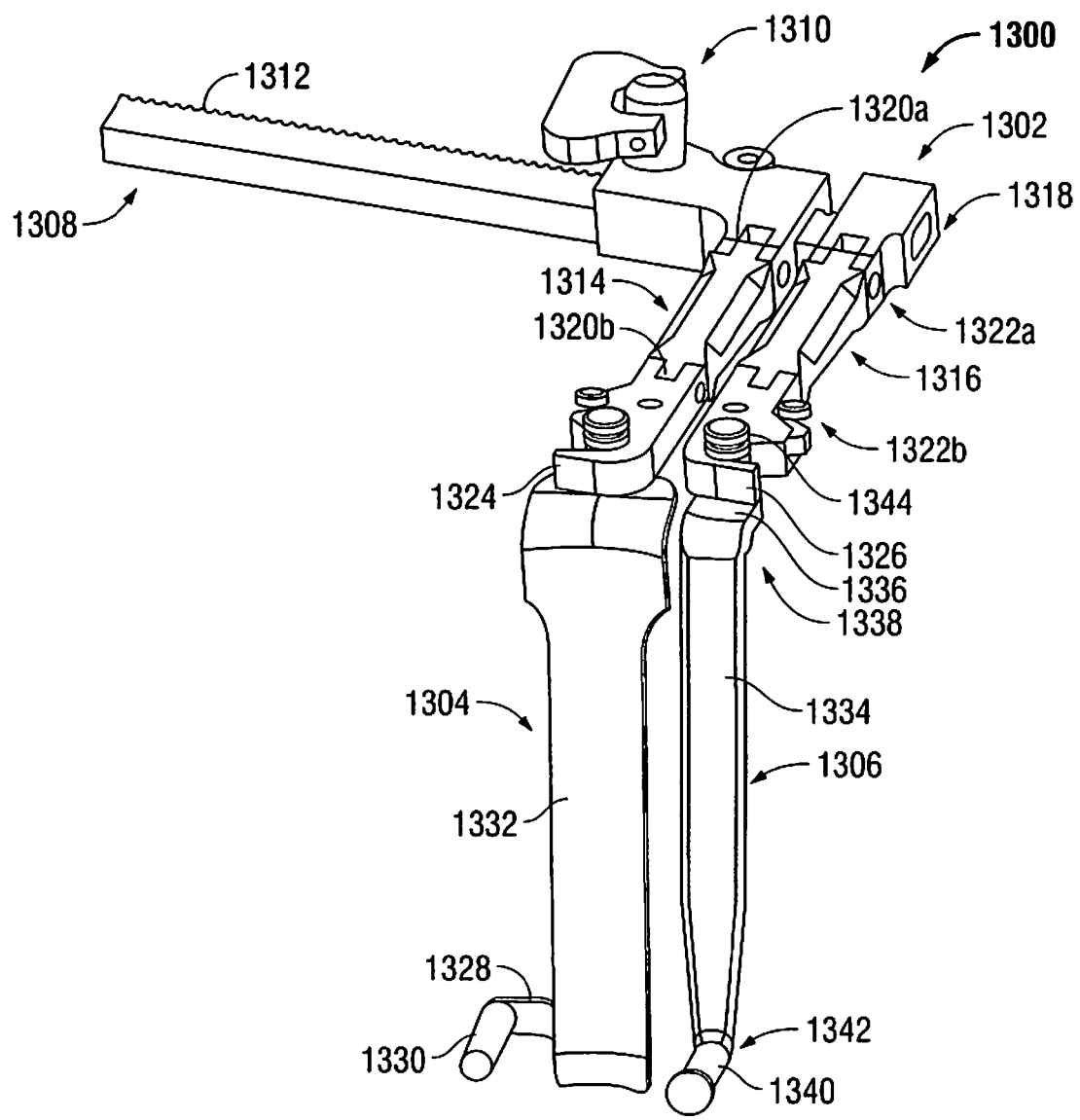
FIG. 36 is a perspective view of a retraction system according to an embodiment of the present disclosure.

FIG. 36 depicts another embodiment of a retraction system 1300. Retraction system 1300 contains a ratchet mechanism 1302 operatively connected to a retraction blade 1304 and a distraction post 1306. Ratchet mechanism 1302 includes a rack 1308 having teeth 1312 and locking device 1310, such as a pawl, configured to engage the teeth 1312 of rack 1308 and slide along the length of rack 1208. A first support arm 1314 connects locking device 1310 to retraction blade 1304, whereas a second support arm 1316 fixedly couples distraction post 1306 to an end portion 1318 of the rack 1308. Since locking device 1310 is capable of moving along rack 1308 and locking device 1310 is operatively attached to first support arm 1314, first support arm 1314 can move away and toward second support arm 1316. Hinges 1320a, 1320b located in first support arm 1314 allow first support arm 1314 to pivot about certain pivoting points along its length. Likewise, second support arm 1316, albeit fixedly attached to rack 1308, includes hinges 1322a, 1322b that permit second support member 1316 to pivot about certain pivoting points along its length. First and second support members 1314, 1316 also include corresponding respective connecting portions 1324, 1326 adapted to hold retraction blade 1304 and distraction post 1306, respectively.

Retraction blade 1304 is substantially similar to the retraction blade 200 shown in FIGS. 27 and 28; however, the laterally offset arm 1328 and rod-shaped portion 1330 of retraction blade 1304 are located on an opposite lateral side of retraction blade portion 1332 as compared to laterally offset arm 216 and rod-shaped portion 214 of retraction blade 200. Given that retraction blade 1304 is operatively connected to locking device 1310 through first support member 1314, translating locking device 1310 along rack 1308 moves retraction blade 1304 away or toward distraction post 1306. When retraction blade 1304 moves away from distraction post 1306, the distance between rod-shaped portion 1300 and the rod-shaped portion 1340 of distraction post 1306 increases. On the other hand, when retraction blade 1304 moves toward distraction post 1306, the distance between rod-shaped portion 1300 and rod-shaped portion 1340 of distraction post 1306 decreases.

Distraction post 1306 includes a body portion 1334, a proximal flange 1336 extending in a substantially orthogonal direction from a proximal region 1338 of the body portion 1334, and a rod-shaped portion 1340 extending substantially perpendicular from a distal region 1342 of body portion 1334. Proximal flange 1336 contains a quick release connection extension 1344 extending proximally therefrom. Connection extension 1344 is configured to be coupled to the connection portion 1326 of second support arm 1316.

Surgeons may use retraction system 1300 for, among other things, spacing apart vertebral bodies. In a surgical procedure, the physician initially introduces pedicle screws into vertebral bodies. Thereafter, the surgeon places a portion of retraction system inside a patient's body in order to secure rod-portions 1330, 1340 to the pedicle screws attached to the vertebral bodies. While coupling the rod-shaped portions 1330, 1340 with the pedicle screws, retraction blade 1304 and distraction post 1306 must be in an approximated position. To space apart the pedicle screws, the surgeon separate retraction blade 1304 from distraction post 1306 with ratchet mechanism 1302. During this process, ratchet mechanism 1302 is positioned above the patient's skin. By moving locking device 1310 away from the end portion 1318 of rack 1308, the surgeon increases the distance between rods-shaped portion 1330 of retraction blade 1304 and rod-shaped portion 1340 of distraction post 1306, thereby spacing apart the vertebral bodies attached to the pedicle screws. Once the surgeon has spaced apart the pedicle screws, the surgeon locks first support member 1314 by engaging locking device 1310 to teeth 1312 of rack 1308.

Figure 37:
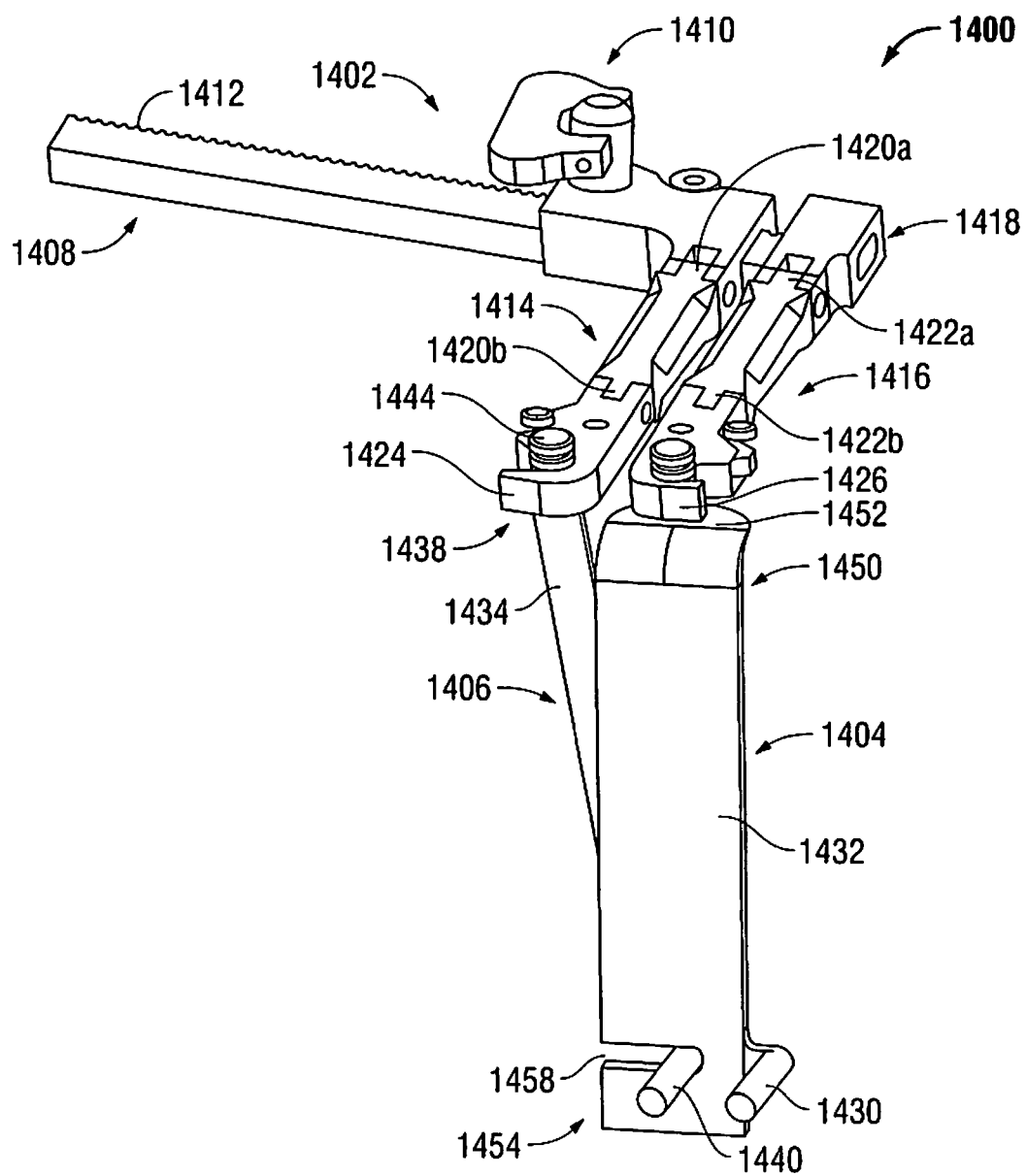
FIG. 37 is a perspective view of a retraction system according to an embodiment of the present disclosure.
Figure 38:
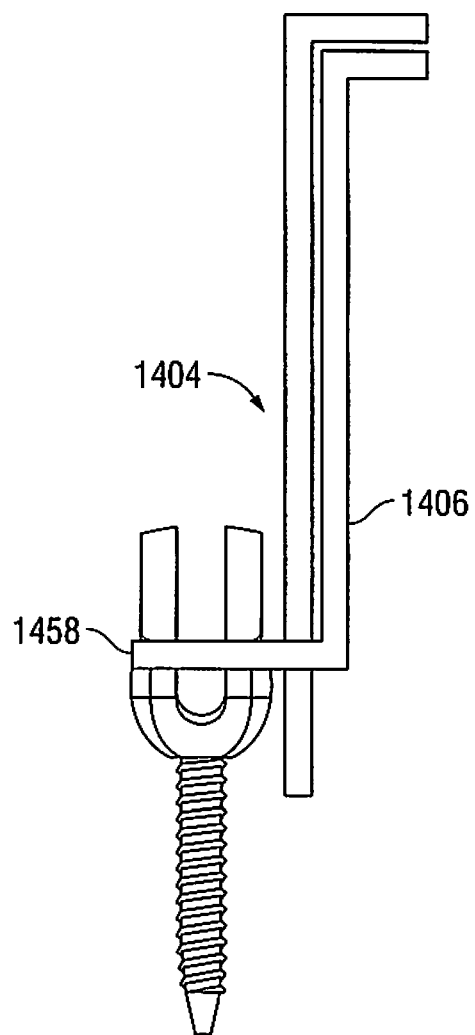
FIG. 38 is a side view of the retraction system of FIG. 37 without the rod-shaped portion of the retraction blade.
Figure 39:
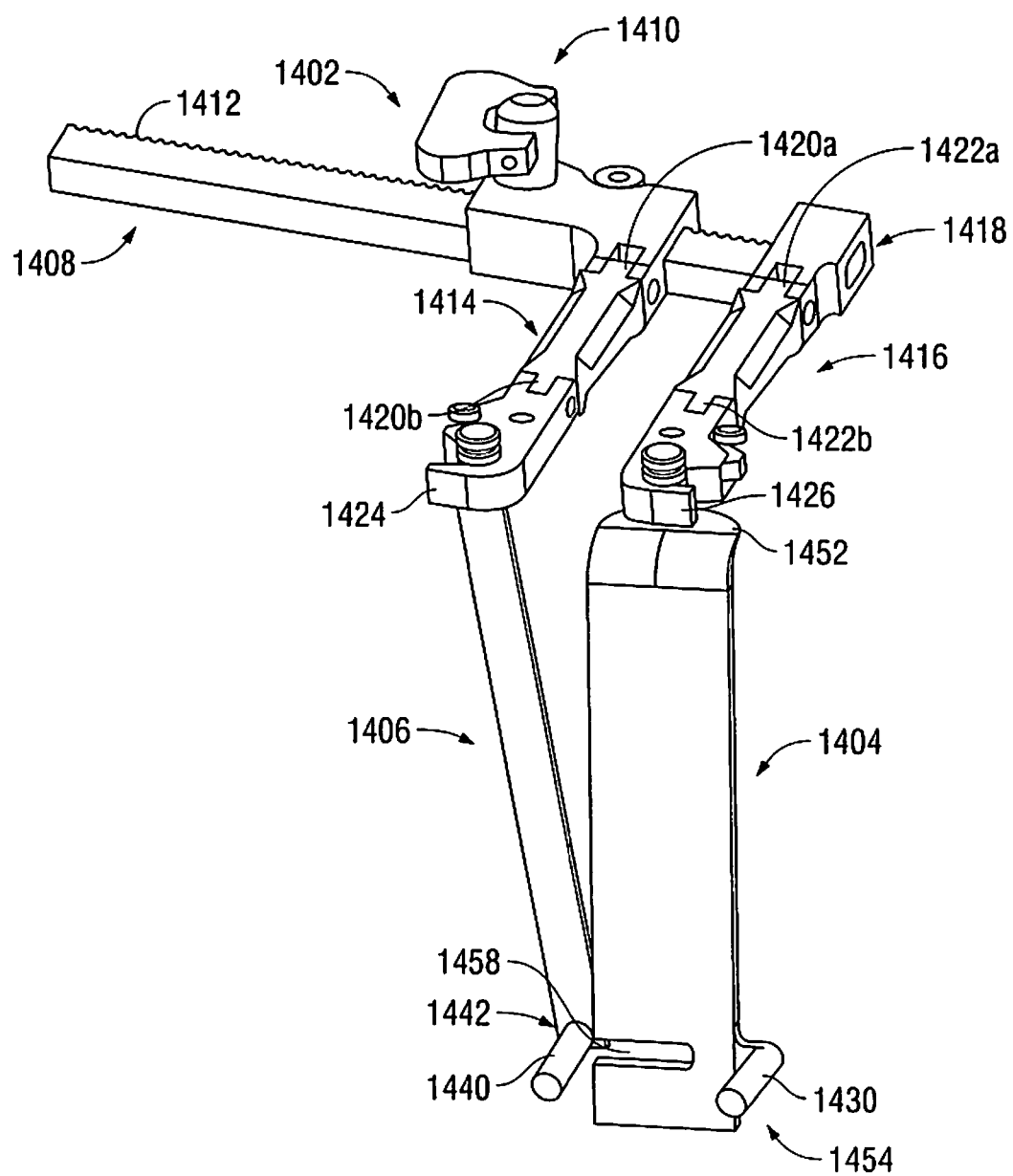
FIG. 39 is a perspective view of the retraction system of FIG. 37 with the retraction blade and the distraction post spaced apart from each other.

With reference to FIGS. 37-39, an alternate embodiment of the retraction system is generally designated as 1400. Retraction system 1400 is similar to retraction system 1300 but includes, among other things, an angled distraction post 1406. Overall, retraction system 1400 features a ratchet mechanism 1402 operatively coupled to angled distraction post 1434 and retraction blade 1404. Like retraction mechanism 1302, retraction mechanism 1402 contains a rack 1408 with teeth 1412 and a locking device 1410, such as a pawl, configured to slide along the length of the rack 1408 and adapted to engage the teeth 1412 of the rack 1408. A first support arm 1414 couples locking device 1410 to angled distraction post 1434, and a second support arm 1416 fixedly connects an end portion 1418 of rack 408 to retraction blade 1404. Each of the first and second support arms 1414, 1416 includes hinges 1420a, 1420b and 1422a, 1422b, respectively. Hinges 1420a, 1420b allow first support arm 1414 to pivot about certain pivot points along its length. Similarly, hinges 1422a, 1422b permits second support arm 1416 to pivot about certain pivot points along its length. In addition to hinges 1420a, 1420b and 1422a, 1422b, each of the first and second arms 1414, 1416 includes a connecting portion 1424, 1426 adapted to be connected to distraction post 1406 and retraction blade 1404, respectively.

Angled distraction post 1406 is not parallel to retraction blade 1404. Rather, angled distraction post 1406 defines an angle with respect to retraction blade 1404. Aside from its spatial arrangement, angled distraction post 1406 features a quick release connection portion 1444 located at a proximal end 1438 thereof and a rod-shaped portion 1440 positioned at a distal end 1442 thereof. Quick release connection portion 1444 is configured to be coupled to the connection portion 1424 of first support arm 1414. Rod-shaped portion 1440 extends substantially perpendicular from the distal foot 1454 and is adapted to be secured in the rod-receiving channel of a pedicle screw, as shown in FIG. 38.

Figure 40:
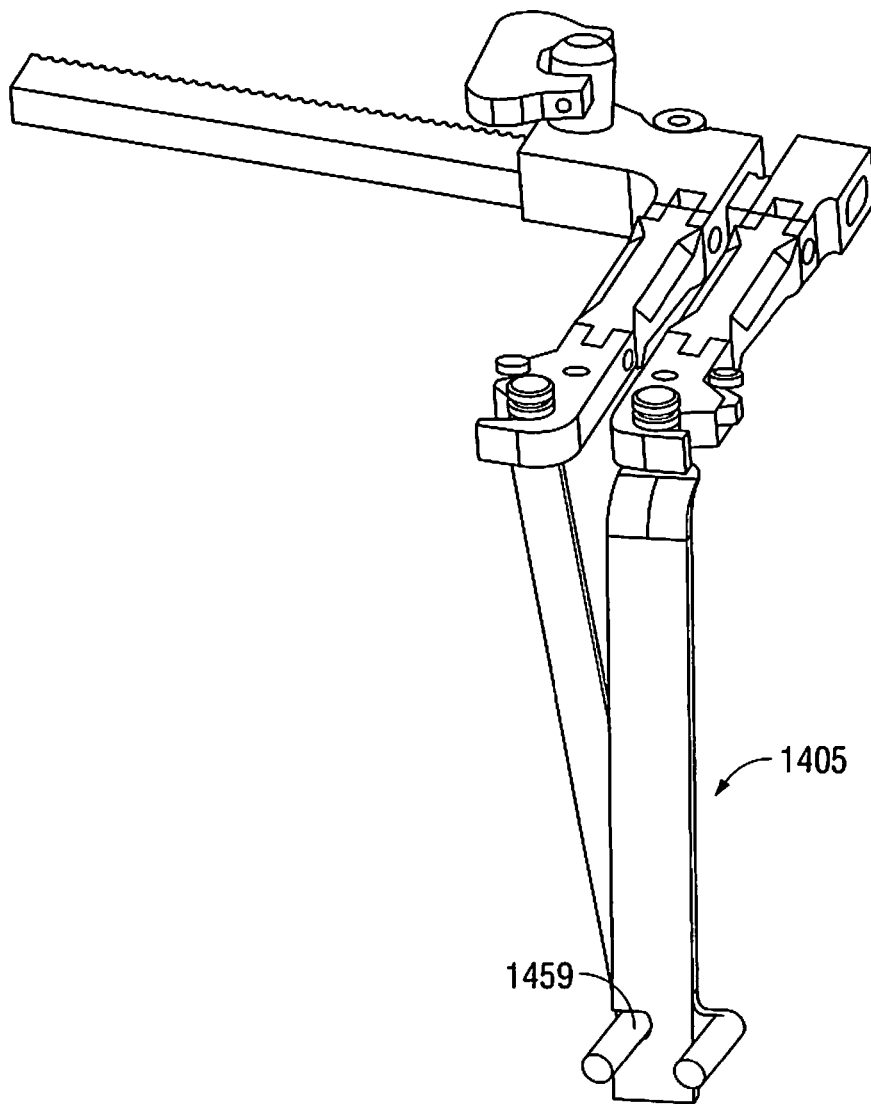
FIG. 40 is a perspective view of a retraction system according to an embodiment of the present disclosure.
Figure 41:
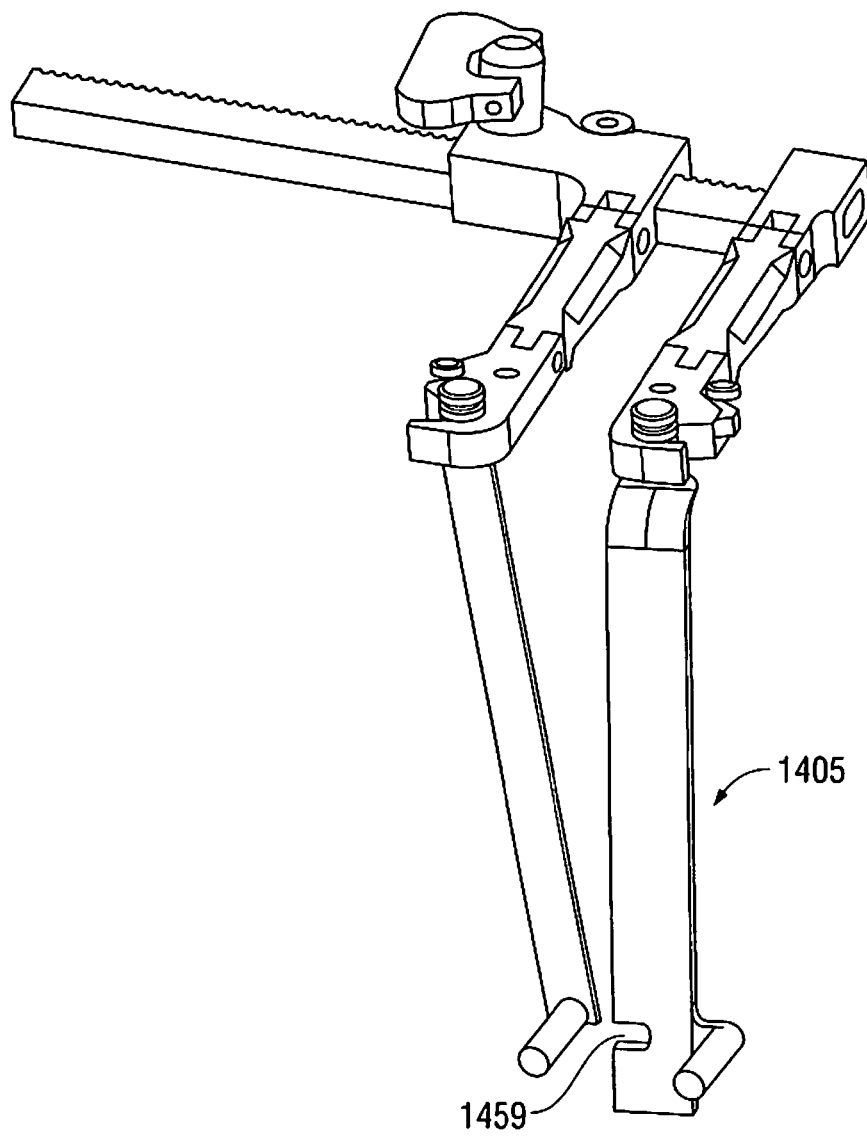
FIG. 41 is a perspective view of the retraction system of FIG. 40 with the distraction post spaced apart from the retraction blade.

Refraction blade 1404 contains a retraction blade portion 1432, a proximal flange 1452 extending substantially perpendicular from a proximal region 1450 of retraction blade portion 1432, and a distal foot 1454. Proximal flange 1452 features a quick release connection portion 1456 adapted to be attached to connecting portion of second support arm 1416. Distal foot 1454 includes a rod-shaped portion 1430 extending substantially perpendicular from a lateral side thereof. Rod-shaped portion 1430 is adapted to be secured in a rod-receiving channel of a pedicle screw. Distal foot 1454 further includes a slot 1458 adapted to slidably receive rod-shaped portion 1440 of distraction post 1406. Alternatively, retraction system 1400 may include a narrower retraction blade 1405 with shorter slot 1459, as depicted in FIGS. 40 and 41.

Rod-shaped portion 1440 of distraction post 1406 is positioned within slot 1458 when retraction blade 1404 and distraction post 1440 are approximated to each other. Rod-shaped portion 1440 slides out of slot 1458 upon moving distraction post 1406 away from retraction blade 1404. To move distraction post 1406 away from retraction blade 1404, the surgeon moves locking device 1410 along rack 1408 away from end portion 1418 until the distraction post 1406 reaches the desired location, as shown in FIG. 39. The surgeon then engages locking device 1410 into teeth 1412 in order to lock distraction post 1406 at the desired position.

In a surgical procedure, pedicle screws are first inserted into vertebral bodies. The surgeon subsequently secures the rod-shaped portions 1430, 1440 to the pedicle screws. After fixing the rod-shaped portions 1430, 1440 to the pedicle screws, the surgeon moves distraction post 1406 away from retraction blade 1404 with ratchet mechanism 1402 to separate the pedicle screws.

Figure 42:
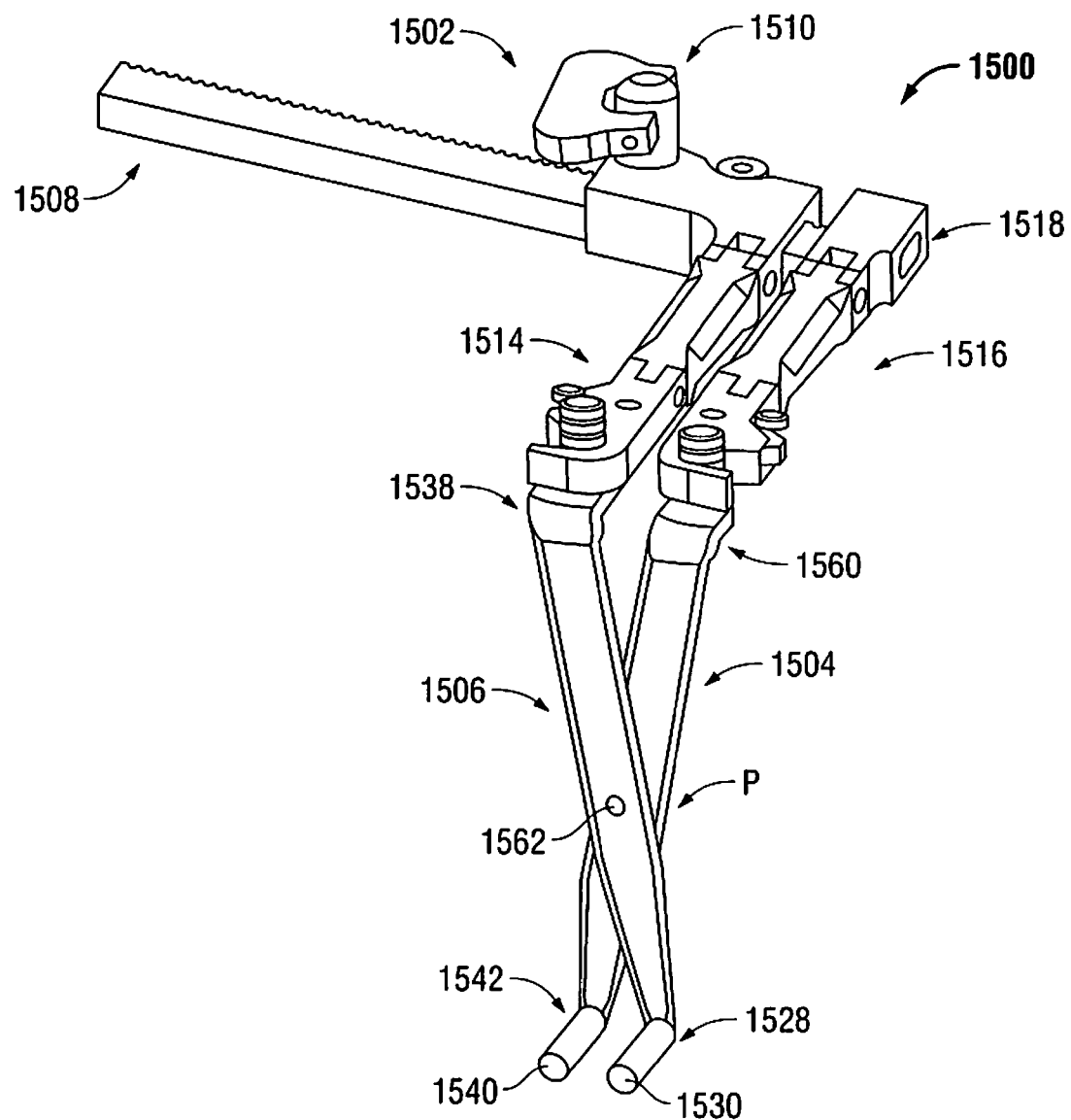
FIG. 42 is a perspective view of a retraction system according to an embodiment of the present disclosure.
Figure 43:
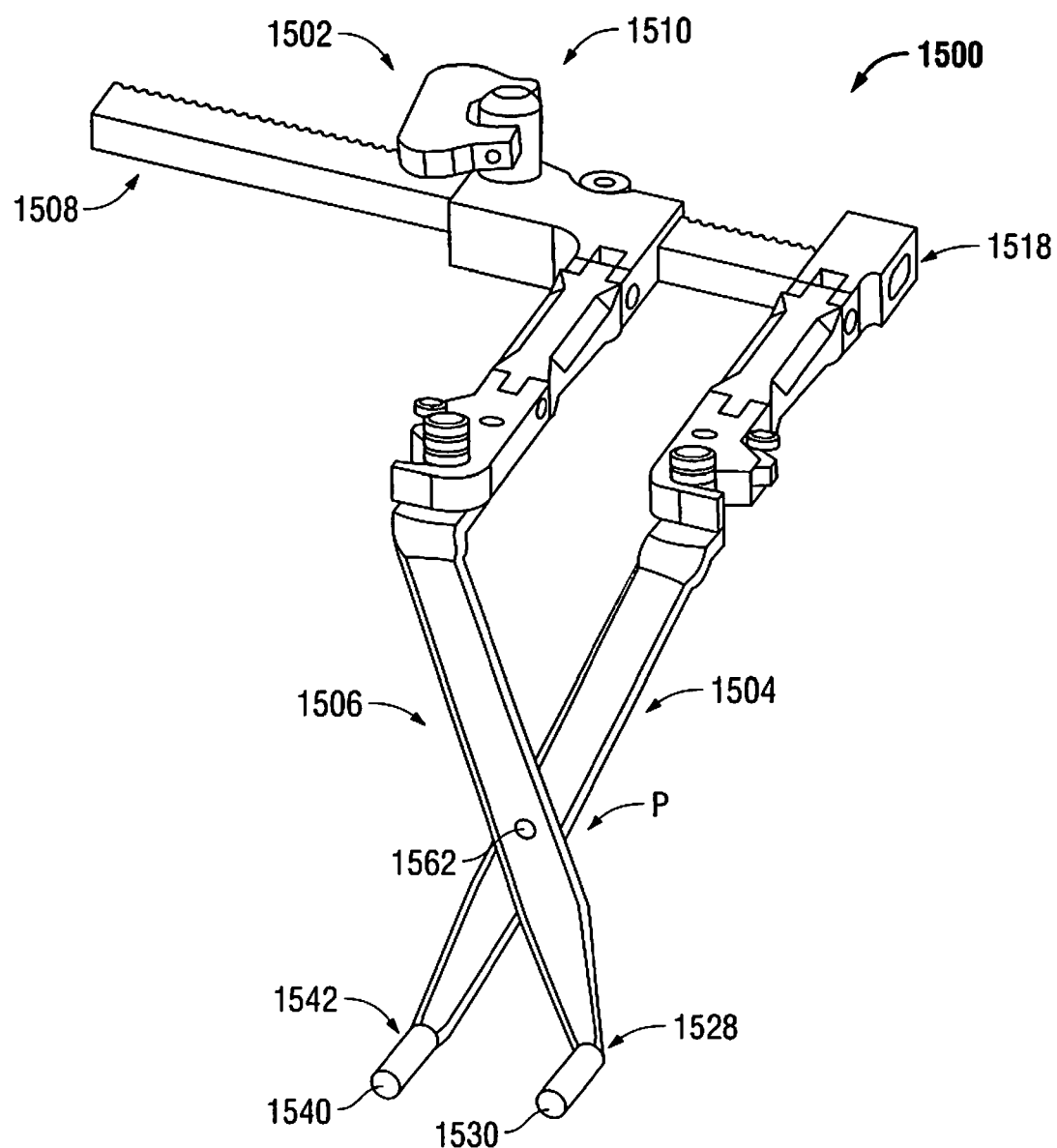
FIG. 43 is a perspective view of the retraction system of FIG. 41 with the distraction posts spaced apart from each other.

With reference to FIGS. 42 and 43, a retraction system is generally designated as 1500. The structure and operation of retraction system 1500 is substantially similar to the structure and operation of retraction system 1400. Nevertheless, retraction system 1500 includes a pair of distraction posts 1504, 1506 pivotally interconnected at a central pivot point "P" instead of a distraction post independently movable from a refraction blade. A pivot pin 1562, or any other suitable apparatus, couples first and second distraction posts 1506, 1504 at pivot point "P." Retraction system 1500 further includes a ratchet mechanism 1502 substantially similar to ratchet mechanism 1402. Ratchet mechanism 1502 is operatively coupled to first and second arms 1514, 1516. Second support arm 1516 is fixed to an end portion 1518 portion of a rack 1508 of ratchet mechanism 1518, and first support arm 1514 is movable relative to rack 1508. Ratchet mechanism 1502 is configured to move first support arm 1514 toward or away from second support arm 1516. Ratchet mechanism 1502 further includes a locking device 1510, such a pawl, capable of engaging the teeth 1512 of rack 1508 and locking and moving first support arm 1514.

First support arm 1514 is operatively connected to first distraction post 1506, and second support arm 1516 is operatively coupled to second distraction post 1504. First and second distraction posts 1506, 1504 are substantially similar to distraction post 1306. As discussed above, a pivot pin, or any other suitable device, pivotally connects first and second distraction post 1506, 1504 at pivot point "P." Hence, first and second distraction posts 1506, 1504 pivot about pivot point "P" relative to each other upon moving first distraction post 1506.

Given that first support member 1514 arm connects locking device 1510 to a proximal portion 1438 of first distraction post 1506, moving the locking device 1510 along rack 1508 moves the proximal portion 1438 of first distraction post 1506 away from a proximal portion 1560 of second distraction post 1506. While the proximal portions 1538, 1560 of first and second distraction posts 1506, 1504 move away from each other, first and second distraction posts 1506, 1504 pivot about pivot point "P" and distal portions 1528, 1542 of first and second distraction posts 1506, 1504 move away from each other, as seen in FIG. 43. Each distal portion 1428, 1442 includes a respective rod-shaped portion 1530, 1540 extending substantially perpendicularly therefrom. Rod-shaped portions 1530, 1540 are each adapted to be secured to a pedicle screw.

During a surgical operation, rod-shaped portions 1530, 1540 are secured to pedicle screws fixed to vertebral bodies, while distal portions 1528, 1542 are approximated to each other. Thereafter, the surgeon separates rod-shaped portions 1530, 1540 from each other with ratchet mechanism 1502, thereby spacing apart the pedicle screws secured to rod-shaped portions 1530, 1530. Throughout this surgical procedure, ratchet mechanism 1506 is located above the patient's skin.

Figure 44:
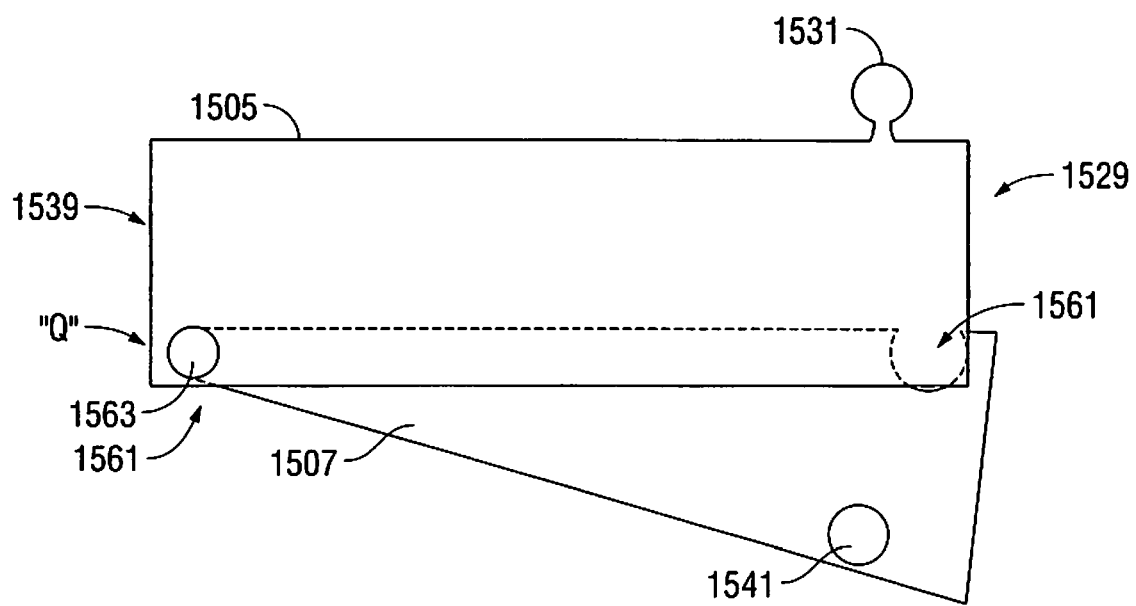
FIG. 44 is a side view of a retraction system according to an embodiment of the present disclosure.
Figure 45:
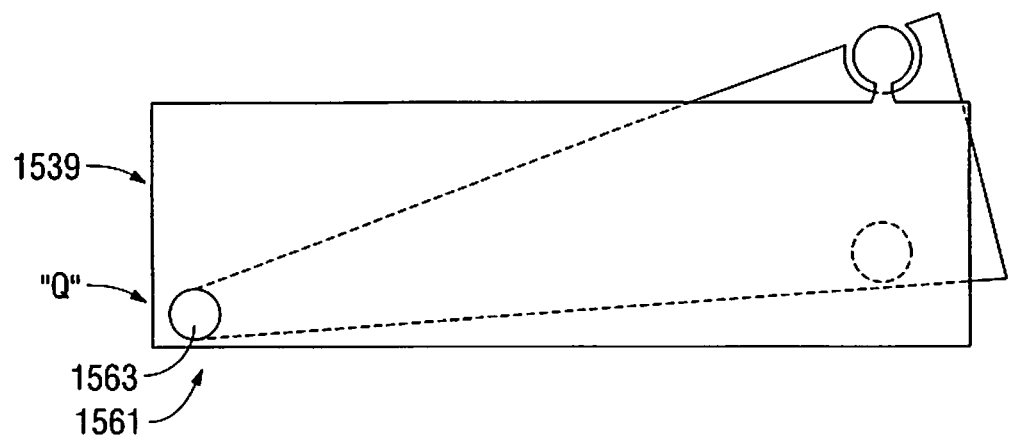
FIG. 45 is a side view of the retraction system of FIG. 44 with the rod-shaped portions according to an embodiment of the present disclosure.

In an alternate embodiment shown in FIG. 44, distraction posts 1506, 1504 may be substituted by retraction blades 1505, 1507. A pivot pin 1563, or any other suitable apparatus, pivotally couples retraction blades 1505, 1507 to each other at a pivot point "Q." Pivot point "Q" is located in proximal region 1539, 1561 of retraction blades 1505, 1507. Retraction blade 1505 has a substantially rectangular shape and contains a rod-shaped portion 1531 positioned at a distal region 1529 thereof. Retraction blade 1507 has a triangular shape and includes a rod-shaped 1541 and a slot 1561 adapted to receive rod-shaped portion 1531 of retraction blade 1505. Slot 1561 receives rod-shaped portion 1531 when rod shaped portions 1531, 1541 are in an approximated position, as shown in FIG. 45. Conversely, rod-shaped portion 1531 is not located within slot 1561 when rod-shaped portions 1541, 1531 are spaced apart from each other, as seen in FIG. 44.

With reference to FIGS. 46-50, another embodiment of the presently disclosed retraction system is generally designated as 1600. Retraction system 1600 includes translation mechanism 1602 operatively associated with first and second retraction blades 1604, 1606. Translation mechanism 1602 contains a translation bar 1608 and a locking device 1610 configured to move along the translation bar 1608. Locking device 1610 has a locking handle 1612 and a translation handle 1614. Actuation locking handle 1612 fixes the position of locking device 1602 with respect to translation bar 1608, thereby switching translation mechanism 1602 to a locked state. When translation mechanism 1602 is in an unlocked state, a user may displace locking device 1610 along translation bar 1608 by manually manipulating translation bar 1614.

Figure 46:
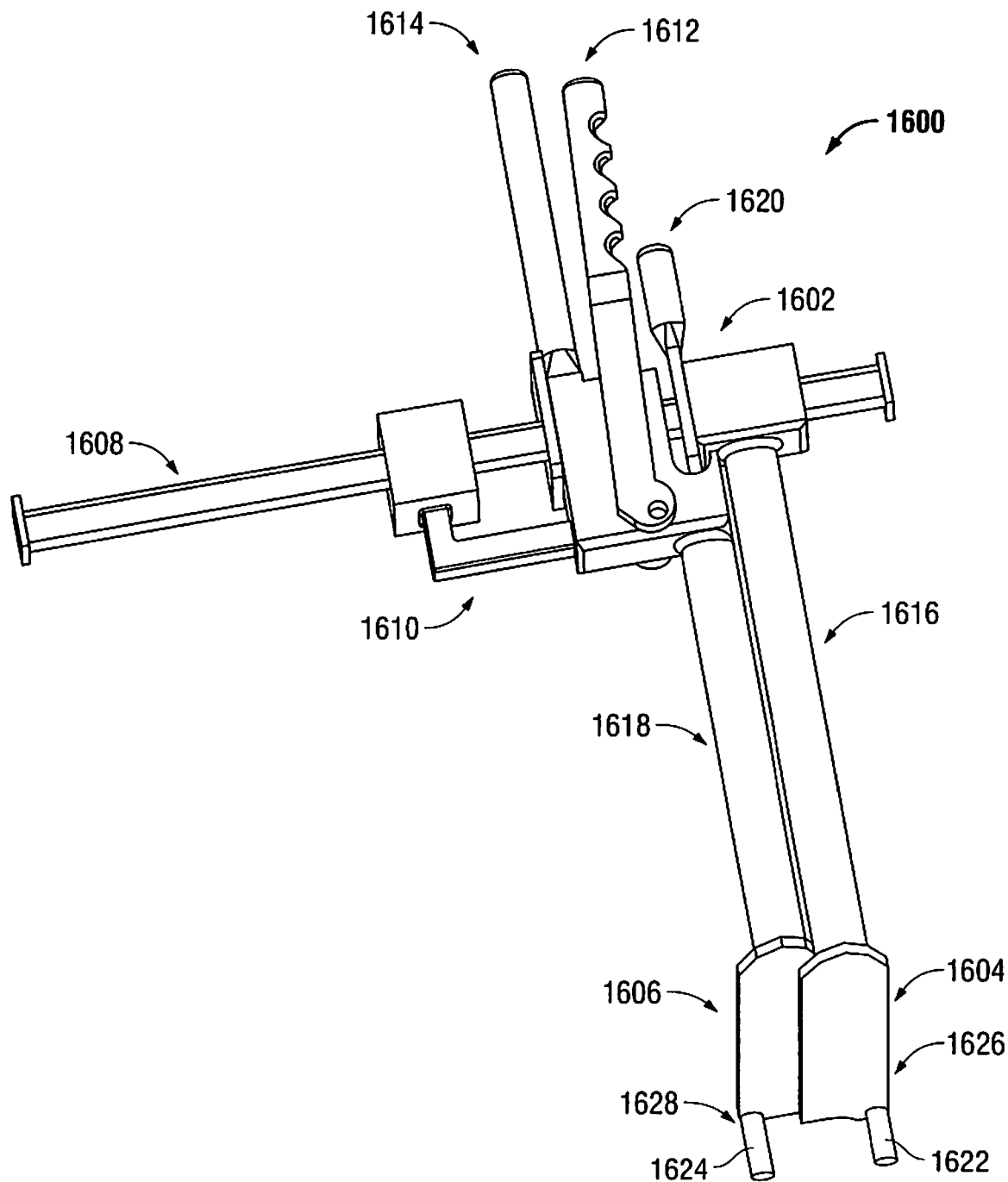
FIG. 46 is a perspective view of a retraction system according to an embodiment of the present disclosure.
Figure 47:
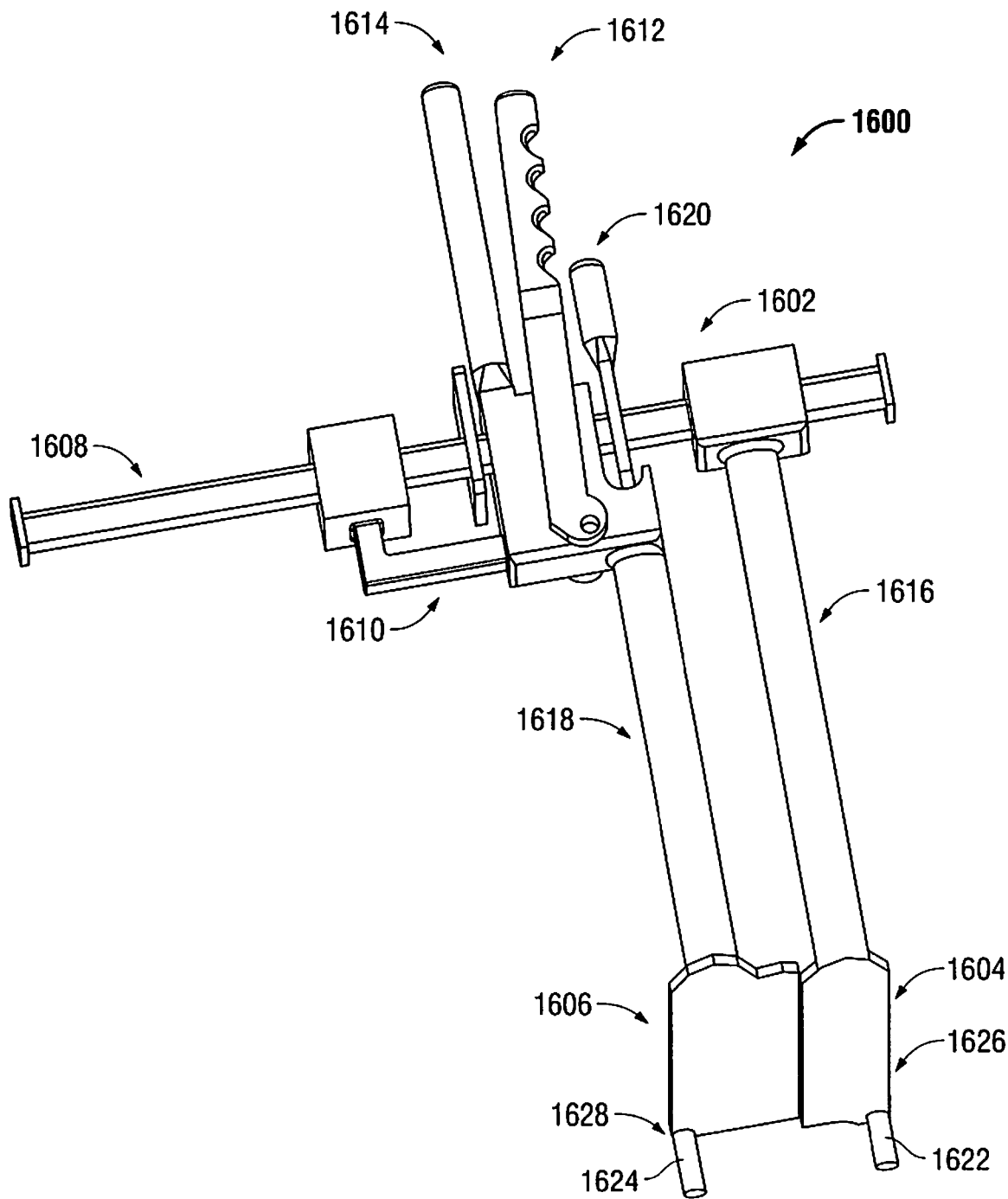
FIG. 47 is a perspective view of the retraction system of FIG. 46 showing the rod-shaped portions spaced apart from each other.

A first support arm 1616 connects translation mechanism 1608 to first retraction blade 1604. Translation mechanism 1608 is not configured to move first support arm 1616. First support arm 1616 remains stationary during the operation of translation mechanism 1602. A second support arm 1618 couples translation mechanism 1602 to second retraction blade 1606. Specifically, second support arm 1618 is attached to locking device 1610. Hence, second support arm 1618 moves as locking device 1610 slides along translation bar 1608, as illustrated in FIG. 47. As seen in FIG. 46, first retraction blade 1604 overlaps second retraction blade 1606, when first and second support arms 1616, 1618 are approximated to each other. In the depicted embodiment, second retraction blade 1606 lies behind first retraction blade 1604.

Retraction system 1600 also includes a plunger 1620 for adjusting the longitudinal distance between first and second retraction blades 1604, 1606. Plunger 1620 is operatively attached to second support arm 1618 and is configured to move support member 1618 longitudinally. Because second support member 1618 is connected to second retraction blade 1606, actuating plunger 1620 moves second retraction blade 1606 longitudinally relative to first retraction blade 1604.

Figure 48:
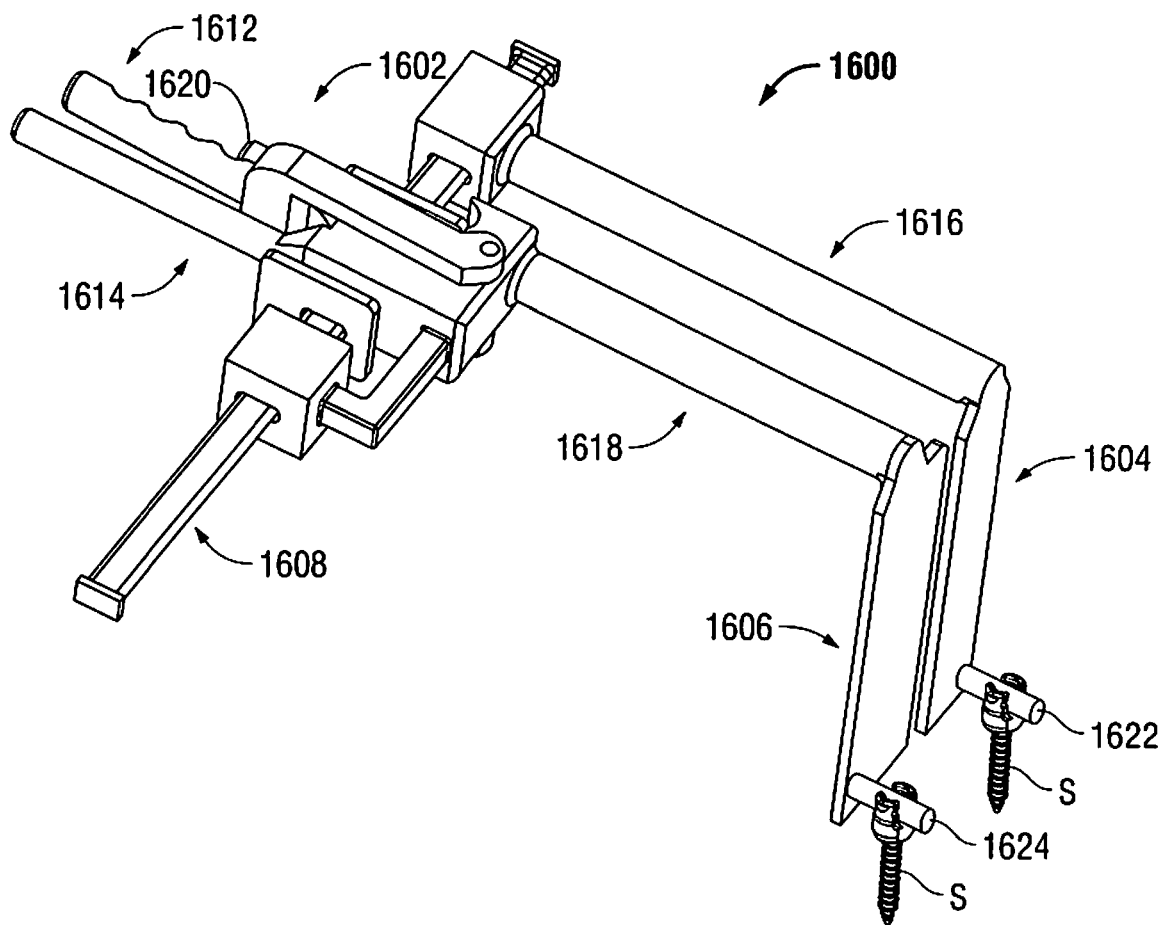
FIG. 48 is a perspective view of the retraction system of FIG. 46 with pedicle screws secured to the rod-shaped portions.
Figure 49:
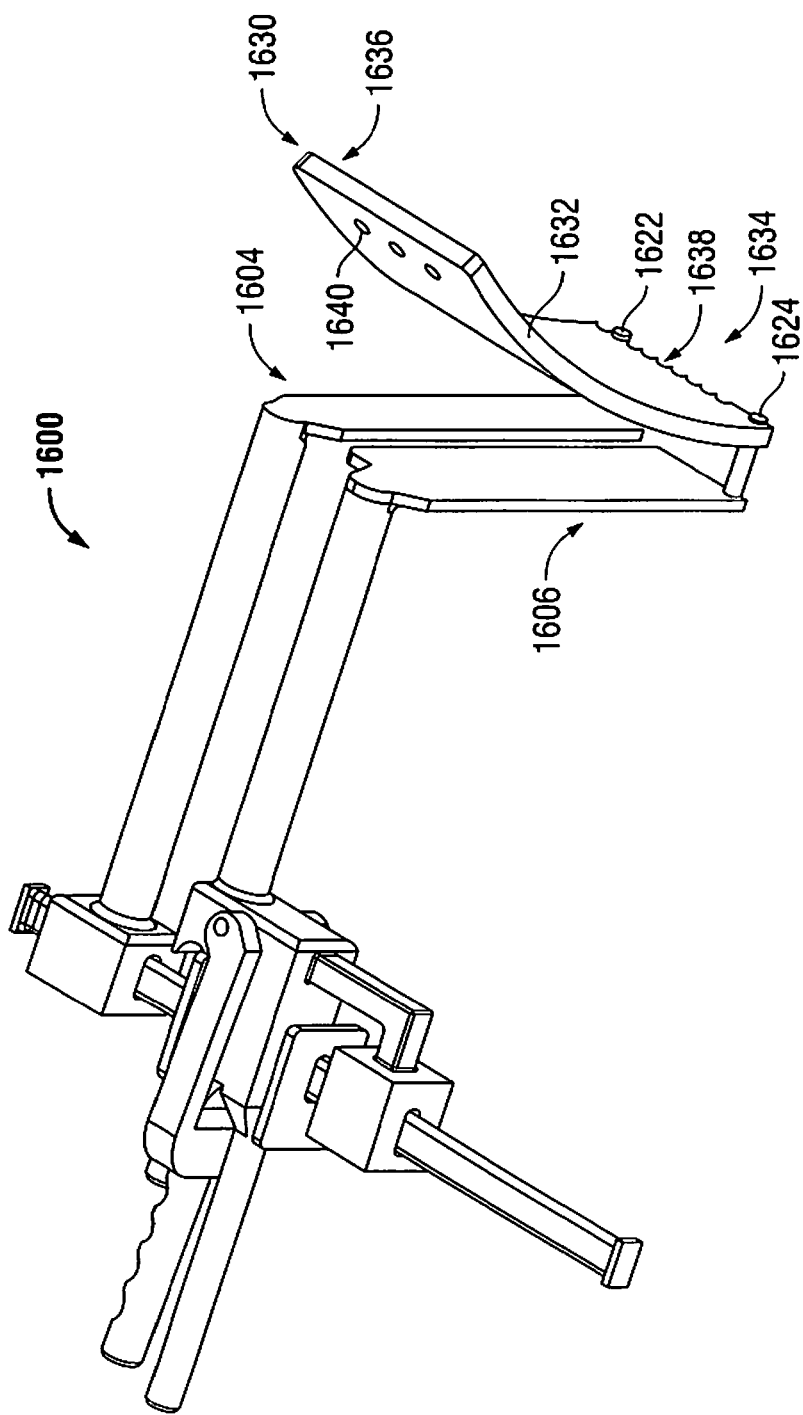
FIG. 49 is a perspective view of the retraction system of FIG. 46 with a curved plate attached to the rod-shaped portions.
Figure 50:
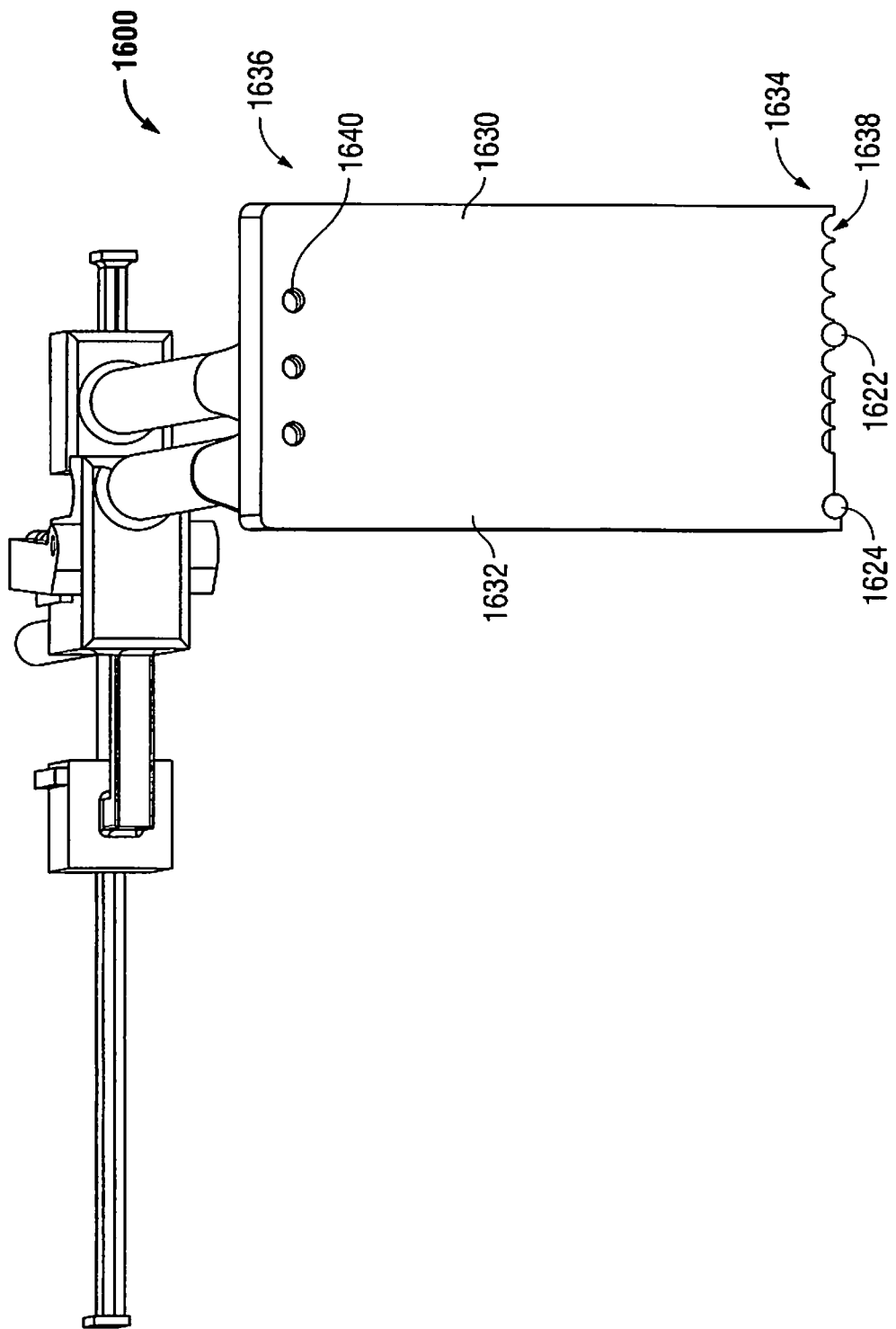
FIG. 50 is a front perspective view of the retraction system of FIG. 46 with the curved plate attached to the rod-shaped portions.

First and second retraction blades 1604, 1606 each include corresponding rod-shaped portions 1622, 1624 extending substantially perpendicular from distal regions 1626, 1628 of retraction blades 1604, 1606. Each rod-shaped portion 1622, 1624 is adapted to be secured to a pedicle screw, as illustrated in FIG. 48. In particular, rod-shaped portions 1622, 1624 are each dimensioned to be received by a rod-receiving channel of the pedicle screws "S." Therefore, displacing first retraction blade 1606 away from first retraction blade 1604 with translation mechanism 1602 increases the distance between the pedicle screws "S" attached to rod-shaped portions 1622, 1624, as seen in FIG. 47.

In a surgical operation, a physician utilizes retraction system 1600 to separate pedicle screws attached to vertebral bodies. Initially, the physician inserts pedicle screws into vertebral bodies. Subsequently, the surgeon secures rod-shaped portions 1622, 1624 to the pedicle screws attached to the vertebral bodies. Retraction blades 1626, 1628 are then separated from each other with translation mechanism 1602, thereby spacing apart the pedicle screws. Before separating the pedicle screws, the surgeon may distract soft tissue at the surgical site with a curved plate 1630.

Curved plate 1630 has a curved body 1632, a distal region 1636, and a proximal region 1634. Distal region 1634 features undulations 1638 adapted to receive rod-shaped portions 1622, 1624. Proximal region 1636 includes at least one hole 1640 hole for viewing. In use, the surgeon engages undulations 1638 with rod-shaped portions 1622, 1624 after the retraction system 1600 has been placed within the patient. Then, the surgeon manually moves curved plate 1630 away from retraction blades 1604, 1606 to displace soft tissue.

Referring to FIGS. 20-21, flexible refractor blades 8 are spread apart in a medial-lateral direction to retract tissue in the working area, and to provide access to the pedicle screws. As previously discussed, retractor blades 8 may be spread apart using Gelpi retractor 180 (FIG. 15) or by the physician manually grasping retractor blades 8 to urge them apart. After the desired retraction is achieved, rod 3 is inserted through passage 18 of retractor 10, 10' and 50 into rod receiving channel 44 of pedicle screws 40 (also see FIG. 9).

Once rod 3 is positioned between pairs of pedicle screws 40 and, in particular through the respective rod receiving passage 44 of each screw with appropriate distraction and/or compression, rod 3 is secured in place using set screws or other suitable locking members as previously discussed.

Once the screw-rod construct is complete, retractors 10, 10' and 50 are removed from the patient using retractor extractor 300. Retractor extractor 300 is positioned atop pedicle screw 40 such that optional extension tip 334 of extractor bar 330 (FIG. 18) engages head 42 of pedicle screw 40 (or, alternatively, the flat end rests upon the screw head or rod installed in an alternate pedicle screw such as the taper lock screw previously identified). The physician repositions retractor blades 8 towards arm blades 316, 326 (FIGS. 17-18) of retractor extractor 300 such that posts 302 engage instrument holes 6. Once retractor extractor 300 is installed, the physician pivots handle grip 392 towards arms 310, 320. This pivotable movement drives extractor bar 330 distally against head 42 while simultaneously pulling retractor blades 8 proximally (through engagement of pins 302 with apertures 6 on the flexible retractor, see FIG. 19) such that relief regions R (FIG. 2) separate from each other along slits 16. As such, retractor 10, 10' and 50 is separated from pedicle screw 40 without imparting significant downward or rotational forces against the screw or the patient's body. Retractor 10, 10' and 50 may now be removed from the patient and this process may be repeated for each installed retractor. Normal surgical techniques may be used to close the incision(s).

In an alternate procedure for inserting the pedicle screws, the physician first prepares the surgical site including positioning a guidewire as discussed hereinabove, optionally using cannulated scalpel 120 to prepare an incision, and inserting one of the previously disclosed retractors without a pedicle screw. Once the selected retractor is positioned in a desired location, the physician retracts the surrounding tissue as discussed hereinabove. Subsequently, the physician attaches pedicle screw 40 to the vertebral body V using screw inserter 160. In this method, the selected retractor is already in position prior to attaching pedicle screw 40 to vertebral body V. In particular, the physician assembles pedicle screw 40 and screw inserter 160. Once assembled, the screw insertion assembly is inserted into passage 18 of the retractor and pedicle screw 40 is rotated such that it bores into vertebral body V and head 42 seats on the interior surface of the distal region of the retractor and thus attaches the retractor to vertebral body V. Optionally, the physician may use cannulated bone tap 140 to prepare the bore.

It is contemplated that each flexible retractor may be utilized in, but not limited to, a method whereby an initial incision is made in the skin of approximately 10-20 mm in length. Surgeon preference will dictate the need for one or more stages of dilators to aid in expanding the wound before introducing one or more retractors in combination with pedicle screws.

The disclosed flexible and rigid retractors, as with any surgical instrument and implant, must have the ability to be sterilized using known materials and techniques. Parts may be sterile packed by the manufacturer or sterilized on site by the user. Sterile packed parts may be individually packed or packed in any desirable quantity.

While the method of using rigid retractors for medial-lateral retraction with one of the retractor blades mounted to a pedicle screw has been described herein in relation to percutaneous screw insertion and use in combination with flexible screw based retractors for cephalad-caudad retraction, it is contemplated that the rigid retractor blades may also be utilized in open surgery. Thus, rather than placing the pedicle screws by the percutaneous approach utilizing the flexible screw based retractors, it is contemplated that the surgeon may choose to access the pedicles and implant the pedicle screws by traditional surgical techniques without using a guidewire or retractors 10, 10', 50. Thus, the use of the retractor system of the present disclosure is not limited to use with the flexible retractors. The surgeon may choose to access the pedicles and implant the pedicle screws in any appropriate manner, including an open or mini-open procedure, or by use of some other screw placement method. Thereafter, rigid blade 200 may be secured to one or more of the pedicle screws. The second rigid blade 230 is inserted, the blades are attached to the spreading device, and the movable retractor is spread apart from the retractor mounted to the screw. The surgeon then accesses the facet and disc space, as necessary or appropriate, and performs a procedure thereon or therein. After the procedure is complete, the medial-lateral retractor is removed, a rod is mounted into the pedicle screws, and the incision is closed. The surgeon may subsequently remove some of the distraction and allow compression between the pedicle screws to load a graft positioned between the vertebral bodies. Then, the surgeon secures the rod to the rod receiving channel or saddle of the pedicle screw by installing a set screw or other locking device and finalizing the rod-screw construct.

Another alternative approach that may be used with screws placed by open, mini-open or another method including use of the flexible retractors described herein, involves use of specialized temporary set screw 600 (FIG. 33). Thus, with at least one pedicle screw implanted (whether by open surgical techniques or a less invasive technique such as but not limited to those described herein) temporary set screw 600 is engaged with the head of the implanted screw by driving the screw driving feature. The quick connect proximal head 606 is then connected to a spreading device such as spreading device 250 (see FIG. 31). With one spreading arm attached to the temporary set screw in this manner and thereby fixed relative to the implanted screw, a blade attached to the other spreading arm may be moved apart from the screw by actuating the spreading device. In one such procedure, the movable retractor blade is disposed medially so that actuating the spreading device provides medial retraction. As will be appreciated, in this approach there may or may not be a separate lateral refraction blade. Thus, the surgeon may choose to use a lateral retraction blade mounted in the same pedicle screw and held in place by the specialized temporary set screw, mount a lateral retraction blade in another pedicle screw, use a table or hand held lateral blade, or forego a lateral blade altogether. Even if no lateral blade is used, it has been found that medial retraction relative to a screw may provide an appropriate degree of retraction. As an indication of the flexibility provided to the surgeon by the present system, the surgeon may choose to secure a first rigid retractor blade 200 mounted in the rod receiving recess of an implanted pedicle screw and secured thereto using specialized set screw 600. Thus, the surgeon would have the flexibility of attaching the spreading device arm to either the temporary set screw quick connect or the quick connect on the specialized retractor blade, or moving the spreading arm from one location to the other during the procedure to obtain modified access. It is also contemplated that a refractor blade could be integrated with specialized set screw 600, which of course would require an association of the blade and set screw portions which would permit the set screw to rotate relative to the set screw during engagement of the set screw with the pedicle screw or which would permit the blade portion to be attached to the set screw (such as by sliding down over the set screw) after the set screw has been implanted.

It is also contemplated that the set screws 600 may be used in combination with retractor blades for distracting tissue. In this embodiment, set screws 600 are attached to pedicle screws in selected bony structure. Retractor blades are attached to the set screws such that the practitioner is able to manipulate the retractor blades to distract tissue in a desired region of the patient's body and in a predetermined direction (i.e. cephalad-caudad or medial-lateral). The retractor blade and/or the pedicle screw may be monoaxial or polyaxial. Alternatively, the set screws are attached to pedicle screws in adjacent bony bodies. In this configuration, one or both of the anchored screws are moved relative to one another to retract the adjacent bony bodies. It is further contemplated that any of the disclosed embodiments of pedicle screws and retractors may be used to retract tissue or bony structures.

Alternatively, the presently disclosed pedicle screws and retractors may be used in Anterior Lumbar Interbody Fusion ("ALIF") procedures or in eXtreme Lateral Interbody Fusion ("XLIF") procedures. In an ALIF procedure, the incisions are made in the abdominal region to access the selected vertebral bodies. The XLIF procedure is a minimally invasive approach to the anterior spine that avoids an abdominal and also avoids cutting or disrupting the muscles of the back. In this technique, the disk space is accessed from a very small incision on the patient's side (i.e. far lateral).

It is further contemplated that even if the surgeon elects to use the flexible retractors, he or she may choose not to rotate the flexible retractors 90.degree. as described above in connection with one of the disclosed methods. Indeed, with the specialized set screw the flexible retractors may be left in their ordinary medial-lateral orientation and the temporary set screw mounted to the pedicle screw. The spreading device may then be mounted to the temporary set screw and used with another retractor blade of any desired shape and width to create the desired access to the facets and interbody space.

It will be understood that various modifications may be made to the embodiments of the presently disclosed retraction systems and that different combinations of systems and methods may be constructed. Therefore, the above description should not be construed as limiting, but merely as exemplifications of embodiments. Those skilled in the art will envision other modifications within the scope and spirit of the present disclosure.

For example, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, and to access a surgical target adjacent the screw or pin, a retractor may be mounted to the screw or pin and a movable retractor spread apart therefrom to provide access.

Numerous variations of the systems and methods for spine surgery also are contemplated. For example, although less desired, it is contemplated that the rigid medial-lateral retractors could be used without attachment to any pedicle screw. The use of the flexible screw based retractors to define the cephalad-caudad boundaries of the working channel and medial-lateral retractors to define the medial-lateral boundaries without fixation to the screws may be less desirable but may suffice for some procedures. It is further contemplated that the rigid retractors may find application to surgical procedures without the use of flexible screw based retractors. Thus, there may be reason to use the rigid retractors with one or both blades fixed relative to the screws in open surgery for retraction in any desired direction. For example, it may be desirable to mount the first rigid retractor to one screw during open surgery and to spread the movable blade in a cephalad-caudad or other direction, depending upon the procedure to be performed.

It is further contemplated that the shape and configuration of any of the retractors disclosed herein could be modified or altered for any given application or desired result. In particular, it is contemplated that the width, length, curvature, tissue retaining features (such as angled or curved distal tips) may vary depending upon surgical application and surgeon preference. It is further contemplated that any or all of the retractors described herein could be provided with means to deliver illumination into the working channel. In this regard, the retractors could be provided with appendages to attach fiber optic or other light sources, or could be provided with integral light channels. Providing integral light channels is particularly appropriate if the retractor is made of plastic, and is contemplated with respect to all of the retractors, both flexible and rigid, described herein. The light channels may be configured to provide specular illumination in the working channel of the operating channel, may provide diffuse light throughout the working channel, or both.

It is further contemplated that the spreading devices used to spread apart the flexible retractors and the rigid retractor blades may take different forms and may be integrated together. By way of example, it is contemplated that the spreading device used with the rigid retractors may be a frame type structure of the type described for example in Jako U.S. Pat. Nos. 5,503,617 and 5,813,978 or Hamada U.S. published Patent Application numbers 2007/0038216 and 2006/0271096 both entitled Minimal Incision Maximal Access MIS Spine Instrumentation and Method, 2006/0178693; 2006/0167487; 2005/0240209; 2005/0101985; 2004/0093001; and U.S. Pat. No. 6,849,064 all entitled Minimal Access Lumbar Diskectomy Instrumentation and Method.

Thus, it is contemplated that the structures disclosed in the foregoing patents and applications or variation thereof may be used to spread or hold the flexible or rigid retractor blades apart. In a simple variation, the flexible retractors might be held apart by being disposed on the outside of a frame as disclosed in the foregoing patents or patent applications with or without being secured thereto. The substantially rigid retractors might be secured to the retractor frame such that the position and pivotal orientation of the blades may be adjusted relative to the frame.

It is further contemplated that the extension member attached to the rigid retractor may be rotationally attached, so that the position of the retractor blade may be rotatably adjusted relative to the screw. In addition, the angle of the extension member need not be orthogonal to the refractor blade, but may be any desired angle. It is also contemplated that it may be desirable to have the extension member situated in the rod receiving channel in line with the axis between the screws in order that the force exerted by the spreading device on the extension member relative to the screw is perpendicular rather than parallel to the rod receiving channel, thereby loading the extension member to screw interface in a manner less susceptible to slippage of the extension member relative to the screw. In this particular example, the extension member might have a stepped configuration so that the extension member sits in the screw receiving channel along the axis between the screws, with the retractor blade lateral offset from the screw-screw axis. The angle of the extension member relative to the retractor blade may be varied for particular applications or desired results.

It is also contemplated that the rigid retractor may be mounted to more than one screw. Thus, the retractor blade may be provided with a plurality of extension members to engage a plurality of implanted pedicle screws, the extension members may be perpendicular to the blade as depicted in FIG. 27, or may be stepped as described above to be received in the rod receiving channels of the screws with the screw channels aligned with each other.

Variations of the disclosed methods also are contemplated. Multiple levels of spine operating may be performed with the devices and methods disclosed herein on one or both sides of the spine. Advantageously, with the TLIF approach described above, access to the intervertebral space is only required on one side of the spine. In the TLIF approach, on the opposite side and at the same level, a screw-rod construct may be percutaneously implanted. By using the flexible percutaneous retractors without forming a skin incision between the screws, the rod may be inserted subcutaneously. In contrast, if a PLIF procedure is to be performed, the method of medial-lateral retraction of an incision between the screws should be repeated on each side.

The instruments and methods may also find application to implantation of posteriorly inserted motion preserving devices. While posteriorly implanted artificial disks are not yet available, it is expected at least some of those devices, when available, may require posterior insertion in multiple segments from each side of the spinal midline. In that situation, the access provided by the current retraction system may be advantageous. One such device is disclosed in published PCT application WO 2007/038418 and corresponding published U.S. Patent Application 2007/0083267 both entitled Posterior Metal on Metal Replacement Device and Method.

The instruments and methods may also find application with dynamic stabilization systems, used alone or in combination with interbody implants or nucleus replacement materials. By way of example, one dynamic stabilization device is shown in WO 2006/119447 entitled Mobile Spine Stabilization Device. An example of a nucleus replacement is shown in U.S. Pat. No. 7,004,945 and published application 2004/0068268 both entitled Devices and Methods for Restoration of a Spinal Disc.

The use of nerve sparing technologies also is gaining favor, particularly in less invasive spine procedures where nerves may not be exposed, visualized and retracted as part of the procedure. Such devices and techniques involve use of an electrical probe to ascertain whether a nerve has been impinged upon by, for example, by an awl, drill, tap or screw placement. This technique is not feasible when metal retractors are used. The flexible plastic retractors (10, 10', 50), dilator 400 and or the instrument introducer sleeve 500 of the present disclosure all are well suited for use with such nerve sparing techniques, as the probe may contact the screw without interference from adjacent metal retractor blades to determine if any nerve disruption has occurred. It is also contemplated that if the substantially rigid retractors are made of plastic, similar advantages may be achieved with those retractors as well.

These and other variations and modifications of the disclosed systems, apparatus and methods will be realized by those informed by the present disclosure, and are contemplated to be part of the present disclosure.

The present disclosure and its use in surgery may provide reduced incision length and/or may reduce trauma to adjacent soft tissue, nerves, vasculature, and musculature when performing spine surgery, which in turn can provide for less pain, scarring and a more rapid recovery from surgery.

The invention claimed is:

1. A method of separating vertebral bodies, comprising:
   positioning a first rod-shaped portion of a retractor within a rod receiving passage of a first pedicle screw having a threaded shank implanted in a first vertebral body, such that the first rod-shaped portion is oriented transversely to the threaded shank of the first pedicle screw;
   positioning a second rod-shaped portion of the retractor within a rod receiving passage of a second pedicle screw having a threaded shank implanted in a second vertebral body, such that the second rod-shaped portion is oriented transversely to the threaded shank of the second pedicle screw;
   actuating a spreading device coupled to the first and second rod-shaped portions of the retractor to induce a movement of either one of the first and second rod-shaped portions away from the other from a first distance apart to a second distance apart along a distraction axis, the second distance being larger than the first distance, wherein the movement displaces the first and second vertebral bodies with respect to one another, and wherein the retractor limits the movement of the first and second rod-shaped portions by ratcheting so as to permit the first and second rod-shaped portions to move away from one another along the distraction axis while preventing the first and second rod-shaped portions from moving towards one another along the distraction axis; and disengaging and removing the spreading device from the first and second rod-shaped portions while the retractor maintains the first and second rod-shaped portions at the second distance apart.

2. The method of claim 1, further comprising implanting the threaded shanks of the first and second pedicle screws in the respective first and second vertebral bodies before the steps of positioning the first and second rod-shaped portions within the rod receiving passages of the respective first and second pedicle screws.

3. The method of claim 1, further comprising securing the first and second rod-shaped portions of the retractor within the respective rod receiving passages of the first and second pedicle screws.

4. The method of claim 3, wherein securing the first and second rod-shaped portions comprises advancing a first set screw into engagement with the first rod-shaped portion and advancing a second set screw into engagement with the second rod-shaped portion.

5. The method of claim 1, further comprising positioning a rod in an implanted position extending within the rod receiving passages of both of the first and second pedicle screws.

6. The method of claim 1, further comprising retracting tissue away from the distraction axis between the first and second pedicle screws.

7. The method of claim 6, wherein the first pedicle screw includes first and second elongated retractor blades connected thereto on opposing sides of the rod receiving passage of the first pedicle screw.

8. The method of claim 6, wherein the first and second rod-shaped portions are connected to a retractor blade, the step of retracting tissue away from the distraction axis comprising positioning the retractor blade in an incision proximate the first and second vertebral bodies.

9. The method of claim 8, further comprising moving the retractor blade away from the distraction axis to further retract tissue.

10. The method of claim 8, wherein the first and second rod-shaped portions are connected to a distal end of the retractor blade.

11. The method of claim 10, wherein a proximal end of the retractor blade is coupled to a frame.

12. The method of claim 11, further comprising coupling a connector of the retractor blade to the frame.

13. The method of claim 11, wherein a second retractor blade is coupled to the frame such that the retractor blade and the second retractor blade face one another on opposing sides of the distraction axis.

14. The method of claim 11, wherein a third retractor blade and a fourth retractor blade are coupled to the frame such that the third and fourth retractor blades are movable away from one another along the distraction axis.

15. The method of claim 1, wherein the ratcheting of the retractor comprises moving a pawl along teeth formed on an arm extending along the distraction axis and coupled to the second rod-shaped portion.

16. The method of claim 1, further comprising orienting the rod receiving passages of the first and second pedicle screws transverse to the distraction axis before positioning the first and second rod-shaped portions within the respective rod receiving passages.

17. A method of separating vertebral bodies, comprising:
coupling a retractor to a first pedicle screw and a second pedicle screw implanted in a first vertebral body and a second vertebral body, respectively, the coupling step including positioning a first rod-shaped portion of the retractor within a rod receiving passage of the first pedicle screw along an orientation transverse to a threaded shank of the first pedicle screw, and positioning a second rod-shaped portion of the retractor within a rod receiving passage of the second pedicle screw along an orientation transverse to a threaded shank of the second pedicle screw;

actuating a spreading device coupled to the first and second rod-shaped portions of the retractor to induce a movement of either one of the first and second rod-shaped portions away from the other from a first distance apart to a second distance apart, the second distance being larger than the first distance, the movement displacing the first and second vertebral bodies with respect to one another while a ratchet of the retractor automatically restricts the first and second rod-shaped portions of the retractor from moving towards one another; and disengaging and removing the spreading device from the first and second rod-shaped portions while the retractor maintains the first and second rod-shaped portions at the second distance apart.

* * * * *